(12) United States Patent
Shelton, IV et al.

(10) Patent No.: US 12,295,576 B2
(45) Date of Patent: May 13, 2025

(54) ZONED ALGORITHM ADAPTIVE CHANGES BASED ON CORRELATION OF COOPERATIVE COMPRESSION CONTRIBUTIONS OF TISSUE

(71) Applicant: Cilag GmbH International, Zug (CH)

(72) Inventors: Frederick E. Shelton, IV, Hillsboro, OH (US); Shane R. Adams, Lebanon, OH (US); Nicholas J. Ross, Franklin, OH (US); Jason L. Harris, Lebanon, OH (US); Jacqueline C. Aronhalt, Loveland, OH (US); Taylor W. Aronhalt, Loveland, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/379,827

(22) Filed: Oct. 13, 2023

(65) Prior Publication Data

US 2025/0120715 A1    Apr. 17, 2025

(51) Int. Cl.
  *A61B 17/072*    (2006.01)
  *A61B 17/00*    (2006.01)
  *A61B 90/00*    (2016.01)

(52) U.S. Cl.
  CPC .......... *A61B 17/07207* (2013.01); *A61B 2017/00022* (2013.01); *A61B 2017/00398* (2013.01); *A61B 2090/064* (2016.02)

(58) Field of Classification Search
  CPC .............................................. A61B 17/07207
  See application file for complete search history.

(56) References Cited

U.S. PATENT DOCUMENTS

| | | | |
|---|---|---|---|
| 5,403,312 | A | 4/1995 | Yates et al. |
| 5,485,947 | A | 1/1996 | Olson et al. |
| 6,978,921 | B2 | 12/2005 | Shelton, IV et al. |
| 7,000,818 | B2 | 2/2006 | Shelton, IV et al. |
| 7,401,721 | B2 | 7/2008 | Holsten et al. |
| 7,407,075 | B2 | 8/2008 | Holsten et al. |
| 7,422,139 | B2 | 9/2008 | Shelton, IV et al. |
| 7,464,849 | B2 | 12/2008 | Shelton, IV et al. |
| 7,669,746 | B2 | 3/2010 | Shelton, IV |
| 7,670,334 | B2 | 3/2010 | Hueil et al. |
| 7,735,703 | B2 | 6/2010 | Morgan et al. |
| 7,753,245 | B2 | 7/2010 | Boudreaux et al. |

(Continued)

FOREIGN PATENT DOCUMENTS

| | | |
|---|---|---|
| CN | 105919642 A | 9/2016 |
| CN | 105997172 A | 10/2016 |

(Continued)

OTHER PUBLICATIONS

U.S. Appl. No. 17/957,946, filed Sep. 30, 2022.

(Continued)

*Primary Examiner* — Nathaniel C Chukwurah

(57) ABSTRACT

A surgical stapling system is disclosed that comprises a closure driver, a firing driver, and a control circuit. The control circuit is to set a firing force threshold, advance the closure driver, advance the firing driver, monitor a firing force as the firing driver is advanced, compare the firing force to the firing force threshold, and control movement of at least one of the closure driver or the firing driver based on results of the compare and a zone in which the firing driver is positioned.

20 Claims, 16 Drawing Sheets

(56) References Cited

U.S. PATENT DOCUMENTS

| | | |
|---|---|---|
| 7,845,537 B2 | 12/2010 | Shelton, IV et al. |
| 7,980,443 B2 | 7/2011 | Scheib et al. |
| 8,123,100 B2 | 2/2012 | Holsten et al. |
| 8,141,762 B2 | 3/2012 | Bedi et al. |
| 8,210,411 B2 | 7/2012 | Yates et al. |
| 8,220,688 B2 | 7/2012 | Laurent et al. |
| 8,308,040 B2 | 11/2012 | Huang et al. |
| 8,393,514 B2 | 3/2013 | Shelton, Iv et al. |
| 8,499,992 B2 | 8/2013 | Whitman et al. |
| 8,540,133 B2 | 9/2013 | Bedi et al. |
| 8,561,870 B2 | 10/2013 | Baxter, III et al. |
| 8,608,045 B2 | 12/2013 | Smith et al. |
| 8,733,613 B2 | 5/2014 | Huitema et al. |
| 8,864,007 B2 | 10/2014 | Widenhouse et al. |
| 8,876,857 B2 | 11/2014 | Burbank |
| 9,050,083 B2 | 6/2015 | Yates et al. |
| 9,072,535 B2 | 7/2015 | Shelton, IV et al. |
| 9,101,358 B2 | 8/2015 | Kerr et al. |
| 9,131,940 B2 | 9/2015 | Huitema et al. |
| 9,345,481 B2 | 5/2016 | Hall et al. |
| 9,386,988 B2 | 7/2016 | Baxter, III et al. |
| 9,629,631 B2 | 4/2017 | Nicholas et al. |
| 9,770,245 B2 | 9/2017 | Swayze et al. |
| 9,788,835 B2 | 10/2017 | Morgan et al. |
| 9,839,420 B2 | 12/2017 | Shelton, IV et al. |
| 9,844,369 B2 | 12/2017 | Huitema et al. |
| 9,924,944 B2 | 3/2018 | Shelton, IV et al. |
| 9,987,008 B2 | 6/2018 | Scirica et al. |
| 10,080,552 B2 | 9/2018 | Nicholas et al. |
| 10,085,749 B2 | 10/2018 | Cappola et al. |
| 10,105,142 B2 | 10/2018 | Baxter, III et al. |
| 10,123,798 B2 | 11/2018 | Baxter, III et al. |
| 10,130,363 B2 | 11/2018 | Huitema et al. |
| 10,166,023 B2 | 1/2019 | Vendely et al. |
| 10,213,203 B2 | 2/2019 | Swayze et al. |
| 10,299,792 B2 | 5/2019 | Huitema et al. |
| 10,349,939 B2 | 7/2019 | Shelton, IV et al. |
| 10,357,252 B2 | 7/2019 | Harris et al. |
| 10,517,593 B2 | 12/2019 | Gupta et al. |
| 10,537,324 B2 | 1/2020 | Shelton, IV et al. |
| 10,542,981 B2 | 1/2020 | Miller et al. |
| 10,561,419 B2 | 2/2020 | Beardsley |
| 10,568,624 B2 | 2/2020 | Shelton, IV et al. |
| 10,588,623 B2 | 3/2020 | Schmid et al. |
| 10,765,427 B2 | 9/2020 | Shelton, IV et al. |
| 10,835,245 B2 | 11/2020 | Swayze et al. |
| 10,898,183 B2 | 1/2021 | Shelton, IV et al. |
| 10,898,191 B2 | 1/2021 | Huitema et al. |
| 10,945,727 B2 | 3/2021 | Shelton, IV et al. |
| 10,952,724 B2 | 3/2021 | Shelton, IV et al. |
| 11,000,278 B2 | 5/2021 | Shelton, IV et al. |
| 11,045,191 B2 | 6/2021 | Shelton, IV et al. |
| 11,058,426 B2 | 7/2021 | Nalagatla et al. |
| D933,220 S | 10/2021 | Tate et al. |
| 11,147,552 B2 | 10/2021 | Burbank et al. |
| 11,207,065 B2 | 12/2021 | Harris et al. |
| 11,229,433 B2 | 1/2022 | Schings et al. |
| 11,234,698 B2 | 2/2022 | Shelton, IV et al. |
| 11,234,700 B2 | 2/2022 | Ragosta et al. |
| 11,291,445 B2 | 4/2022 | Shelton, IV et al. |
| 11,298,129 B2 | 4/2022 | Bakos et al. |
| 11,337,693 B2 | 5/2022 | Hess et al. |
| 11,364,029 B2 | 6/2022 | Burbank et al. |
| 11,382,627 B2 | 7/2022 | Huitema et al. |
| D967,421 S | 10/2022 | Shelton, IV et al. |
| 11,490,890 B2 | 11/2022 | Harris et al. |
| 11,517,315 B2 | 12/2022 | Huitema et al. |
| D974,560 S | 1/2023 | Shelton, IV et al. |
| 11,540,826 B2 | 1/2023 | Nalagatla et al. |
| 11,571,213 B2 | 2/2023 | Huitema et al. |
| 11,589,865 B2 | 2/2023 | Shelton, IV et al. |
| 11,701,114 B2 | 7/2023 | Shelton, IV et al. |
| 11,737,752 B2 | 8/2023 | Schings et al. |
| 11,766,257 B2 | 9/2023 | Shelton, IV et al. |
| 11,826,047 B2 | 11/2023 | Huang et al. |
| 11,849,944 B2 | 12/2023 | Shelton, IV et al. |
| 11,849,947 B2 | 12/2023 | Giordano et al. |
| 11,896,218 B2 | 2/2024 | Bakos et al. |
| 11,974,741 B2 | 5/2024 | Moubarak et al. |
| 2007/0175955 A1 | 8/2007 | Shelton et al. |
| 2014/0001231 A1 | 1/2014 | Shelton, IV et al. |
| 2014/0263552 A1 | 9/2014 | Hall et al. |
| 2015/0134077 A1 | 5/2015 | Shelton, IV et al. |
| 2015/0173756 A1 | 6/2015 | Baxter, III et al. |
| 2018/0132849 A1 | 5/2018 | Miller et al. |
| 2018/0168615 A1 | 6/2018 | Shelton, IV et al. |
| 2019/0059884 A1* | 2/2019 | Shelton, IV ....... A61B 17/1155 |
| 2019/0105047 A1 | 4/2019 | Nalagatla et al. |
| 2019/0200981 A1 | 7/2019 | Harris et al. |
| 2019/0209249 A1 | 7/2019 | Giordano et al. |
| 2021/0196265 A1* | 7/2021 | Shelton, IV ........... A61B 90/98 |
| 2022/0031320 A1 | 2/2022 | Hall et al. |
| 2022/0047256 A1 | 2/2022 | Miller et al. |
| 2022/0047265 A1 | 2/2022 | Miller et al. |
| 2022/0346858 A1 | 11/2022 | Aronhalt et al. |
| 2023/0119119 A1 | 4/2023 | Moubarak |
| 2024/0108336 A1 | 4/2024 | Shelton, IV et al. |

FOREIGN PATENT DOCUMENTS

| | | |
|---|---|---|
| CN | 105997173 A | 10/2016 |
| CN | 106036848 A | 10/2016 |
| CN | 108542454 A | 9/2018 |
| CN | 111195142 A | 5/2020 |

OTHER PUBLICATIONS

U.S. Food and Drug Administration 510(k) Premarket Notification, https://www.accessdata.fda.gov/scripts/cdrh/cfdocs/cfpmn/pmn.cfm?ID=K182476, last update: Jan. 8, 2024, 1 page.

* cited by examiner

ZONED ALGORITHM ADAPTIVE CHANGES BASED ON CORRELATION OF COOPERATIVE COMPRESSION CONTRIBUTIONS OF TISSUE

BACKGROUND

The present disclosure relates to surgical instruments and, in various arrangements, to surgical stapling and cutting instruments and staple cartridges for use therewith that are configured to staple and cut tissue.

SUMMARY

The present disclosure provides a control system that leverages a closure system to reduce the strain on a firing system during a surgical cutting and stapling operation with a surgical stapling and cutting instrument.

A surgical stapling system is disclosed including an end effector, a closure driver, a closure motor, a firing driver, a firing motor, a force sensor, and a control circuit. The end effector comprises a first jaw and a second jaw rotatable relative to the first jaw. The closure driver is movable to rotate the second jaw relative to the first jaw. The closure motor is to drive the closure driver. The firing driver is movable from an unfired position toward a fired position during a firing stroke. The firing motor is to apply a firing force to the firing driver. The force sensor is to sense the firing force applied by the firing motor. The control circuit is coupleable with the closure motor, the firing motor, and the force sensor. The control circuit is to set a firing force threshold, advance the closure driver to a first position, advance the firing driver, monitor the firing force as the firing driver is advanced, compare the firing force to the firing force threshold, and control movement of at least one of the closure driver or the firing driver based on results of the compare and a zone in which the firing driver is positioned.

A surgical stapling system is disclosed including an end effector, a closure driver, a closure motor, a firing driver, a firing motor, and a control circuit. The end effector comprises a first jaw and a second jaw rotatable relative to the first jaw. The second jaw defines a channel. The channel comprises an upper wall comprising a first force sensor and a lower wall comprising a second force sensor. The closure driver is movable to rotate the second jaw relative to the first jaw. The closure motor is to drive the closure driver. The firing driver is movable from an unfired position toward a fired position during a firing stroke. The firing driver comprises a flange to traverse the channel during the firing stroke. The first force sensor is to sense a first force the flange applies to the upper wall. The second force sensor is to sense a second force the flange applies to the lower wall. The firing motor is to apply a firing force to the firing driver. A third force sensor is to sense the firing force applied by the firing motor. The control circuit is coupleable with the closure motor, the firing motor, the first force sensor, the second force sensor, and the third force sensor. The control circuit is to set a firing force threshold, advance the closure driver to a first position, advance the firing driver toward the fired position, monitor the firing force as the firing driver is advanced, compare the firing force to the firing force threshold, determine a clamping state of the second jaw based on results of the compare, and control movement of the closure driver based on results of the determine.

LISTING OF THE FIGURES

Various features of the embodiments described herein, together with advantages thereof, may be understood in accordance with the following description taken in conjunction with the accompanying drawings as follows.

Corresponding reference characters indicate corresponding parts throughout the several views.

DETAILED DESCRIPTION

Figure 1:
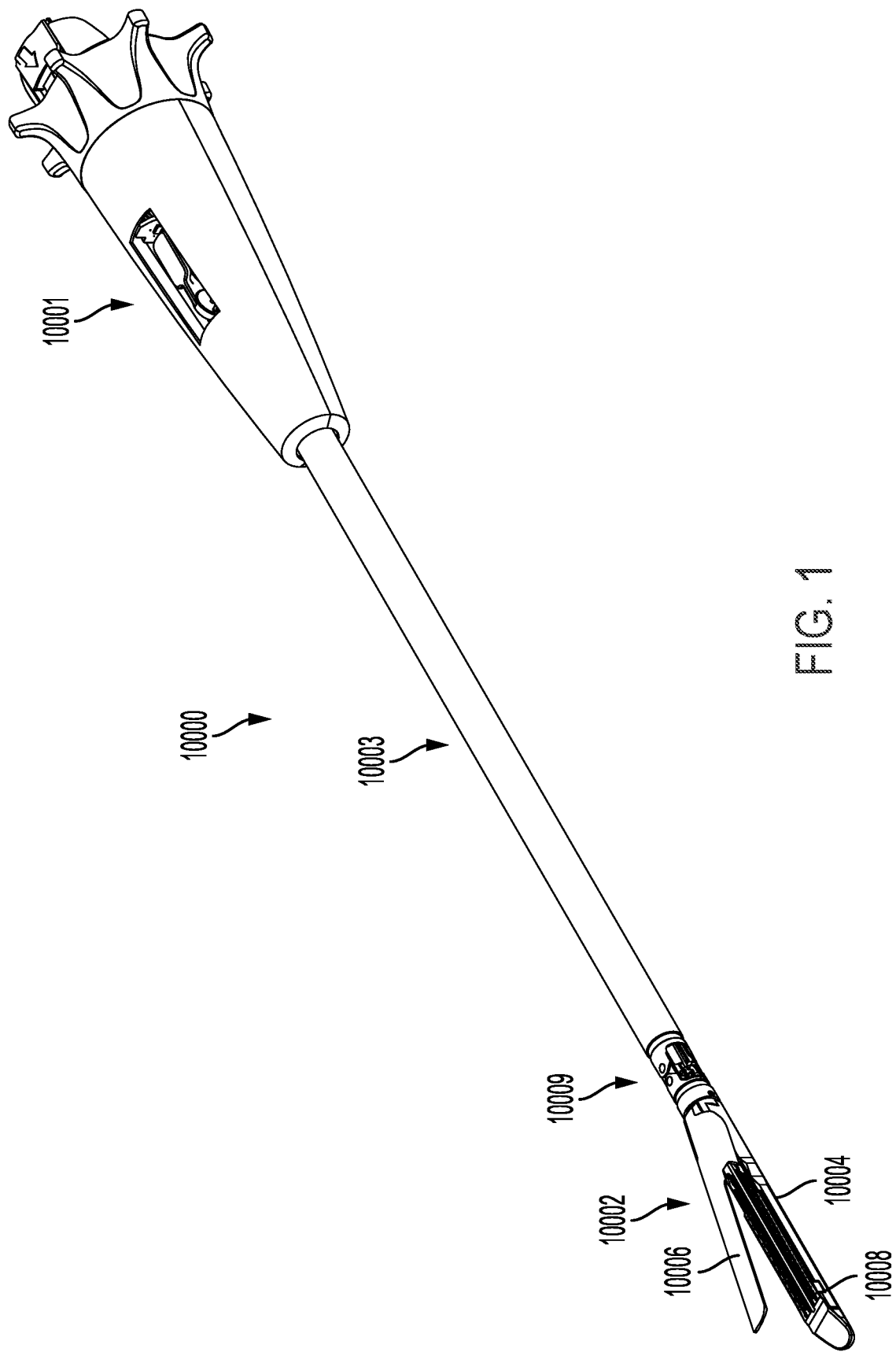
FIG. 1 illustrates a perspective view of a surgical stapling system, in accordance with the present disclosure.

Applicant of the present application owns the following U.S. Patent Applications that were filed on Oct. 13, 2023, and which are each herein incorporated by reference in their respective entireties:

U.S. patent application Ser. No. 18/379,759, titled METHOD OF OPERATING A SURGICAL STAPLING INSTRUMENT;

U.S. patent application Ser. No. 18/379,762, titled SURGICAL STAPLING SYSTEMS WITH ADAPTIVE STAPLE FIRING ALGORITHMS;

U.S. patent application Ser. No. 18/379,763, titled LEARNED TRIGGERS FOR ADAPTIVE CONTROL OF SURGICAL STAPLING SYSTEMS;

U.S. patent application Ser. No. 18/379,766, titled CONTROL CIRCUIT FOR ACTUATING MOTORIZED FUNCTION OF SURGICAL STAPLING INSTRUMENT UTILIZING INERTIAL DRIVE TRAIN PROPERTIES;

U.S. patent application Ser. No. 18/379,768, titled PROPORTIONATE BALANCING OF THE FUNCTION IMPACT MAGNITUDE OF BATTERY OUTPUT TO PEAK MOTOR CURRENT;

U.S. patent application Ser. No. 18/379,771, titled MOTOR OPTIMIZATION BY MINIMIZATION OF PARASITIC LOSSES AND TUNING MOTOR DRIVE CONFIGURATION;

U.S. patent application Ser. No. 18/379,773, titled APPARATUS AND METHOD TO REDUCE PARASITIC LOSSES OF THE ELECTRICAL SYSTEM OF A SURGICAL INSTRUMENT;

U.S. patent application Ser. No. 18/379,776, titled SURGICAL TOOL WITH RELAXED FLEX CIRCUIT ARTICULATION;

U.S. patent application Ser. No. 18/379,777, titled WIRING HARNESS FOR SMART STAPLER WITH MULTI AXIS ARTICULATION;

U.S. patent application Ser. No. 18/379,781, titled SURGICAL SYSTEM WITH WIRELESS ARRAY FOR POWER AND DATA TRANSFER; and U.S. patent application Ser. No. 18/379,784, titled SURGICAL STAPLE CARTRIDGE COMPRISING REPLACEABLE ELECTRONICS PACKAGE.

Applicant of the present application owns the following U.S. Patent Applications that were filed on with Oct. 13, 2023, and which are each herein incorporated by reference in their respective entireties:

U.S. patent application Ser. No. 18/379,790, titled METHOD OF ASSEMBLING A STAPLE CARTRIDGE;

U.S. patent application Ser. No. 18/379,793, titled CONTROL SURFACES ON A STAPLE DRIVER OF A SURGICAL STAPLE CARTRIDGE;

U.S. patent application Ser. No. 18/379,796, titled INTEGRAL CARTRIDGE STIFFENING FEATURES TO REDUCE CARTRIDGE DEFLECTION;

U.S. patent application Ser. No. 18/379,801, titled STAPLE CARTRIDGE COMPRISING WALL STRUCTURES TO REDUCE CARTRIDGE DEFLECTION;

U.S. patent application Ser. No. 18/379,803, titled PANLESS STAPLE CARTRIDGE ASSEMBLY COMPRISING RETENTION FEATURES FOR HOLDING STAPLE DRIVERS AND SLED;

U.S. patent application Ser. No. 18/379,805, titled STAPLE CARTRIDGE COMPRISING A SLED HAVING A DRIVER LIFT CAM;

U.S. patent application Ser. No. 18/379,808, titled SURGICAL STAPLE CARTRIDGES WITH SLEDS CONFIGURED TO BE COUPLED TO A FIRING DRIVER OF A COMPATIBLE SURGICAL STAPLER;

U.S. patent application Ser. No. 18/379,810, titled STAPLE CARTRIDGE COMPRISING A COMPOSITE SLED;

U.S. patent application Ser. No. 18/379,811, titled SURGICAL INSTRUMENTS WITH JAW AND FIRING ACTUATOR LOCKOUT ARRANGEMENTS LOCATED PROXIMAL TO A JAW PIVOT LOCATION;

U.S. patent application Ser. No. 18/379,815, titled SURGICAL INSTRUMENTS WITH LATERALLY ENGAGEABLE LOCKING ARRANGEMENTS FOR LOCKING A FIRING ACTUATOR;

U.S. patent application Ser. No. 18/379,817, titled DUAL INDEPENDENT KEYED LOCKING MEMBERS ACTING ON THE SAME DRIVE MEMBER;

U.S. patent application Ser. No. 18/379,820, titled ADJUNCTS FOR USE WITH SURGICAL STAPLING INSTRUMENTS;

U.S. patent application Ser. No. 18/379,822, titled ADJUNCTS FOR USE WITH SURGICAL STAPLING INSTRUMENTS;

U.S. patent application Ser. No. 18/379,826, titled JAW CONTROL SURFACES ON A SURGICAL INSTRUMENT JAW;

U.S. patent application Ser. No. 18/379,831, titled STAPLE CARTRIDGES COMPRISING TRACE RETENTION FEATURES; and U.S. patent application Ser. No. 18/379,832, titled STAPLE CARTRIDGES COMPRISING STAPLE RETENTION FEATURES.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working frame through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, a staple cartridge may not be removable from, or at least readily replaceable from, the first jaw. The second jaw comprises an anvil configured to deform staples ejected from the staple cartridge. The second jaw is pivotable relative to the first jaw about a closure axis; however, the first jaw may be pivotable relative to the second jaw. The surgical stapling system further comprises an articulation joint configured to permit the end effector to be rotated, or articulated, relative to the shaft. The end effector is rotatable about an articulation axis extending through the articulation joint. However, the surgical stapling system may not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing driver. The firing driver is configured to contact the sled and push the sled toward the distal end. The longitudinal slot defined in the cartridge body is configured to receive the firing driver. The anvil also includes a slot configured to receive the firing driver. The firing driver further comprises a first cam which engages the first jaw and a second cam which engages the second jaw. As the firing driver is advanced distally, the first cam and the second cam can control the distance, or tissue gap, between the deck of the staple cartridge and the anvil. The firing driver also comprises a knife configured to incise the tissue captured intermediate the staple cartridge and the anvil. It is desirable for the knife to be positioned at least partially proximal to the ramped surfaces such that the staples are ejected ahead of the knife.

Figure 2:
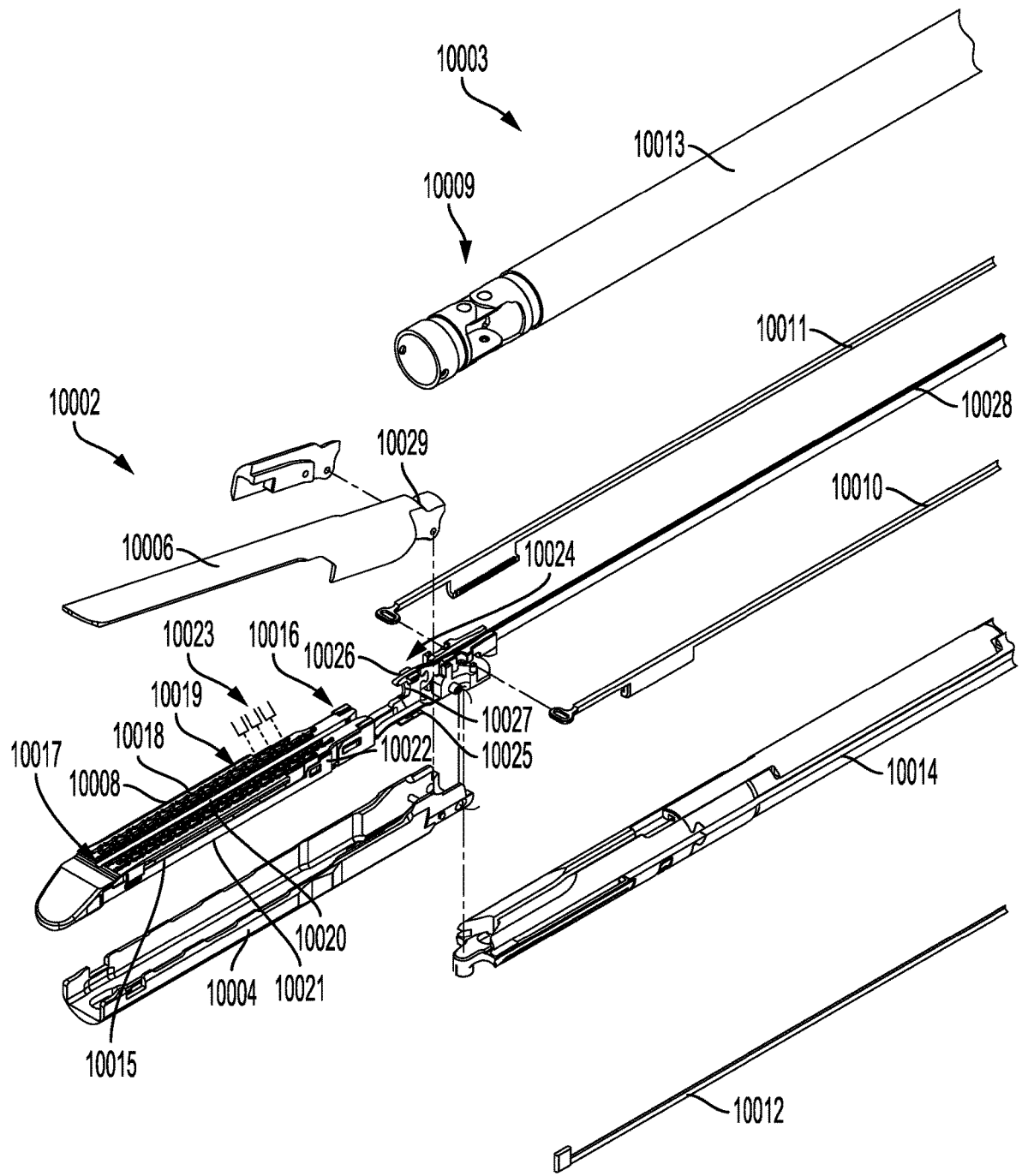
FIG. 2 illustrates an exploded view of the surgical stapling system of FIG. 1, in accordance with the present disclosure.

Referring to FIGS. 1 and 2, a surgical stapling system is provided that comprises a shaft assembly 10000 and an end effector 10002 extending from the shaft assembly 10000. The shaft assembly 10000 comprises an attachment portion 10001 and a shaft 10003 extending distally from the attachment portion 10001. The attachment portion 10001 is configured to be attached to a handle of a surgical instrument and/or the arm of a surgical robot, for example.

The end effector 10002 comprises a first jaw 10004 and a second jaw 10006. The first jaw 10004 comprises a staple cartridge 10008. The staple cartridge 10008 is insertable into and removable from the first jaw 10004; however, a staple cartridge may not be removable from, or at least readily replaceable from, the first jaw 10004. The second jaw 10006 comprises an anvil configured to deform staples ejected from the staple cartridge 10008. The second jaw 10006 is pivotable relative to the first jaw 10004 between an open position, where the tip of the second jaw 10006 is space apart from the first jaw 10004 (see FIG. 1) and a closed position, where the tip of the second jaw 10006 is adjacent the first jaw 10004; however, the first jaw 10004 may be pivotable relative to the second jaw 10006.

The surgical stapling system further comprises an articulation joint 10009 configured to permit the end effector 10002 to be rotated, or articulated, relative to the shaft 10003. The end effector 10002 is rotatable about an articulation axis extending through the articulation joint. However, the surgical stapling system may not include an articulation joint 10009. The shaft assembly 10000 comprises cooperating articulation rods 10010, 10011 (e.g., bars) configured to articulate the end effector 10002 relative to the shaft 10003 about the articulation joint 10009. The shaft assembly 10000 further comprises an articulation lock bar 10012 configured to prevent rotation of the end effector 10002, a closure tube 10013 that houses internal components of the shaft assembly 10000, and a spine portion 10014 configured to provide structure support to the closure tube 10013 and shaft assembly 10000.

The staple cartridge 10008 comprises a cartridge body 10015. The cartridge body 10015 includes a proximal end 10016, a distal end 10017, and a deck 10018 extending between the proximal end 10016 and the distal end 10017. In use, the staple cartridge 10008 is positioned on a first side of the tissue to be stapled and the anvil 10006 is positioned on a second side of the tissue. The anvil 10006 is moved toward the staple cartridge 10008 to compress and clamp the tissue against the deck 10018. Thereafter, staples 10023 removably stored in the cartridge body 10015 can be deployed into the tissue. The cartridge body 10015 includes staple cavities 10019 defined therein wherein staples 10023 are removably stored in each of the staple cavities 10019. The staple cavities 10019 are arranged in six longitudinal rows. Three rows of staple cavities are positioned on a first side of a longitudinal slot 10020 and three rows of staple cavities are positioned on a second side of the longitudinal slot 10020. Other arrangements of staple cavities 10019 and staples 10023 may be possible.

The staples 10023 are supported by staple drivers in the cartridge body 10015. Staples supported on staple drivers can be seen in U.S. Patent Application Publication No. 2021/0059672, which is hereby incorporated by reference in its entirety herein. The drivers are movable between a first, or unfired position, and a second, or fired, position to eject the staples 10023 from the staple cavities 10019. The drivers are retained in the cartridge body 10015 by a retainer 10021 which extends around the bottom of the cartridge body 10015 and includes resilient members 10022 configured to grip the cartridge body 10015 and hold the retainer 10021 to the cartridge body 10015. The drivers are movable between their unfired positions and their fired positions by a sled. The sled is movable between a proximal position adjacent the proximal end 10016 and a distal position adjacent the distal end 10017. The sled comprises a plurality of ramped surfaces configured to slide under the drivers and lift the drivers, and the staples 10023 supported thereon, toward the anvil. The staples may not be supported by staple drivers, but rather, the staples include integral drive surfaces that are directly engaged by the sled to lift the staples, examples of which are described in U.S. Patent Application Publication No. 2015/0173756, which is hereby incorporated by reference in its entirety herein.

Further to the above, the sled is moved distally by a firing driver 10024. The firing driver is configured to contact the sled and push the sled toward the distal end 10017. The longitudinal slot 10020 defined in the cartridge body 10015 is configured to receive the firing driver 10024. The anvil 10006 also includes a slot configured to receive the firing driver 10024. The firing driver 10024 further comprises a first cam 10025 which engages the first jaw 10004 and a second cam 10026 which engages the second jaw 10006. As the firing driver 10024 is advanced distally, the first cam 10025 and the second cam 10026 can control the distance, or tissue gap, between the deck 10018 of the staple cartridge 10008 and the anvil 10006. The firing driver 10024 also comprises a knife 10027 configured to incise the tissue captured intermediate the staple cartridge 10008 and the anvil 10006. It is desirable for the knife 10027 to be positioned at least partially proximal to the ramped surfaces such that the staples 10023 are ejected ahead of the knife 10027. The shaft assembly 10000 further comprises a firing bar 10028 that is attached to the firing driver 10024 and that is configured to drive the firing driver through the staple cartridge 10008. The firing bar 10028 can be comprised a plurality of laminated strips. More details of the shaft assembly 10000 can be found in U.S. patent application Ser. No. 15/385,887 entitled METHOD FOR ATTACHING A SHAFT ASSEMBLY TO A SURGICAL INSTRUMENT AND, ALTERNATIVELY, TO A SURGICAL ROBOT, which is incorporated by reference in its entirety.

The anvil 10006 can be moved from the open position to the closed position using a closure system that is controlled separately from the firing driver 10024. As such, the firing driver 10024 can be considered to be a part of a firing system that is separate and distinctly operable from the closure system. As such, the anvil 10006 can comprise a ramp 10029 on a proximal end thereof and the closure system comprises a closure driver, such the closure tube 10013, that is movable distally to engage the ramp 10029 and cam the anvil 10006 to the closed position. In the closed position, the first cam 10025 and the second cam 10026 of the firing driver 10024 translate distally and maintain the anvil 10006 in the closed position. To transition the anvil 10006 to the open position, the closure driver can be retracted proximal and springs can be positioned within the end effector 10002 to bias the anvil 10006 to the open position. The anvil 10006 may include a tab and the closure driver may define an aperture at the distal end thereof which engages the tab as the closure driver moves proximally, thereby positively transitioning the anvil 10006 to the open position. Exemplary closure systems and closure drivers are described in U.S. Patent Application Publication No. 2021/0059672, which was previously incorporated by reference in its entirety herein.

The anvil 10006 can be moved from the open position to the closed position using the firing driver 10024. As such, the anvil 10006 can include a ramp that extends proximally from the slot defined therein that is engaged by the firing driver 10024 during a first portion of the stroke of the firing driver 10024 to move the anvil 10006 to the closed position. At the end of the first portion of the stroke, the firing driver 10024 can continue advancing distally through a second portion of the stroke to deploy staples from the staple cartridge 10008 and incise tissue captured by the end effector 10002, as described above. Exemplary firing drivers that close the anvil and fire staples are described in U.S. Pat. No. 11,160,551, which was previously incorporated by reference in its entirety herein.

Figure 3:
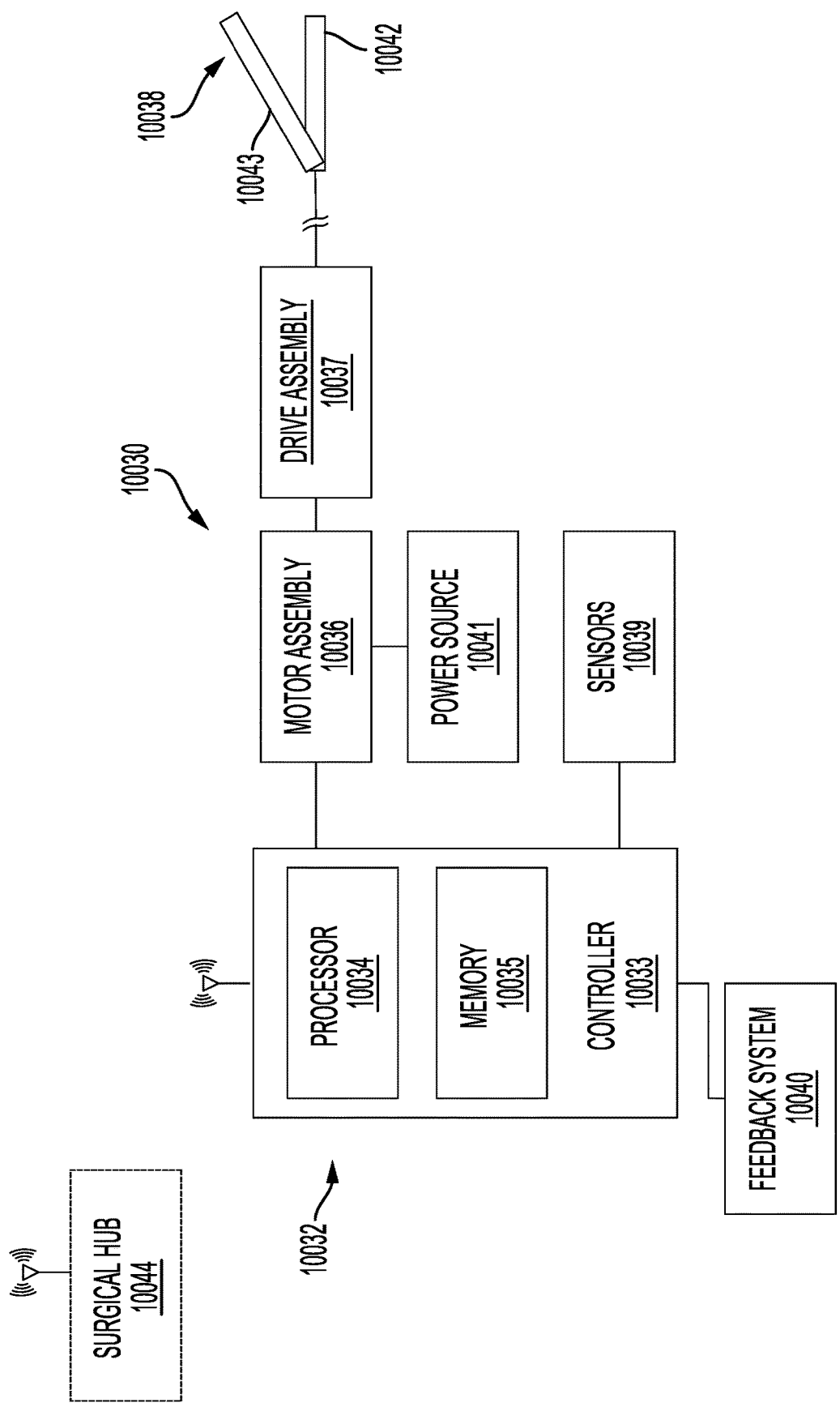
FIG. 3 illustrates a block diagram of a surgical stapling system, in accordance with the present disclosure.

FIG. 3 illustrates a block diagram of a surgical system 10030 for use with one or more surgical instruments, tools, and/or robotic systems in accordance with the present disclosure. The surgical system 10030 includes a control circuit 10032. The control circuit 10032 includes a controller 10033 comprising a processor 10034 and a storage medium such as, for example, a memory 10035.

A motor assembly 10036 includes one or more motors, driven by motor drivers. The motor assembly 10036 operably couples to a drive assembly 10037 to drive, or effect, one or more motions at an end effector 10038, which can be similar to end effector 10002. The drive assembly 10037 may include any number of components suitable for transmitting motion to the end effector 10038 such as, for example, one or more linkages, bars, tubes, and/or cables, for example. The drive assembly 10037 can drive a firing driver and/or a closure driver, described herein above.

One or more of sensors 10039, for example, provide real-time feedback to the processor 10034 about one or more operational parameters monitored during a surgical procedure being performed by the surgical system 10030. The operational parameters can be associated with a user performing the surgical procedure, a tissue being treated, and/or one or more components of the surgical system 10030, for example. The sensor 10039 may comprise any suitable sensor, such as, for example, a magnetic sensor, such as a Hall effect sensor, a strain gauge, a pressure sensor, a position sensor, a force sensor, an inductive sensor, such as an eddy current sensor, a resistive sensor, a capacitive sensor, an optical sensor, and/or any other suitable sensor.

Further to the above, in various arrangements, the sensors 10039 may comprise any suitable sensor for detecting one or more conditions at the end effector 10038 including, without limitation, a tissue thickness sensor such as a Hall Effect Sensor or a reed switch sensor, an optical sensor, a magneto-inductive sensor, a force sensor, a pressure sensor, a piezo-resistive film sensor, an ultrasonic sensor, an eddy current sensor, an accelerometer, a pulse oximetry sensor, a temperature sensor, a sensor configured to detect an electrical characteristic of a tissue path (such as capacitance or resistance), or any combination thereof. As another example, and without limitation, the sensors 10039 may include one or more sensors located at, or about, an articulation joint, similar to articulation joint 10009, extending proximally from the end effector 10038. Such sensors may include, for example, a potentiometer, a capacitive sensor (slide potentiometer), piezo-resistive film sensor, a pressure sensor, a pressure sensor, or any other suitable sensor type. In some arrangements, the sensor 1938 may comprise a plurality of sensors located in multiple locations in the end effector 1940.

The system 1930 can include a feedback system 10040 which includes one or more devices for providing a sensory feedback to a user. Such devices may comprise, for example, visual feedback devices (e.g., an LCD display screen, a touch screen, LED indicators), audio feedback devices (e.g., a speaker, a buzzer) or tactile feedback devices (e.g., haptic actuators).

The controller 10033 may be programmed to perform various functions such as precise control over the speed and position of the drive assembly 10037. The controller 10033 may be any single-core or multicore processor such as those known under the trade name ARM Cortex by Texas Instruments. The main microcontroller 1933 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

The controller 10033 may be configured to compute a response in the software of the controller 10033. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

The motor assembly 10036 includes one or more electric motors and one or more motor drivers. The electric motors can be in the form of a brushed direct current (DC) motor with a gearbox and mechanical links to the drive assembly 10037. A motor driver may be an A3941 available from Allegro Microsystems, Inc.

In various forms, the motor assembly 10036 includes a brushed DC driving motor having a maximum rotational speed of approximately 25,000 RPM. In other arrangements, the motor assembly 10036 may include a brushless motor, a cordless motor, a synchronous motor, a stepper motor, or any other suitable electric motor. The motor driver may comprise an H-bridge driver comprising field-effect transistors (FETs), for example.

The motor assembly 10036 can be powered by a power source 10041. The power source 10041 can include one or more batteries which may include a number of battery cells connected in series that can be used as the power source to power the motor assembly 10036. In certain circumstances, the battery cells of the power assembly may be replaceable and/or rechargeable. In at least one example, the battery cells can be lithium-ion batteries which can be couplable to and separable from the power assembly.

Further to the above, the end effector 10038 includes a first jaw 10042 and a second jaw 10043. At least one of the first jaw 10042 and the second jaw 10043 is rotatable relative to the other during a closure motion that transitions the end effector 10038 from an open configuration toward a closed configuration. The closure motion may cause the jaws 10042, 10043 to grasp tissue therebetween. In certain arrangements, sensors, such as, for example, a strain gauge or a micro-strain gauge, are configured to measure one or more parameters of the end effector 10038, such as, for example, the amplitude of the strain exerted on the one or both of the jaws 10042, 10043 during a closure motion, which can be indicative of the closure forces applied to the jaws 10042, 10043. The measured strain is converted to a digital signal and provided to the processor 10034, for example. Alternatively, additionally, sensors such as, for example, a load sensor, can measure a closure force and/or a firing force applied to the jaws 10042, 10043. The sensors can comprise a first sensor that measures a first force on a firing driver, such as firing driver 10024, during a firing stroke and a second sensor that measures a second force on a closure driver, such as the closure tube 10013, during a closure stroke. The processor 10034 can receive these force readings and determine a relationship therebetween, as described in more detail herein below. For instance, the processor 10034 can determine a distribution of force (a ratio) of the force exerted on the firing driver and the closure driver.

In various arrangements, a current sensor can be employed to measure the current drawn by a motor of the motor assembly 10036. The force required to advance the drive assembly 10037 can correspond to the current drawn by the motor, for example. The measured force is converted to a digital signal and provided to the processor 10034.

In one form, strain gauge sensors can be used to measure the force applied to the tissue by the end effector 10038, for example. A strain gauge can be coupled to the end effector 10038 to measure the force on the tissue being treated by the end effector 10038. The strain gauge sensors can measure the amplitude or magnitude of the strain exerted on a jaw of an end effector 10038 during a closure motion which can be indicative of the tissue compression. The measured strain is converted to a digital signal and provided to a processor 10034.

The measurements of the tissue compression, the tissue thickness, and/or the force required to close the end effector on the tissue, as respectively measured by the sensors 10039 can be used by the controller 10033 to characterize the selected position of one or more components of the drive assembly 10037 and/or the corresponding value of the speed of one or more components of the drive assembly 10037. A memory (e.g. memory 10035) may store a technique, an equation, and/or a lookup table which can be employed by the microcontroller 1933 in the assessment.

The surgical system 10030 may comprise wired or wireless communication circuits to communicate with surgical hubs (e.g. surgical hub 10044), communication hubs, and/or robotic surgical hubs, for example. Additional details about suitable interactions between a surgical system 10030 and the surgical hub 10044 are disclosed in U.S. patent application Ser. No. 16/209,423 entitled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981, the entire disclosure of which is incorporated by reference in its entirety herein.

The control circuit 10032 can be configured to implement various processes described herein. The control circuit 10032 may comprise a microcontroller comprising one or more processors (e.g., microprocessor, microcontroller) coupled to at least one memory circuit. The memory circuit stores machine-executable instructions that, when executed by the processor, cause the processor to execute machine instructions to implement various processes described herein. The processor may be any one of a number of single-core or multicore processors known in the art. The memory circuit may comprise volatile and non-volatile storage media. The processor may include an instruction processing unit and an arithmetic unit. The instruction processing unit may be configured to receive instructions from the memory circuit of this disclosure.

Alternatively, the control circuit 10032 can be in the form of a combinational logic circuit configured to implement various processes described herein. The combinational logic circuit may comprise a finite state machine comprising a combinational logic configured to receive data, process the data by the combinational logic, and provide an output.

Alternatively, the control circuit 10032 can be in the form of a sequential logic circuit. The sequential logic circuit can be configured to implement various processes described herein. The sequential logic circuit may comprise a finite state machine. The sequential logic circuit may comprise a combinational logic, at least one memory circuit, and a clock, for example. The at least one memory circuit can store a current state of the finite state machine. The sequential logic circuit may be synchronous or asynchronous. The control circuit 10032 may comprise a combination of a processor (e.g., processor 10034) and a finite state machine to implement various processes herein. The finite state machine may comprise a combination of a combinational logic circuit (and the sequential logic circuit, for example.

Figure 4:
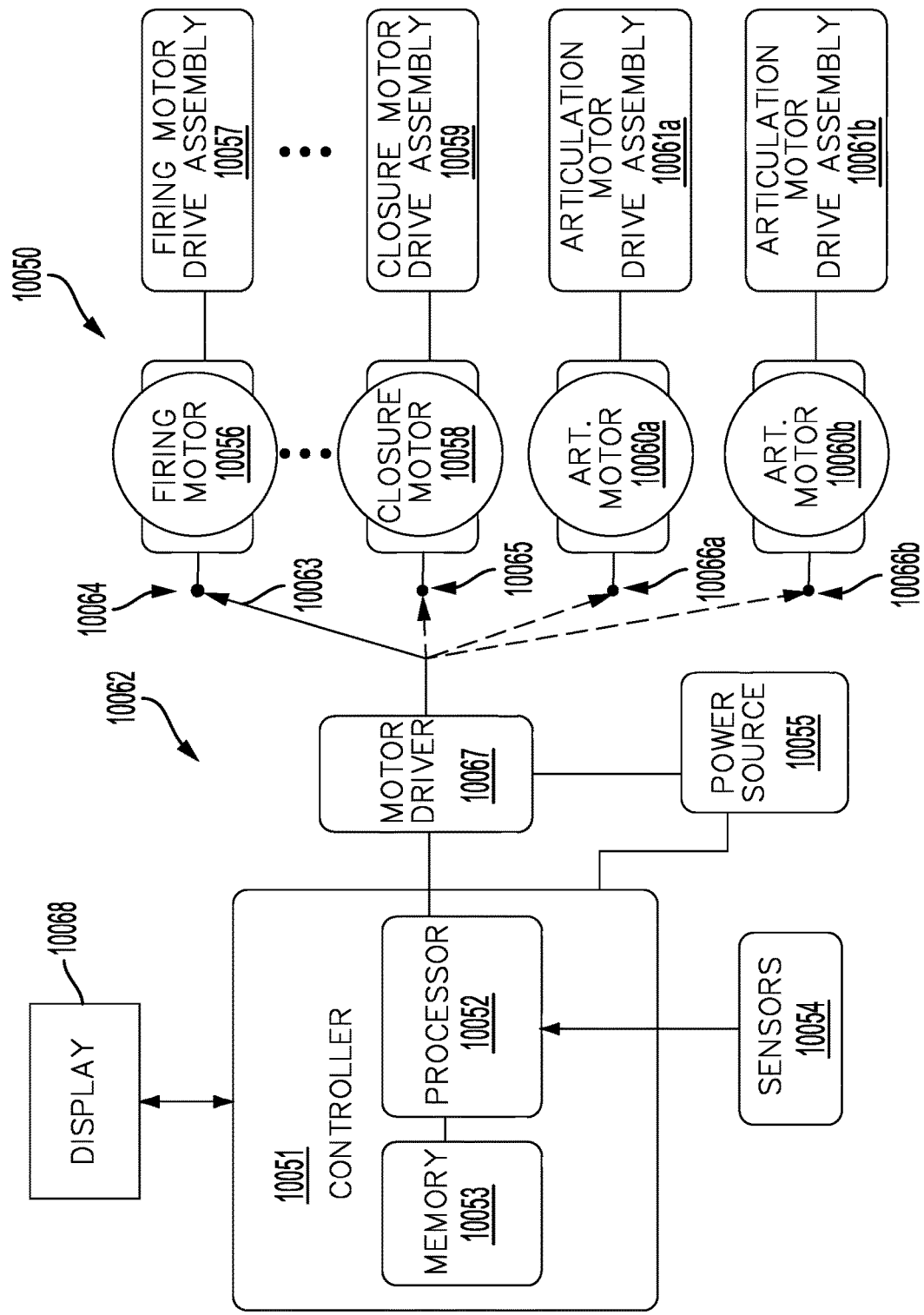
FIG. 4 illustrates a block diagram of a surgical stapling system, in accordance with the present disclosure.

FIG. 4 illustrates a block diagram of a surgical system 10050 for use with one or more surgical instruments, tools, and/or robotic systems in accordance with the present disclosure. The surgical system 10050 is similar in many respects to the surgical system 10030, which are not repeated herein at the same of detail for brevity. For example, like the surgical system 10030, the surgical system 10050 includes a control circuit comprising a controller 10051 comprising a processor 10052 and a memory 10053, sensors 10054, and a power source 10055, which are similar, respectively, to the controller 10033 (e.g., microcontroller), the processor 10034, the memory 10035, and the power source 10041. Additionally, the surgical system 10050 includes a plurality of motors and corresponding driving assemblies that can be activated to perform various functions.

A first motor can be activated to perform a first function, a second motor can be activated to perform a second function, a third motor can be activated to perform a third function, a fourth motor can be activated to perform a fourth function, and so on. The plurality of motors can be individually activated to cause firing, closure, and/or articulation motions in an end effector, such as end effector 10002 or end effector 10038, as examples. The firing, closure, and/or articulation motions can be transmitted to the end effector through a shaft assembly, such as shaft assembly 10000, for example.

The surgical system 10050 may include a firing motor 10056. The firing motor 10056 may be operably coupled to a firing motor drive assembly 10057 which can be configured to transmit firing motions, generated by the motor 10056 to the end effector, such as displacement of the firing bar 10028 and firing driver 10024. The firing motions generated by the motor 10056 may cause the staples to be deployed from a staple cartridge, such as staple cartridge 10008, into tissue captured by the end effector and/or the knife of a firing driver, such as knife 10027, to be advanced to cut the captured tissue, for example. The firing driver may be retracted by reversing the direction of the motor 10056.

The surgical system 10050 may include a closure motor 10058. The closure motor 10058 may be operably coupled to a closure motor drive assembly 10059 which can be configured to transmit closure motions, generated by the motor 10058 to the end effector, in particular to displace a closure driver, such as outer shaft tube, to close an anvil and compress tissue between the anvil and the staple cartridge. The closure motions may cause the end effector to transition from an open configuration to an approximated, or closed, configuration to grasp tissue, for example. The end effector may be transitioned to an open position by reversing the direction of the motor 10058.

The surgical system 10050 may include one or more articulation motors 10060a, 10060b, for example. The motors 10060a, 10060b may be operably coupled to respective articulation motor drive assemblies 10061a, 10061b, which can be configured to transmit articulation motions generated by the motors 10060a, 10060b to the end effector. The articulation motions may cause the end effector to articulate relative to a shaft, for example. The first articulation motor 10060a can drive a first articulation bar, such as articulation rod 10010, to rotate the end effector in a first direction and the second articulation motor 10060b drive a second articulation bar, such as articulation rod 10011, to rotate the end effector in a second direction opposite the first direction.

As described above, the surgical system 10050 may include a plurality of motors which may be configured to perform various independent functions. The plurality of motors of the surgical instrument or tool can be individually or separately activated to perform one or more functions while the other motors remain inactive. For example, the articulation motors 10060a, 10060b can be activated to cause the end effector to be articulated while the firing motor 10056 remains inactive. Alternatively, the firing motor 10056 can be activated to fire the plurality of staples, and/or to advance the cutting edge, while the articulation motors 10060a, 10060b remains inactive. Furthermore, the closure motor 10058 may be activated simultaneously with the firing motor 10056 to cause the closure driver and the firing driver to advance distally at the same time, or in an overlapping fashion, as described in more detail hereinbelow.

The surgical system 10050 may include a common control module 10062 which can be employed with a plurality of motors of the surgical instrument or tool. The common control module 10062 may accommodate one of the plurality of motors at a time. For example, the common control module 10062 can be couplable to and separable from the plurality of motors of the robotic surgical instrument individually. A plurality of the motors of the surgical instrument or tool may share one or more common control modules such as the common control module 10062. A plurality of motors of the surgical instrument or tool can be individually and selectively engaged with the common control module 10062. The common control module 10062 can be selectively switched from interfacing with one of a plurality of motors of the surgical instrument or tool to interfacing with another one of the plurality of motors of the surgical instrument or tool.

The common control module 10062 can be selectively switched between operable engagement with the articulation motors 10060a, 10060b and operable engagement with either the firing motor 10056 or the closure motor 10058. As illustrated in FIG. 4, a switch 10063 can be moved or transitioned between a plurality of positions and/or states. In a first position 10064, the switch 10063 may electrically couple the common control module 10062 to the firing motor 10056; in a second position 10065, the switch 10063 may electrically couple the common control module 10062 to the closure motor 10058; in a third position 10066a, the switch 10063 may electrically couple the common control module 10062 to the first articulation motor 10060a; and in a fourth position 10066b, the switch 10063 may electrically couple the common control module 10062 to the second articulation motor 10060b, for example. Separate common control modules 10062 can be electrically coupled to the firing motor 10056, the closure motor 10058, and the articulations motor 10060a, 10060b at the same time. The switch 10063 may be a mechanical switch, an electromechanical switch, a solid-state switch, or any suitable switching mechanism.

Each of the motors 10056, 10058, 10060a, 10060b may comprise a torque sensor to measure the output torque on the shaft of the motor. The force on an end effector may be sensed in any conventional manner, such as by force sensors on the outer sides of the jaws or by a torque sensor for the motor actuating the jaws.

As illustrated in FIG. 4, the common control module 10062 may comprise a motor driver 10067 which may comprise one or more H-Bridge FETs. The motor driver 10067 may modulate the power transmitted from a power source 10055 to a motor coupled to the common control module 10062 based on input from a controller 10051 (e.g., microcontroller)), for example. The controller 10051 can be employed to determine the current drawn by the motor, for example, while the motor is coupled to the common control module 10062, as described above.

The processor 10052 may control the motor driver 10067 to control the position, direction of rotation, and/or velocity of a motor that is coupled to the common control module 10062. The processor 10052 can signal the motor driver 10067 to stop and/or disable a motor that is coupled to the common control module 10062.

The memory 10053 may include program instructions for controlling each of the motors of the surgical system 10050 that are couplable to the common control module 10062. For example, the memory 10053 may include program instructions for controlling the firing motor 10056, the closure motor 10058, and the articulation motors 10060a, 10060b. Such program instructions may cause the processor 10052 to control the firing, closure, and articulation functions in accordance with inputs from algorithms or control programs of the surgical instrument or tool.

One or more mechanisms and/or sensors such as, for example, sensors 10054 can be employed to alert the processor 10052 to the program instructions that should be used in a particular setting. For example, the sensors 10054 may alert the processor 10052 to use the program instructions associated with firing, closing, and articulating the end effector. The sensors 10054 may comprise position sensors which can be employed to sense the position of the switch 10063, for example. Accordingly, the processor 10052 may use the program instructions associated with firing the I-beam of the end effector upon detecting, through the sensors 10054 for example, that the switch 10063 is in the first position 10064; the processor 10052 may use the program instructions associated with closing the anvil upon detecting, through the sensors 10054 for example, that the switch 10063 is in the second position 10065; and the processor 10052 may use the program instructions associated with articulating the end effector upon detecting, through the sensors 10054 for example, that the switch 10063 is in the third or fourth position 10066a, 10066b. The controller 10051 can communicate with a display 10068, which can be similar to feedback system 10040, to provide feedback to a user. In addition, the display 625 can include an input interface such that a user can provide input for controlling the surgical system 10050.

Closure systems that utilize position control closure are plagued by operating in a manner where a closure stoke of a closure driver produces a specific force to tissue captured within the end effector after the end effector has been placed into a closed position. As the tissue thins due to tissue creep and fluid egressing away from the captured tissue, this specific force applied to the tissue diminishes over time. For example, a closure system utilizing position control closure transitions the end effector from an open state toward a closed state by a closure driver which causes a gradual increase in the closure force applied to the tissue. Once the closure driver reaches the end of its closure stroke, the closure force reaches a maximum closure force.

A problem with these closure systems is that, once they have completed their closure stroke, the force applied to the tissue drops over time (due to fluid egress and eventual tissue thinning, for example). As a result of the diminishing closure force after reaching the maximum closure force, the force to drive the firing system reaches a firing force that is greater than the maximum closure force, which places a lot of stress on the firing motor of the firing system.

The load control of the closure system can enable the closure load, and therefore, the closure force, to stay at an elevated level, improving the pre-firing compression of the tissue, and ultimately, resulting in lower forces to fire. Accordingly, load control allows the surgical system to balance the mechanical firing force impacts between the closure system and the firing system in order to reduce stress on the corresponding drive systems and motors, in particular, the stress on the firing system and the firing motor.

Figure 5:
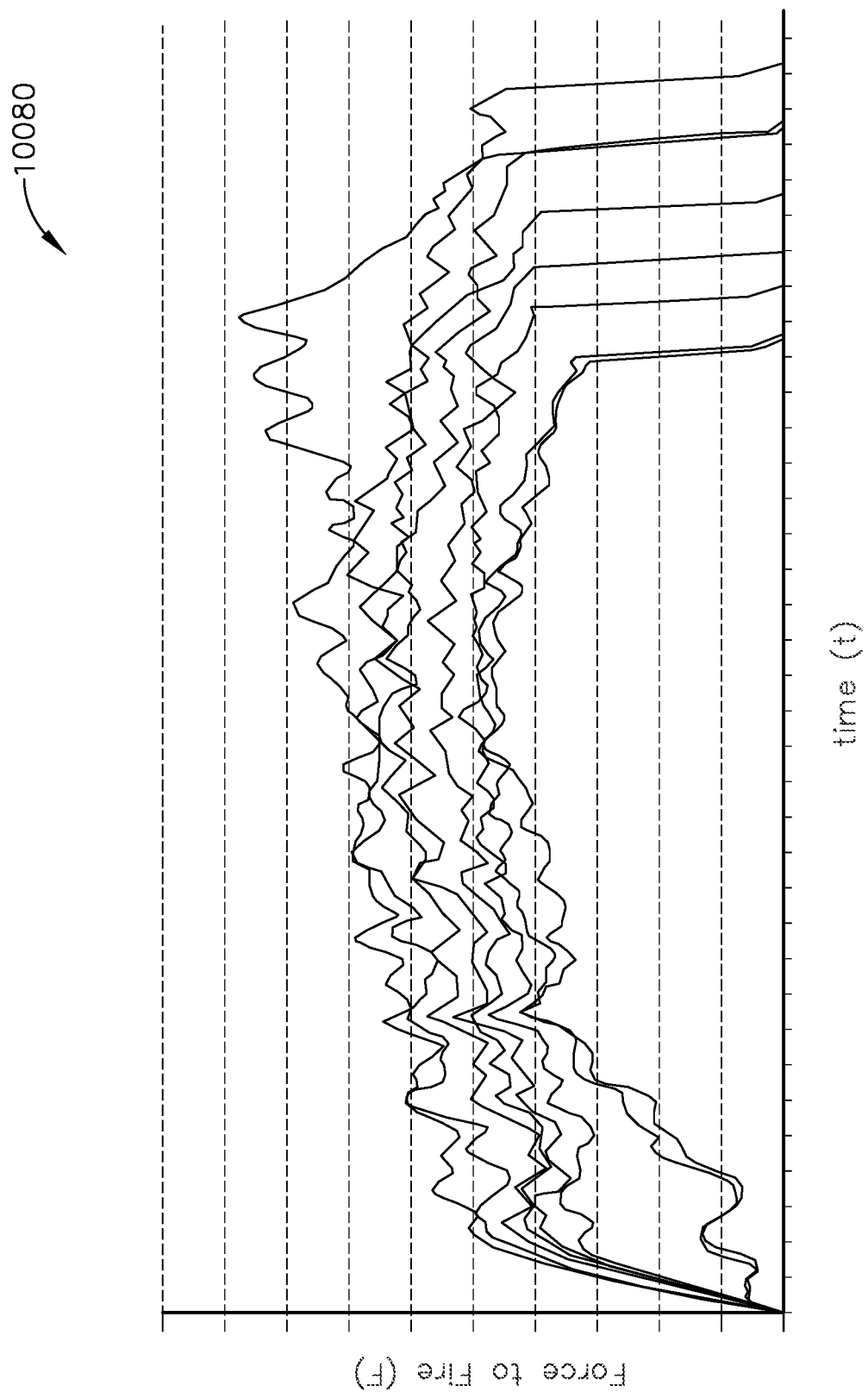
FIG. 5 is a graph that illustrates the relationship between firing force over time for various firing strokes of firing drivers.

Referring to FIG. 5, a graph 10080 is provided that illustrates the relationship between firing force over time for various firing strokes of firing drivers. As shown, the firing force increases over the course of the firing stroke. The inventors have found that maximization of the closure system can supplement the firing system and enable the firing force to be significantly lowered during a portion of the firing stroke. The portion of the firing stroke can be the first third of the firing stroke. While utilization of the closure system impacts the firing force throughout the entire stroke of the firing driver, the stiffness of the anvil and the deflections of the anvil lends to an outsized impact in the first portion of the stroke over the remaining portion of the stroke. However, utilization of the closure system over the entire stroke of the firing system can provide the benefit of reducing the force requirement on the firing system, even over the remaining portion of the stroke.

A surgical system can be provided that includes a closure system and a firing system. The closure system includes a closure driver, such as closure tube 10013, that is movable from a proximal position toward a distal position during a closure stroke. The closure driver is driven between the proximal position and the distal position by a closure motor, such as closure motor 10058; however, the closure driver may be driven between the proximal position and the distal position by a manual-drive system that includes a closure trigger manually operable by a clinician. The surgical system further comprises an end effector, such as end effector 10002, that includes a first jaw, such as first jaw 10004, and a second jaw, such as second jaw 10006, that is rotatable relative to the first jaw between an open position and a closed position. In use, the closure driver translates toward the distal position and engages the second jaw, such as on a ramp on the proximal end thereof. The closure driver applies a closure force to the second jaw to rotate the second jaw toward the closed position. The surgical system can further include a first closure force sensor that senses the closure force applied to the second jaw by the closure driver.

The firing system includes a firing driver, such as firing driver 10024, that is movable from a proximal, unfired position toward a distal, fired position during a firing stroke to deploy staples stored in a staple cartridge, such as staple cartridge 10008, and to incise tissue captured by the end effector with a knife, such as knife 10027. The firing driver is driven between the proximal, unfired position and the distal, fired position by a firing motor, such as firing motor 10056. The firing driver includes a first cam, such as first cam 10025, and a second cam, such as second cam 10026, that engage the first jaw and the second jaw, respectively, during the firing stroke to apply a closure force to the end effector to maintain the second jaw in the closed position. The surgical system can further include a second closure force sensor that senses the closure force applied to the end effector by the firing driver.

The surgical system further includes a control system, such as controller 10033 or controller 10051, as examples. The control system determines a relationship between the closure system and the firing system, in order to determine which of the closure driver and/or the firing driver the control system should control during the firing stroke of the firing driver, as described in more detail below. Determining a relationship between the closure driver and the firing driver can comprise determining an amount of co-operation that exists between the closure driver and the firing driver in maintaining the second jaw in the closed position during the firing stroke. The control system can receive data from the first closure force sensor and the second closure force sensor to determine the amount of co-operation that exists between the closure system and the firing system. The surgical system can further include various other sensors that sense various other parameters associated with the closure system and the firing system, as described elsewhere herein, that are also used as inputs for determining the amount of co-operation that exists between the closure system and the firing system. For instance, the control system can receive data from position sensors that sense a position of the closure driver and the firing driver and can utilize this data to determine an amount of co-operation that exists between the closure system and the firing system.

The control system can determine an amount of co-operation between the closure driver and the firing driver by determining a ratio of the closure force that each of the respective members applies during the firing stroke of the firing driver. The amount of co-operation between the closure driver and the firing driver may be a ratio of a first parameter of the closure system measured by a first sensor with a second parameter of the firing system measured by a second sensor.

When the force sensed by the first closure force sensor and the second closure force sensor is identical (a 1-to-1 ratio), the control system determines that a 100% co-operation exists between the closure system and the firing system. This can indicate that the closure motor and the firing motor are experiencing the same, or similar, strains during operation thereof. When the force sensed by the second force sensor is twice as much as the force sensed by the first force sensor (a 1-to-2 ratio, indicating that the firing driver is applying twice as much closure force as the closure driver), the control system determines that a 50% co-operation exists between the closure system and the firing system. When the force sensed by the first force sensor is more than the force sensed by the second force sensor (i.e., the closure driver is applying a greater closure force than the firing driver), the control system interprets this a 100% co-operation existing between the closure system and the firing system. Stated another way, the control system recognizes a 100% co-operation between the closure system and the firing system until the closure force applied by the firing driver exceeds the closure force applied by the closure driver.

Based on the amount of co-operation that exists between the closure system and the firing system, the control system makes adjustments to the closure system and/or the firing system. As described in more detail below, the control system can adjust the firing force threshold of the firing system. The control system can make adjustments to the closure algorithm that drives the closure driver and/or the firing algorithm that drives the firing driver. This can alleviate strain experienced by each of respective systems, while also lowering the force to fire the firing driver.

Figures 6, 7:
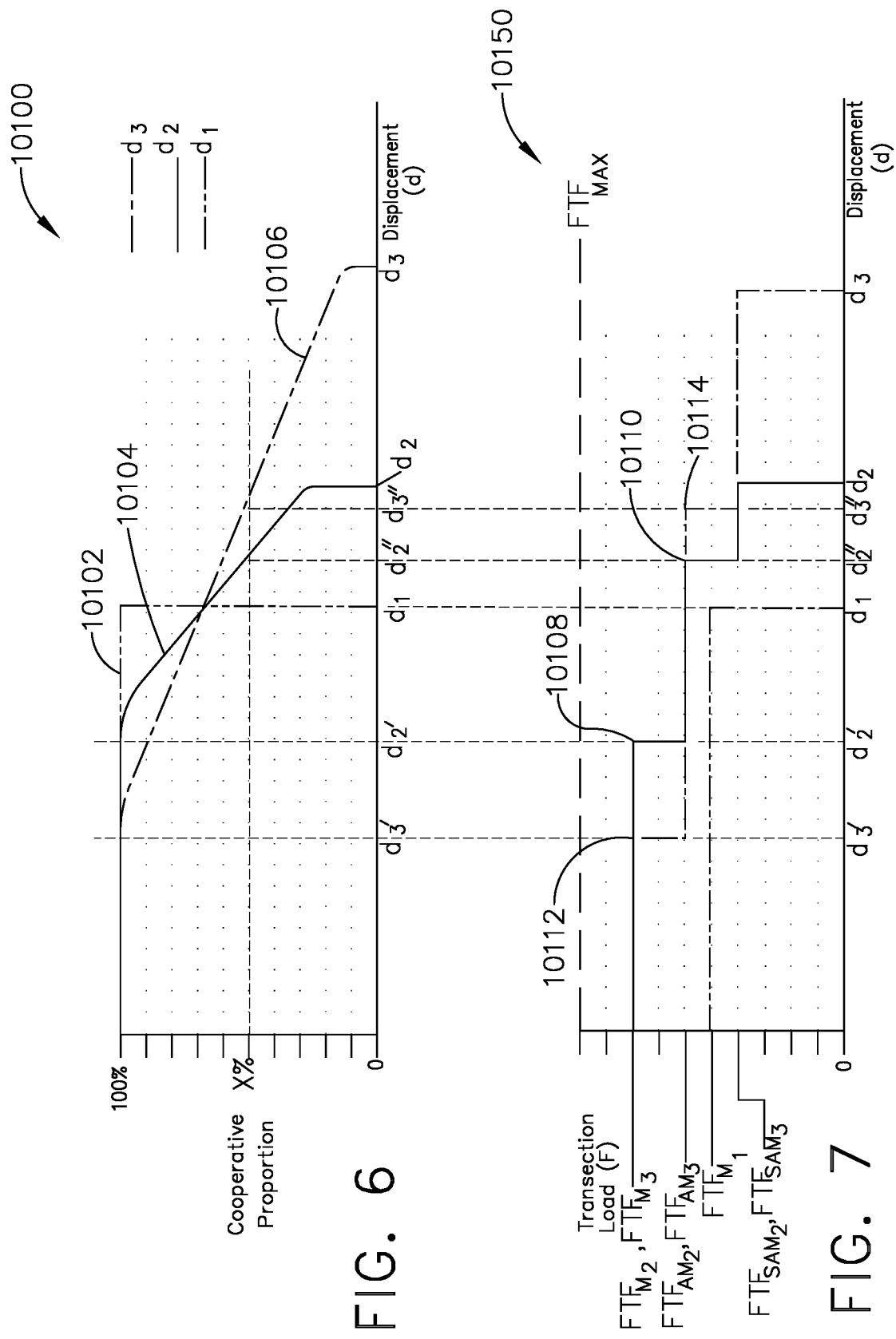
FIG. 6 is a graph that illustrates exemplary firing strokes of a firing driver for various sizes of staple cartridges and the amount of co-operation that exists between a closure system and a firing system over the firing stroke of the firing driver.
FIG. 7 is a graph that illustrates firing force thresholds for each of the respective exemplary staple cartridges of FIG. 6 over the firing stroke of the firing driver.

Referring now to FIG. 6, a graph 10100 is provided that illustrates exemplary firing strokes of a firing driver for various sizes of staple cartridges (lengths $d_1$, $d_2$, and $d_3$, where $d_2 > d_1$ and $d_3 > d_2$) and the amount of co-operation that exists between the closure system and the firing system over the firing stroke of the firing driver.

Furthermore, FIG. 7 illustrates a graph 10150 that includes firing force thresholds for each of the respective exemplary staple cartridges over the firing stroke of the firing driver. As seen in FIG. 7, the initial firing force thresholds $FTF_{M1}$ (initial firing force threshold for staple cartridge with length $d_1$), $FTF_{M2}$ (initial firing force threshold for staple cartridge with length $d_2$), and $FTF_{M3}$ (initial firing force threshold for staple cartridge with length $d_3$) are less than a maximum firing force threshold $FTF_{MAX}$ that would result in the firing motor, such as firing motor 10056, stalling. The initial firing force threshold for the staple cartridges can be at the maximum firing force threshold $FTF_{MAX}$. The staple cartridges can include an RFID tag positioned thereon and the control system includes an RFID scanner that scans that RFID tag to determine a type of staple cartridge that has been inserted into the end effector. RFID tags and RFID scanners are discussed in more detail in U.S. Patent Application Publication No. 2017/0296173, which is hereby incorporated by reference in its entirety herein. Based on the determination, the control system retrieves the initial firing force threshold stored in a memory, such as memory 10035 or memory 10053. The initial firing force threshold can be set by a user. For instance, a user can input the initial firing force threshold at an input interface, such as at the display 10068.

Based on the amount of co-operation that exists between the closure system and the firing system, the control system adjusts the firing force threshold during the firing stroke of the firing driver. For example, with reference to graphs 10100, 10150, a staple cartridge with a length $d_1$ is inserted into the first jaw of the end effector. Based on the insertion, an initial firing force threshold $FTF_{M1}$ is set, as discussed above. The end effector is then utilized to grasp tissue within the jaws of the end effector. In particular, the closure driver is advanced distally by the closure motor to apply a closure force to the second jaw to transition the second jaw toward the closed position. The closure driver can be at a first position intermediate the proximal position and the distal position when the second jaw has reached the closed position. The closure driver can halt advancement toward the distal position once a threshold amount of force has been applied to the tissue by the second jaw, thus preventing the tissue from being damaged. As such, the second jaw is in a position intermediate the open position and the closed position (i.e., a partially closed or partially open position) when the closure driver halts advancement.

Once the closure driver stops advancing, the firing system advances the firing driver through its firing stroke 10102 to deploy staples from the staple cartridge and cut the tissue captured by the end effector. An amount of time can elapse between the closure driver halting and the firing system initiating to allow for pre-compression of the tissue, which is described in more detail in U.S. patent application Ser. No. 17/957,946, which is hereby incorporated by reference in its entirety herein. As the firing driver is advanced through its firing stroke 10102, the first cam and the second cam of the firing driver apply a closure force to the jaws of the end effector to maintain the end effector in the closed position.

As the firing driver is advanced toward the distal position, the control system monitors an amount of force applied to the end effector by the closure driver (via the first force sensor) and the firing driver (via the second force sensor) and determines an amount of co-operation that exists between the closure system and firing system to maintain the end effector in the closed position. As shown in FIG. 6, the amount of co-operation between the closure system and the firing system is determined by the control system to be at, or substantially at, 100% throughout the entire firing stroke 10102 of the firing driver. With a co-operation of 100%, the firing driver is considered to be in a first firing zone. As the amount of co-operation does not drop below 100%, the control system does not adjust the initial firing force threshold $FTF_{M1}$ during the firing stroke 10102.

As another example, a staple cartridge with a length $d_2$ is inserted into the first jaw of the end effector. Based on the insertion, an initial firing force threshold $FTF_{M2}$ is set, as discussed above. As seen in graph 10150, the initial firing force threshold $FTF_{M2}$ is greater for the staple cartridge with a length $d_2$ than the initial firing force threshold $FTF_{M1}$ for the staple cartridge with the length $d_1$. The initial firing force threshold can be the same regardless of the size of the staple cartridge. Alternatively, the initial firing force threshold for a staple cartridge having a first length can be greater than the initial firing force threshold for a staple cartridge having a second length less than the first length. The initial firing force threshold can be a function of the length of the staple cartridge. As referenced above, the initial firing force threshold can be stored in a memory and retrieved by the control system. The initial firing force threshold can be set by a user.

The end effector is then utilized to grasp tissue within the jaws of the end effector. In particular, the closure driver is advanced distally to apply a closure force to the second jaw to transition the second jaw toward the closed position. The closure driver can be at a first position intermediate the proximal position and the distal position when the second jaw has reached the closed position. The closure driver can halt advancement toward the distal position once a threshold amount of force has been applied to the tissue by the second jaw, thus preventing the tissue from being damaged. As such, the second jaw is in a position intermediate the open position and the closed position (i.e., a partially closed or partially open position) when the closure driver halts advancement.

Once the closure driver stops advancing, the firing system advances the firing driver through its firing stroke 10104 to deploy staples from the staple cartridge and cut the tissue captured by the end effector. As described above, an amount of time can elapse between the closure driver halting and the firing system initiating to allow for pre-compression of the tissue. As the firing driver is advanced through its firing stroke 10104, the first cam and the second cam of the firing driver apply a closure force to the jaws of the end effector to maintain the end effector in the closed position.

As the firing driver is advanced toward the distal position, the control system monitors an amount of force applied to the end effector by the closure driver (via the first force sensor) and the firing driver (via the second force sensor) and determines an amount of co-operation that exists between the closure system and the firing system to maintain the end effector in the closed position. As shown in FIG. 6, the amount of co-operation between the closure system and the firing system is determined by the control system to be at, or substantially at, 100% until the firing driver reaches a length $d_2'$ of its firing stroke 10104. From the initiation of the firing stroke until $d_2'$, with a co-operation of 100%, the firing driver is considered to be in a first firing zone.

At $d_2'$, the amount of closure force applied by the firing driver begins to exceed the amount of closure force applied by the closure driver. Therefore, the control system (via the first and second force sensors) determines the amount of co-operation begins to drop below 100%, and therefore, the firing driver transitions to a second firing zone. As discussed above, the control system adjusts the firing force threshold during the firing stroke based on the amount of co-operation that exists between the closure system and the firing system. Accordingly, in the second firing zone, the control system adjusts 10108 the initial firing force threshold $FTF_{M2}$ to a first adjusted firing force threshold $FTF_{AM2}$ that is less than the initial firing force threshold $FTF_{M2}$. The first adjusted firing force threshold $FTF_{AM2}$ can be stored in a memory and retrieved by the control system. The first adjusted firing force threshold $FTF_{AM2}$ can be user defined. The firing driver can transition to the second firing zone when the amount of co-operation drops below 100%. The firing driver can transition to the second firing zone when the amount of co-operation drops a threshold amount below 100% co-operation.

As shown in graph 10100, the firing driver continues to advance through its firing stroke 10104 in the second firing zone and the amount of co-operation continues to diminish. At $d_2''$, the amount of co-operation reaches a threshold co-operation percentage X %, and therefore, the firing driver transitions to a third firing zone. The threshold co-operation percentage may be 50% co-operation (a 1-to-2 ratio). The threshold co-operation percentage may be 75% (a 3-to-4 ratio). The threshold co-operation percentage may be 25% (a 1-to-4 ratio). The threshold co-operation percentage can be stored in a memory and retrieved by the control system. The threshold co-operation percentage can be user defined. The threshold co-operation percentage can be set based on the insertion of the staple cartridge into the end effector.

Based on the firing driver transitioning to the third firing zone, the control system adjusts 10110 the first adjusted firing force threshold $FTF_{AM2}$ to a second adjusted firing force threshold $FTF_{SAM2}$ that is less than the first adjusted firing force threshold $FTF_{AM2}$. The second adjusted firing force threshold $FTF_{SAM2}$ can be stored in a memory and retrieved by the control system. The second adjusted firing force threshold $FTF_{SAM2}$ can be user defined. After the control system adjusts the first adjusted firing force threshold $FTF_{AM2}$ to the second adjusted firing force threshold $FTF_{SAM2}$, the firing driver continues to advance through the remainder of the firing stroke 10104.

As another example, a staple cartridge with a length $d_3$ is inserted into the first jaw of the end effector. Based on the insertion, an initial firing force threshold $FTF_{M3}$ is set, as discussed above. As seen in graph 10150, the initial firing force threshold $FTF_{M3}$ is the same as the initial firing force threshold $FTF_{M2}$ for the state cartridge with the length $d_2$. Initial firing force threshold $FTF_{M3}$ can be greater as the initial firing force threshold $FTF_{M2}$ for the state cartridge with the length $d_2$. As referenced above, the initial firing force threshold $FTF_{M3}$ can be stored in a memory and retrieved by the control system. The initial firing force threshold $FTF_{M3}$ can be set by a user.

The end effector is then utilized to grasp tissue within the jaws of the end effector. In particular, the closure driver is advanced distally to apply a closure force to the second jaw to transition the second jaw toward the closed position. The closure driver can be at a first position intermediate the proximal position and the distal position when the second jaw has reached the closed position. The closure driver can halt advancement toward the distal position once a threshold amount of force has been applied to the tissue by the second jaw, thus preventing the tissue from being damaged. As such, the second jaw is in a position intermediate the open position and the closed position (i.e., a partially closed or partially open position) when the closure driver halts advancement.

Once the closure driver stops advancing, the firing system advances the firing driver through its firing stroke 10106 to deploy staples from the staple cartridge and cut the tissue captured by the end effector. As described above, an amount of time can elapse between the closure driver halting and the firing system initiating to allow for pre-compression of the tissue. As the firing driver is advanced through its firing stroke 10106, the first cam and the second cam of the firing driver apply a closure force to the jaws of the end effector to maintain the end effector in the closed position.

As the firing driver is advanced toward the distal position, the control system monitors an amount of force applied to the end effector by the closure driver (via the first force sensor) and the firing driver (via the second force sensor) and determines an amount of co-operation that exists between the closure system and the firing system to maintain the end effector in the closed position. As shown in graph 10100, the amount of co-operation between the closure system and the firing system is determined by the control system to be at, or substantially at, 100% until the firing driver reaches a length $d_3'$ of the firing stroke 10106. From the initiation of the firing stroke until $d_3'$, with a co-operation of 100%, the firing driver is considered to be in a first firing zone.

At $d_3'$, the amount of closure force applied by the firing driver begins to exceed the amount of closure force applied by the closure driver. Therefore, the control system (via the first and second force sensors) determines the amount of co-operation begins to drop below 100%, and therefore, the firing driver transitions to a second firing zone. As discussed above, the control system adjusts the firing force threshold during the firing stroke based on the amount of co-operation that exists between the closure system and the firing system. Accordingly, in the second firing zone, the control system adjusts 10112 the initial firing force threshold $FTF_{M3}$ to a first adjusted firing force threshold $FTF_{AM3}$ that is less than the initial firing force threshold $FTF_{M3}$. The first adjusted firing force threshold $FTF_{AM3}$ can be stored in a memory and retrieved by the control system. The first adjusted firing force threshold $FTF_{AM3}$ can be user defined. The first adjusted firing force threshold $FTF_{AM3}$ may be the same as the first adjusted firing force threshold $FTF_{AM2}$. The first adjusted firing force threshold $FTF_{AM3}$ may be different than the first adjusted firing force threshold $FTF_{AM2}$. The firing driver can transition to the second firing zone when the amount of co-operation drops below 100% co-operation. The firing driver can transition to the second firing zone when the amount of co-operation drops a threshold amount below 100% co-operation.

As shown in graph 10100, the firing driver continues to advance through its firing stroke 10106 in the second firing zone and the amount of co-operation continues to diminish. At $d_3''$, the amount of co-operation reaches a threshold co-operation percentage X %, and therefore, the firing driver transitions to a third firing zone. The threshold co-operation percentage may be 50% co-operation (a 1-to-2 ratio). The threshold co-operation percentage may be 75% (a 3-to-4 ratio). The threshold co-operation percentage may be 25% (a 1-to-4 ratio). The threshold co-operation percentage can be stored in a memory and retrieved by the control system. The threshold co-operation percentage can be user defined. The threshold co-operation percentage can be set based on the insertion of the staple cartridge into the end effector.

Based on the firing driver transitioning to the third firing zone, the control system adjusts 10114 the first adjusted firing force threshold $FTF_{AM3}$ to a second adjusted firing force threshold $FTF_{SAM3}$ that is less than the first adjusted firing force threshold $FTF_{AM3}$. The second adjusted firing force threshold $FTF_{SAM3}$ can be stored in a memory and retrieved by the control system. The second adjusted firing force threshold $FTF_{SAM3}$ can be defined. After the control system adjusts the first adjusted firing force threshold $FTF_{AM3}$ to the second adjusted firing force threshold $FTF_{SAM3}$, the firing driver continues to advance through the remainder of the firing stroke.

While the above-provided examples illustrate the control system only making, at most, two adjustments to the firing force threshold, the control system can make additional adjustments to the firing force threshold at various other co-operation percentages. The control system can adjust the firing force threshold when the amount of co-operation drops below 100% and reaches a first intermediate threshold percentage above the threshold percentage X %, such as 75% when the threshold percentage is 50%. The control system can adjust the firing force threshold when the amount of co-operation drops below 100% and reaches a first intermediate threshold percentage below the threshold percentage X %, such as 25% when the threshold percentage is 50%.

Figure 7A:
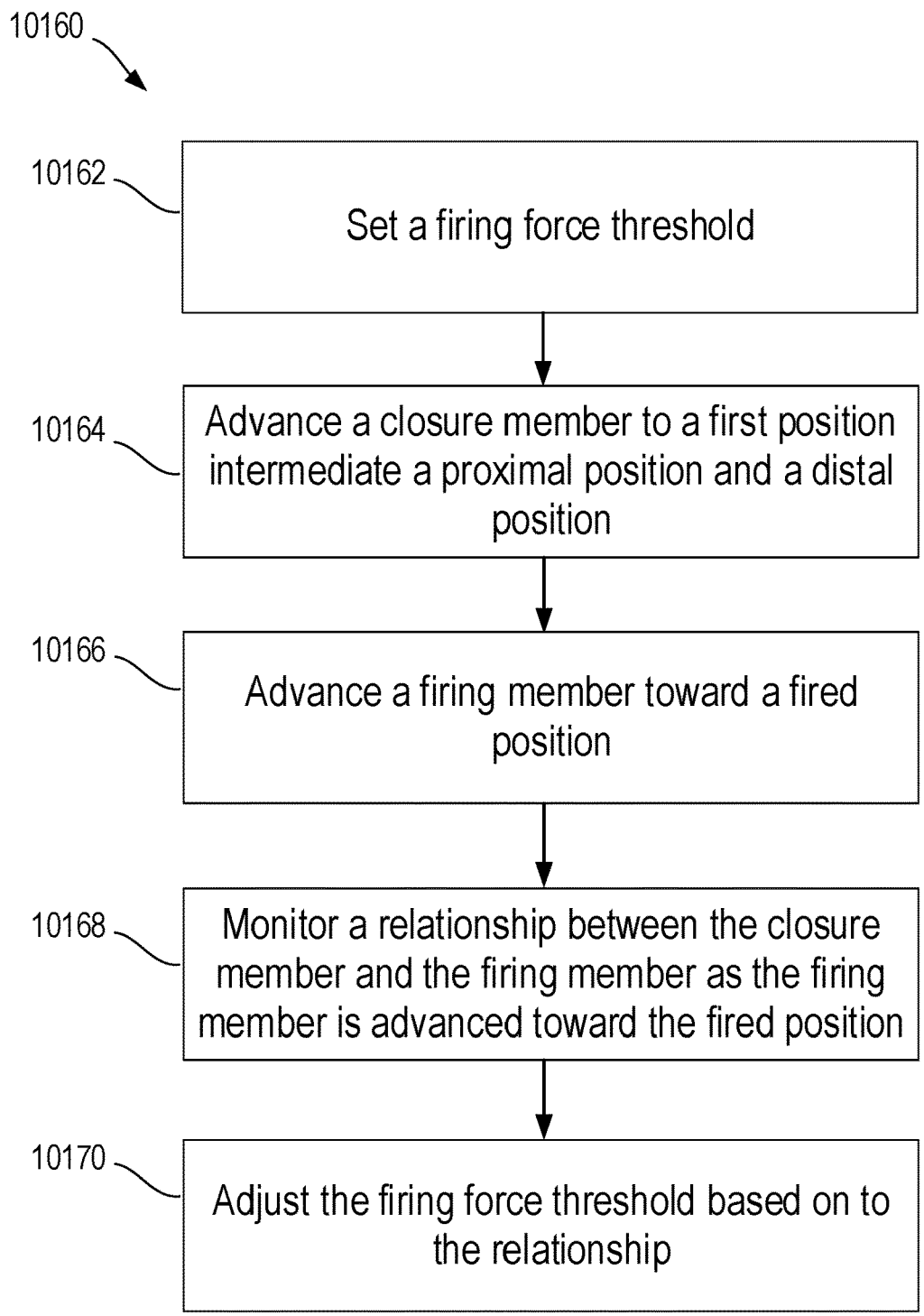
FIG. 7A is a method for controlling a surgical stapling instrument, in accordance with the present disclose.

Referring now to FIG. 7A, a method 10160 for controlling a surgical stapling system is provided, in accordance with the present disclosure. With reference now to FIG. 7A together with FIGS. 3 and 4, in accordance with the method 10160, a control system, such as controller 10033 or controller 10051, can set 10162 a firing force threshold based on a staple cartridge being removably positioned in an end effector of the surgical system, as described elsewhere herein. The firing force threshold can be a threshold that would result in a firing motor, such as firing motor 10056, stalling. The firing force threshold can be a threshold that is less than a maximum firing force threshold that would result in the firing motor stalling.

In accordance with the method 10160, the control system advances 10164 a closure driver to a first position intermediate a proximal position and a distal position. The control system can actuate a closure motor, such as closure motor 10058, to advance a closure driver, such as closure tube 10013, distally.

In accordance with the method 10160, the control system can advance 10166 a firing driver toward a fired position. The control system can actuate a firing motor, such as firing motor 10056, to advance a firing driver, such as firing driver 10024, distally.

In accordance with the method 10160, the control system can monitor 10168 a relationship between the closure driver and the firing driver as the firing driver is advanced toward the fired position. The control system can monitor a relationship between the closure driver and the firing driver by monitoring an amount of co-operation that exists between the closure driver and the firing driver in maintaining an end effector, such as end effector 10002, in a closed position. As described elsewhere herein, the control system can monitor an amount of co-operation that exists by monitoring a ratio of the closure forces that each of the closure driver and the firing driver apply to the end effector.

In accordance with the method 10160, the control system can adjust 10170 the firing force threshold based on to the relationship. The control system can adjust the firing force threshold based on the amount of co-operation that exists between the firing driver and the closure driver to maintain the end effector in the closure position. The control system can adjust the firing force threshold to a first adjusted firing force threshold based on the firing driver applying a greater amount of closure force the closure driver. As described elsewhere herein, the control system can be further configured to determine a zone that the firing driver is located based on the relationship between the closure driver and the firing driver. As such, as described elsewhere herein, the firing driver is determined to be in a first firing zone based on the control system utilizing the initial firing force threshold for comparison to the measured firing force and the firing driver is determined to be in a second firing zone based on the control system utilizing the first adjusted firing force threshold for comparison to the measured firing force.

Figure 8:
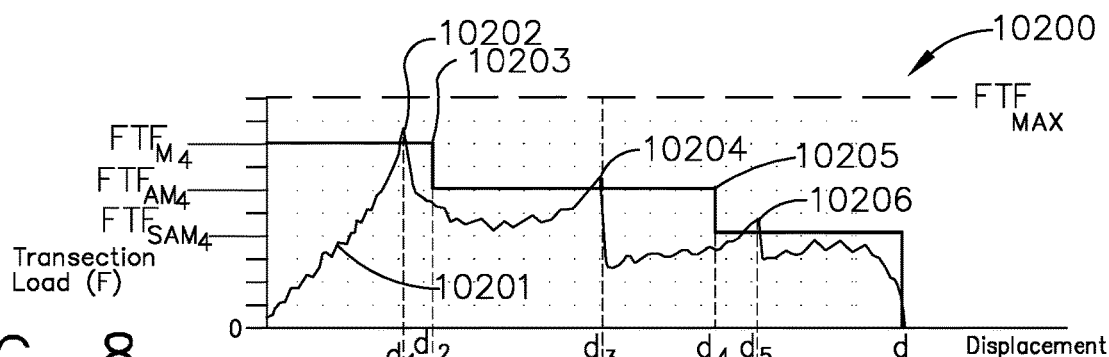
FIG. 8 is a graph that illustrates firing force and firing force thresholds over a firing stroke of a firing driver.
Figure 9:
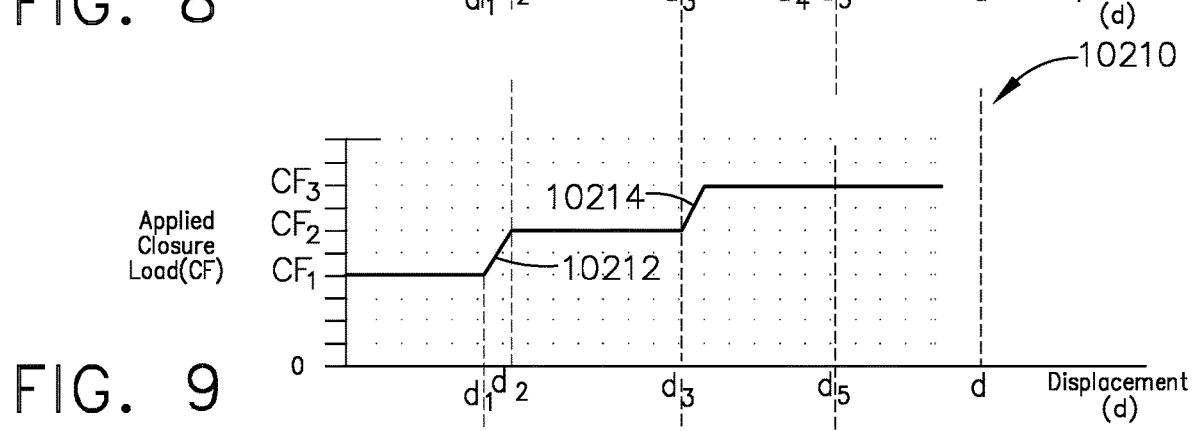
FIG. 9 is a graph that illustrates closure load applied by a closure driver over the firing stroke of the firing driver from FIG. 8.
Figure 10:
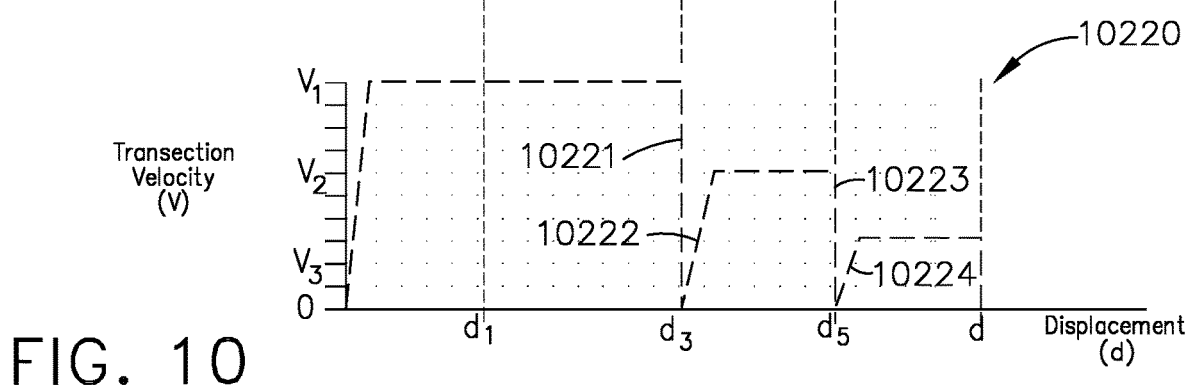
FIG. 10 is a graph that illustrates velocity of the firing driver over the firing stroke of the firing driver from FIG. 8.

As discussed above, based on the amount of co-operation that exists between the closure system and the firing system, the control system also makes adjustments to the closure system and/or the firing system, as well as makes adjustments to the firing force threshold of the firing system. Referring now to FIGS. 8-10, graphs 10200, 10210, 10220 for an exemplary firing stroke of a staple cartridge with a length d are provided. Graph 10200 illustrates the firing force and firing force thresholds over the firing stroke of the firing driver. Graph 10210 illustrates closure load applied by the closure driver over the firing stroke of the firing driver. Graph 10220 illustrates velocity of the firing driver over the firing stroke of the firing driver.

The staple cartridge is inserted into the first jaw of the end effector. Based on the insertion, an initial firing force threshold $FTF_{M4}$ is set, as discussed above. As seen in graph 10200, the initial firing force threshold $FTF_{M4}$ is less than a firing force threshold $FTF_{MAX}$ that would result in the firing motor stalling. The initial firing force threshold $FTF_{M4}$ can be stored in a memory and retrieved by the control system. The initial firing force threshold $FTF_{M4}$ can be set by a user.

The end effector is then utilized to grasp tissue within the jaws of the end effector. In particular, the closure driver is advanced distally to apply a closure force $CF_1$ to the second jaw to transition the second jaw toward the closed position. The closure driver can be at a first position intermediate the proximal position and the distal position when the second jaw applies the closure force $CF_1$ to the second jaw. The closure driver can halt advancement toward the distal position once a threshold amount of force has been applied to the tissue by the second jaw, thus preventing the tissue from being damaged. As such, the second jaw is in a position intermediate the open position and the closed position (i.e., a partially closed or partially open position) when the closure driver halts advancement.

Once the closure driver stops advancing and is applying the closure force $CF_1$, the firing system advances the firing driver through its firing stroke at a velocity $V_1$ (see graph 10220) to deploy staples from the staple cartridge and cut the tissue captured by the end effector. As described above, an amount of time can elapse between the closure driver halting and the firing system initiating to allow for pre-compression of the tissue. As the firing driver is advanced through its firing stroke, the first cam and the second cam of the firing driver apply a closure force to the jaws of the end effector to maintain the end effector in the closed position.

As the firing driver is advanced toward the distal position, the control system monitors an amount of force applied to the end effector by the closure driver (via a first closure force sensor) and the firing driver (via a second closure force sensor) and determines an amount of co-operation that exists between the closure system and the firing system to maintain the second jaw in the closed position. In addition, the control system monitors the force to fire 10201 the firing driver using a firing force sensor. The firing force can be measured using a force sensor on the firing driver. The firing force can be measured using a current sensor that measures current through the firing motor. Various other sensors for measuring the firing force are described elsewhere herein.

As seen in graph 10200, at $d_1$ of the firing stroke, the firing force 10201 exceeds 10202 the firing force threshold. At such time, the amount of co-operation between the firing system and the closure system is still determined to be at 100%, and therefore, the firing driver is determined to be in a first firing zone, as discussed elsewhere herein. Based on the firing driver being in the first firing zone, the control system leverages only the closure system and makes an adjustment to the closure algorithm. Namely, the control system causes the closure driver to advance from the first position to a second position without stopping advancement of the firing driver to increase 10212 the applied closure force from $CF_1$ to $CF_2$. Based on the increased closure force applied by the closure driver, the firing force 10201 drops below the initial firing force threshold $FTF_{M4}$. The second position can be proximal to the distal-most position of the closure driver. The second position can be the distal-most position of the closure driver. The length of the stroke from the first position to the second position can be stored in the memory and retrieved by the control system. The length of the stroke from the first position to the second position can be a length that causes the firing force to drop a predetermined amount.

As the firing driver continues to advance through its firing stroke, the control system continues to monitor the force to fire the firing driver and the amount of co-operation between the closure system and the firing system. At $d_2$, the control system determines that the firing driver begins to apply a greater closure force than the closure driver, and therefore, the co-operation between the closure system and the firing system drops below 100%. Accordingly, the firing driver transitions to a second firing zone. In the second firing zone, the control system adjusts 10203 the initial firing force threshold $FTF_{M4}$ to a first adjusted firing force threshold $FTF_{AM4}$ without pausing advancement of the firing driver.

At $d_3$ of the firing stroke, the firing force 10201 exceeds 10204 the first adjusted firing force threshold $FTF_{AM4}$. At such time, the firing driver is still determined to be in second firing zone. Based on the firing driver being in the second firing zone, the control system leverages both the firing system and the control system and makes an adjustment to the firing algorithm and the closure algorithm. Namely, the control system first pauses 10221 advancement of the firing driver, dropping the velocity of the firing driver from V1 to 0, as shown in graph 10220. In addition, the control system causes the closure driver to advance from the second position to a third position to increase 10214 the applied closure force from $CF_2$ to $CF_3$. Based on the pause of the firing driver and the increased closure force applied by the closure driver, the firing force 10201 drops below the first adjusted firing force threshold $FTF_{AM4}$. The third position can be proximal to the distal-most position of the closure driver. The third position can be the distal-most position of the closure driver. The length of the stroke from the second position to the third position can be stored in the memory and retrieved by the control system. The length of the stroke from the second position to the third position can be a length that causes the firing force to drop a predetermined amount.

The control system can cause the firing driver to resume 10222 advancement after a threshold amount of time of being paused. The threshold amount of time can be stored in a memory. The threshold amount of time can be user defined. The control system can cause the firing driver to resume advancement after the firing force drops a threshold amount below the first adjusted firing force threshold $FTF_{AM4}$. At such time, the control system adjusts the firing algorithm such that the firing driver resumes 10222 advancement at a second speed V2 that is less than the first speed V1. The control system may not adjust the firing speed of the firing driver. The second firing speed can be stored in a memory and retrieved by the control system. The second firing speed can be user defined. The second firing speed can be a function of the displacement of the firing driver within the firing stroke.

As the firing driver continues to advance through its firing stroke, the control system continues to monitor the force to fire on the firing driver and the amount of co-operation between the closure system and the firing system. At $d_4$, the control system determines that the co-operation between the closure system and the firing system reaches a threshold co-operation percentage X %, and therefore, the firing driver transitions to a third firing zone. The threshold co-operation percentage X % may be 50% (a 1-to-2 ratio of closure forces applied by the closure driver and firing driver). The threshold co-operation percentage X % may be 75% (a 3-to-4 ratio of closure forces applied by the closure driver and firing driver). The threshold co-operation percentage X % may be 25% (a 1-to-4 ratio of closure forces applied by the closure driver and firing driver). The threshold co-operation percentage can be stored in a memory and retrieved by the control system. The threshold co-operation percentage can be user defined. The threshold co-operation percentage can be set based on the insertion of the staple cartridge into the end effector. Accordingly, based on the transition to the third firing zone, the control system adjusts 10205 the first adjusted firing force threshold $FTF_{AM4}$ to a second adjusted firing force threshold $FTFS_{AM4}$ without pausing advancement of the firing driver.

At $d_5$ of the firing stroke, the firing force 10201 exceeds 10206 the second adjusted firing force threshold $FTFS_{AM4}$. At such time, the firing driver is determined to be in the third firing zone. Based on the firing driver being in the third firing zone, the control system only leverages the firing system and makes an adjustment to the firing algorithm. Namely, the control system pauses 10223 advancement of the firing driver, dropping the velocity of the firing driver from V2 to 0, as shown in graph 10220. Unlike in the first firing zone and the second firing zone, the control system does not resume advancement of the closure driver in the third firing zone. Based on the pause of the firing driver, the firing force drops below the second adjusted firing force threshold $FTF_{SAM4}$.

The control system can cause the firing driver to resume 10224 advancement after a threshold amount of time of being paused. The threshold amount of time can be stored in a memory. The threshold amount of time can be user defined. The control system can cause the firing driver to resume 10224 advancement after the firing force drops a threshold amount below the second adjusted firing force threshold $FTF_{SAM4}$. At such time, the control system adjusts the firing algorithm such that the firing driver resumes advancement 10224 at a third speed V3 that is less than the second speed V2. The third speed can be a minimum speed. The control system may not adjust the firing speed of the firing driver. The third firing speed can be stored in a memory and retrieved by the control system. The third firing speed can be user defined. The third firing speed can be a function of the displacement of the firing driver within the firing stroke. After resuming advancement 10224 of the firing driver at the third firing speed, the firing driver reaches the end of its firing stroke at d.

Should the firing driver have exceeded the second adjusted firing force threshold $FTF_{SAM4}$ after resuming advancement 10224 of the firing driver at $d_5$ and prior to completion of the firing stroke, the control system would again only leverage the firing system to drop the firing force 10201 below the second adjusted firing force threshold $FTF_{SAM4}$, similar to what was described above.

According, the foregoing provides a control system that leverages the closure system and/or the firing system dependent upon the amount of co-operation that exists between the closure system and the firing system. The amount of leverage that the closure system can provide is greater earlier in the firing stroke of the firing driver than it is later in the firing stroke and, therefore, the closure system is leveraged by the control system exclusively in the first firing zone (when the co-operation is at 100%) and in tandem with the firing system in the second firing zone (when the co-operation is less than 100%, but greater than a threshold percentage X %). After the threshold co-operation percentage has been reached or dropped below, the control system exclusively leverages the firing system for the remainder of the firing stroke. Therefore, the stress on the firing system is diminished as the firing system is exclusively relied upon only in the third zone when the amount of leverage that the closure system can provide is not as great as it is in the first firing zone and the second firing zone.

In addition, the firing zones can be variable in length, rather than predefined. For example, the firing driver transitions from the first firing zone to the second firing zone when the co-operation between the closure system and the firing system drops below 100%. When the co-operation drops below 100% is subject to change from one stroke to the next. For instance, the change in co-operation is based on a variety of factors, such as the thickness, the condition, or the type of tissue positioned in the jaws of the end effector. The co-operation between the closure system and the firing system may drop below 100% faster with thick tissue positioned between the jaws when compared to thin tissue being positioned between the jaws. Accordingly, the firing zones are subject to change from one firing stroke to the next firing stroke as the transition from one zone to the next relies upon the amount of co-operation between the closure and firing system, which can occur at different times during different firing strokes.

Figure 10A:
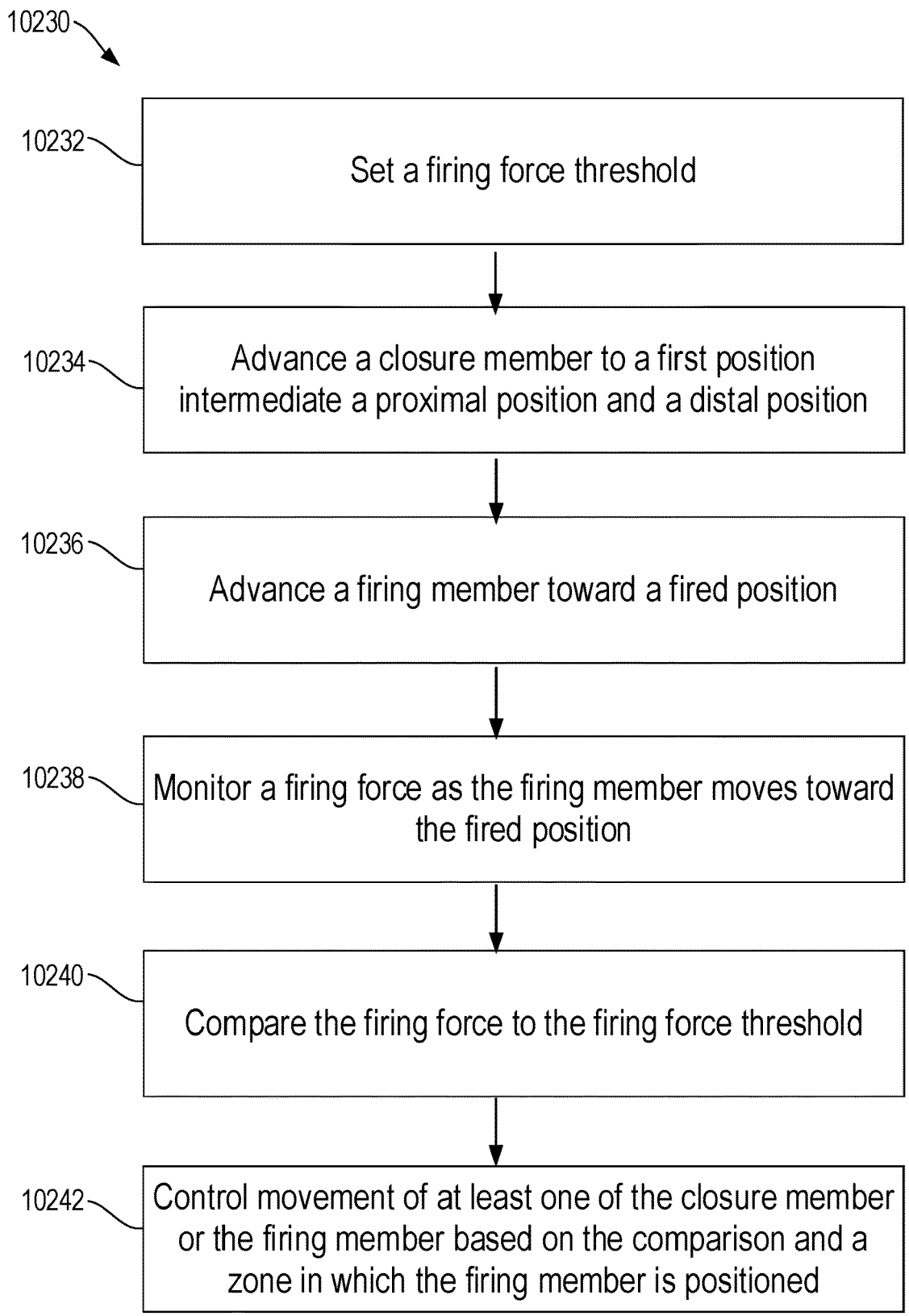
FIG. 10A is a method for controlling a surgical stapling instrument, in accordance with the present disclose.

Referring now to FIG. 10A, a method 10230 for controlling a surgical stapling system is provided, in accordance with the present disclosure. With reference now to FIG. 10A together with FIGS. 3 and 4, in accordance with the method 10230, a control system, such as controller 10033 or controller 10051, sets 10232 a firing force threshold that is a threshold that would result in a firing motor, such as firing motor 10056, stalling. The control system can set a firing force threshold that is less than a maximum firing force threshold that would result in the firing motor stalling. How the control system sets a firing force threshold in accordance with the present disclosure are described elsewhere herein.

In accordance with the method 10230, the control system advances 10234 a closure driver to a first position intermediate a proximal position and a distal position. The control system can actuate a closure motor, such as closure motor 10058, to advance a closure driver, such as closure tube 10013, distally.

In accordance with the method 10230, the control system advances 10234 a firing driver toward a fired position. The control system can actuate a firing motor, such as firing motor 10056, which applies a firing force to a firing driver, such as firing driver 10024, to advance the firing driver distally.

In accordance with the method 10230, the control system monitors 10238 the firing force as the firing driver moves toward the fired position. The surgical stapling system can include a force sensor, such sensor 10039 or sensor 10054, that senses the firing force that the firing motor applies to the firing driver.

In accordance with the method 10230, the control system compares 10240 the firing force to the firing force threshold. The control system can be in operation communication with the force sensor and receives the monitored firing force from the force sensor. The control system compares the firing force to the firing force threshold to determine if the firing force is below the firing force threshold or if the firing force has reached or exceeded the firing force threshold.

In accordance with the method 10230, the control system controls 10242 movement of at least one of the closure driver or the firing driver based on the comparison and a zone in which the firing driver is positioned. Based on the control system determining that the firing force has reached or exceeded the firing force threshold, the control system can determine which zone that the firing driver is positioned in order to determine which of the closure driver and/or the firing driver should be adjusted, as described elsewhere herein.

The method 10230 can optionally include monitoring a relationship between the closure driver and the firing driver as the firing driver is advanced toward the fired position. As described elsewhere herein, the control system can monitor the relationship between the closure driver and the firing driver by monitoring an amount of co-operation that exists between the closure driver and the firing driver in maintaining the end effector in its closed state. The control system can monitor an amount of co-operation that exists between the closure driver and the firing driver by monitoring a ratio between closure forces that each of the closure driver and the firing driver apply to the end effector to maintain the end effector in the closed state.

Setting 10232 can optionally include setting an initial firing force threshold, adjusting the initial firing force threshold to a first adjusted firing force threshold based on the monitored relationship between the closure driver and the firing driver, and adjusting the adjusting the first adjusted firing force threshold to a second adjusted firing force threshold based on the monitored relationship between the closure driver and the firing driver. How the control system sets an initial firing force threshold in accordance with the present disclosure are described elsewhere herein.

The method 10230 can optionally include determine a zone from a plurality of zones that the firing driver is located. As described elsewhere herein, the control system can determine a zone that the firing driver is located according to the amount of co-operation that exists between the closure driver and the firing driver. With a determined co-operation of 100%, the firing driver can be considered to be in a first firing zone. With the firing driver being determined to be in a first firing zone, the method 10230 can optionally include controlling movement of the closure driver and not controlling movement of the firing driver based on the monitored firing force reaching the initial firing force threshold and the firing driver being positioned in the first firing zone.

With a determined co-operation below 100%, the firing driver can be considered to be in a second firing zone. The control system can adjust the initial firing force threshold to the first adjusted firing force threshold, based on the second closure force being greater than the first closure force, which would result in a co-operation below 100%. With the firing driver being determined to be in the second firing zone, the method 10230 can optionally include controlling movement of the closure driver and the firing driver based on the monitored firing force reaching the first adjusted firing force threshold and the firing driver being positioned in the second firing zone.

The method 10230 can optionally include set a threshold co-operation percentage. How the control system sets the threshold co-operation percentage in accordance with the present disclosure are described elsewhere herein. With a determined co-operation below the threshold co-operation percentage, the firing driver can be considered to be in a third firing zone. The control system can adjust the first adjusted firing force threshold to the second adjusted firing force threshold, based on the second closure force being greater than the first closure force that would result in a co-operation percentage below the threshold co-operation percentage. With the firing driver being determined to be in the third firing zone, the method 10230 can optionally include controlling movement of the firing driver and not controlling movement of the closure driver based on the firing force reaching the second adjusted firing force threshold and the firing driver being positioned in the third firing zone.

As discussed above, it is desirable to maximize the amount of impact that the closure system provides in order to reduce the force to fire the firing driver, and thus, reduce the strain on the firing system. The control system can receive inputs from multiple sensors to provide this outcome. The control system can receive tissue response data and device data from the sensors so as to set appropriate parameters for both the closure system and the firing system so as to increase the amount of impact that the closure system provides and reduce the strain on the firing system, while still maintaining a reasonable firing stroke time.

The tissue response data can comprise the thickness of tissue captured by the end effector, the stiffness of tissue captured by the end effector, the condition of the tissue captured by the end effector (heathy, diseased, etc.), the type of tissue captured by the end effector, or any other type of tissue response data described elsewhere herein. The device data can comprise an articulation angle between the end effector and the shaft, the number of uses of the surgical system, the type of staple cartridge positioned in the end effector, or any other type of device data described elsewhere herein. These pieces of data can be used alone, or in combination with each other, by the control system to make any suitable adjustment to the closure system so as to reduce the load on the firing system during the firing stroke.

A staple cartridge can be inserted into the first jaw of the end effector. As described elsewhere herein, the control system interrogates the staple cartridge to determine a type of staple cartridge that is positioned in the end effector. The end effector is then utilized to grasp tissue within the jaws thereof. In particular, the closure driver is advanced from a proximal position toward a distal position to transition the second jaw toward the closed position and apply an initial closure force to the second jaw. The closure driver can be at a position intermediate the proximal position and the distal position when the second jaw applies the closure force to the second jaw. The closure driver can halt advancement toward the distal position once a threshold amount of force has been applied to the tissue by the second jaw, thus preventing the tissue from being damaged. As such, the second jaw is in a position intermediate the open position and the closed position (i.e., a partially closed or partially open position) when the closure driver halts advancement.

With the tissue grasped, the control system receives data from any number of sensors within the surgical system to determine tissue response data, as described above or elsewhere herein. In addition, the control system receives data from any number of sensors within the surgical system to determine device data, such as the articulation angle of the end effector, the number of uses of the end effector, or any other type of device data described above or elsewhere herein. Based on the tissue response data and the device data, the control system adjusts the closure algorithm such that the closure driver is moved to apply an adjusted closure force to the second jaw. In addition, once the closure tube has stopped moving, the control system provides a message to a user via a display, such as display 10068, indicating that an amount of time should be allowed to elapse prior to firing. This amount of time allows the tissue to relax and stabilize, and thus, will further reduce the firing load on the firing driver. After the amount of time has elapsed, the control system provides a message on the display to the user, indicating to the user that the firing system can be actuated to advance the firing driver through the firing stroke.

As firing system advances the firing driver through its firing stroke to deploy staples from the staple cartridge and cut the tissue captured by the end effector, the control system monitors the firing load on the firing system. The firing load can be measured using a force sensor on the firing driver. The firing load can be measured using a current sensor that measures current through the firing motor. Various other sensors for measuring the firing load on the firing driver and firing system are described elsewhere herein.

The firing load on the firing driver can remain below a threshold firing load during the entire firing stroke, and therefore, no adjustments are made to the firing system or the closure system. The threshold firing load can be stored in a memory and retrievable by the control system. The threshold firing load can be user defined.

The control system can determine that the firing load reaches or exceeds the threshold firing load. Based on the threshold firing load being reached or exceeded, the control system adjusts the closure algorithm to cause the closure driver to advance distally toward its distal position. By first making adjustments only to the closure system, the control system attempts to reduce firing loads on the firing driver without interrupting the firing stroke of the firing driver, and thus, potentially keeps the firing force below the firing threshold without impacting transection times.

If advancing the closure driver toward the distal position drops the firing load below the threshold firing load, the control system can continue to advance the firing driver through its firing stroke without any adjustments to the firing algorithm. If advancing the closure driver toward the distal position does not drop the firing load below the threshold firing load, the control system can continue to advance the closure driver until the firing load drops below the firing threshold. The control system continues to advance the closure driver so long as the firing load is above the firing threshold and the closure driver is not at its distal position. Should the closure driver reach its distal position without the firing load dropping below the threshold firing load, the control system then makes adjustments to the firing algorithm to reduce the firing force on the firing system. Adjustments to the firing algorithm can comprise pausing advancement of the firing driver. Adjustments to the firing algorithm can comprise reducing the speed of the firing driver. Adjustments to the firing algorithm can comprise pausing advancement of the firing driver and resuming advancement of the firing driver at a slower speed. Other adjustments to the firing algorithm for reducing firing force are described elsewhere herein.

Accordingly, the control system makes adjustments exclusively to the closure system during the firing stroke of the firing driver until the closure system reaches its maximum limits, such as its distal-most position. This provides the benefit of managing the firing load without impacting the transection time of the firing driver. Once the closure system reaches its maximum limits, the control system switches to making adjustments to the firing system to control the firing loads.

The firing stroke of the firing driver can include predefined zones and the control system can make adjustments to the closure system and/or firing system based upon which zone the firing driver is within during the firing stroke. The predefined zones can include a pre-firing zone, a closure firing zone, a middle firing zone, and an end firing zone. The pre-firing zone can comprise a zone when the firing driver is in its proximal position. As described elsewhere herein, the stapling firing system may not include a closure driver, and instead, the closing of the second jaw can be done by the firing driver moving from a proximal position to an intermediate position. As the firing driver moves toward the intermediate position, the cams on the firing driver engage a ramp on the second jaw to cam the second jaw from the open position toward the closed position. As sicj, the closure firing zone is defined between the proximal position of the firing driver and the intermediate position of the firing driver. The middle firing zone can comprise a first portion of the firing stroke, such as the first half of the firing stroke, in which the firing driver deploys staples from the staple cartridge. The end firing zone can comprise a second portion of the firing stroke, such as the remaining half of the firing stroke, in which the firing driver deploys staples from the staple cartridge.

The zones described elsewhere herein can be defined, or adjusted, based on inputs from sensors within the surgical system to the control system. The inputs can comprise a device type, a tissue type, a tissue location within the end effector, an amount of pressure applied to the tissue, an amount of time that the end effector has clamped the tissue prior to firing, the clamping speed of the second jaw, the force to close (FTC) the second jaw, the voltage applied to the closure motor, the current applied to the closure motor, the length of the staple cartridge positioned in the end effector, the type of cartridge positioned in the end effector, a type of buttress positioned on the deck of the staple cartridge, or the articulation angle of the end effector relative to the shaft, or any combination thereof. The length of the staple cartridge positioned in the end effector and the type of cartridge positioned in the end effector can be used by the control system to set initial firing parameters of the firing system, such as firing speed, firing force, or any other suitable firing parameter described elsewhere herein.

The surgical stapling system can comprise a modular surgical stapling system where the end-effector can be interchanged, examples of which are described in U.S. Patent Application Publication No. 2019/0209249. The surgical stapling system can include an end effector with a first stapling length and replaced with an end effector with a second stapling length that is different than from the first stapling length. Based on the adjustment, the control system adapts the motor control algorithms for the closure motor and/or firing motor for the specific end effector properties, and then also with the individual calibration properties of the specific device, as discussed above.

As discussed elsewhere herein, a control system can utilize the closure system alone, or in combination with the firing system, during a first portion of the firing stroke when the amount of leverage that the closure system can provide is high. Once the firing driver has transitioned to a second, later portion in the firing stroke, adjustments are only made to the firing algorithm as adjustments to the closure algorithm provide less of an effect than earlier on in the firing stroke.

For instance, as discussed elsewhere herein, the control system determines an amount of co-operation that exists between the closure system and the firing system to define variable zones such that the control system knows whether to adjust the closure algorithm, the firing algorithm, or a combination thereof. The co-operative zones can be pre-defined, stored in a memory, such as memory 10035 or memory 10053, and can be retrieved by the control system. The predefined co-operative zones can be a function of the length of the staple cartridge. The predefined co-operative zones can be the same regardless of the staple cartridge length. The control system can define a high co-operative zone over a first portion of the staple cartridge length and a low co-operative zone over a second portion of the staple cartridge length. The first portion can comprise the first half of the cartridge length and the second portion can comprise the second half of the cartridge length. The first portion can comprise the first third of the cartridge length and the second portion can comprise the remaining two-thirds of the cartridge length. The first portion can comprise the first two-thirds of the cartridge length and the second portion can comprise the remaining third of the cartridge length.

Figure 11:
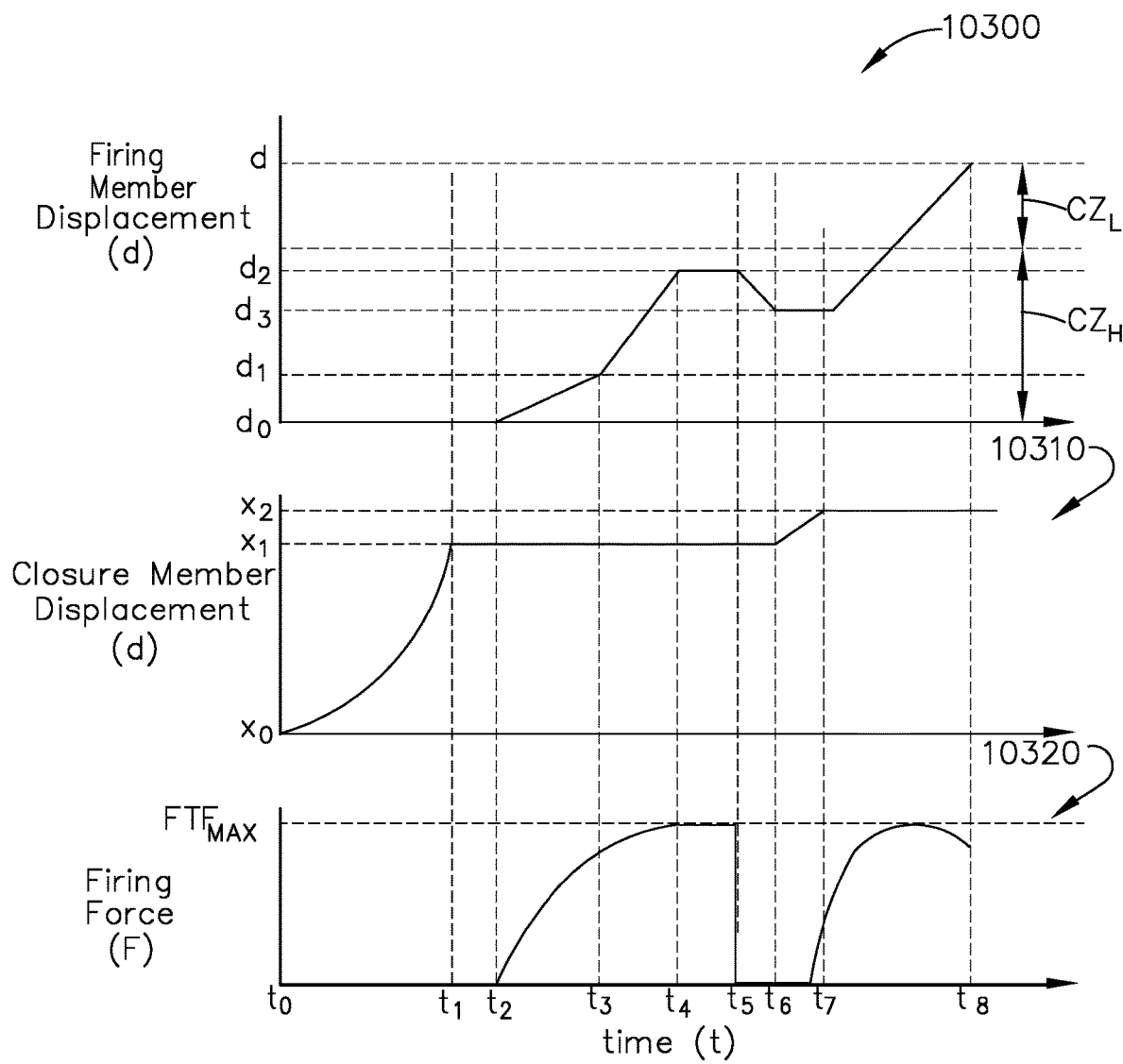
FIG. 11 is graphs for an exemplary firing stroke of a firing driver though a staple cartridge.

Referring now to FIG. 11, graphs 10300, 10310, 10320 for an exemplary firing stroke of a firing driver though a staple cartridge with a length d are provided. Graph 10300 illustrates the displacement of a firing driver, such as firing driver 10024, over time. Graph 10310 illustrates the displacement of a closure driver, such as closure tube 10013, over time. Graph 10320 illustrates the firing force on the firing driver over time.

The staple cartridge is inserted into the first jaw of the end effector. Based on the insertion, a firing force threshold $FTF_{MAX}$ is set, as shown in graph 10320. The firing force threshold $FTF_{MAX}$ can be defined as the threshold that would result in a firing motor that drives the firing driver, such as firing motor 10056, stalling. The firing force threshold $FTF_{MAX}$ can be stored in a memory and retrievable by the control system. The staple cartridge can include an RFID tag positioned thereon and the control system includes an RFID scanner that scans that RFID tag to determine a type of staple cartridge that has been inserted into the end effector. Based on the determination, the control system retrieves the firing force threshold $FTF_{MAX}$ stored in a memory. The firing force threshold $FTF_{MAX}$ can be set by a user.

In addition, based on the insertion of the staple cartridge, the control system defines a high co-operative zone $CZ_H$ and a low co-operative zone $CZ_L$ for the firing stroke of the firing driver. The high co-operative zone $CZ_H$ and the low co-operative zone $CZ_L$ can be predefined zones stored in the memory and retrieved by the control system. The high co-operative zone $CZ_H$ and the low co-operative zone $CZ_L$ can be a function of the staple cartridge length. The high co-operative zone $CZ_H$ and the low co-operative zone $CZ_L$ can be user defined. The high co-operative zone $CZ_H$ can comprise a first portion of the cartridge length and the low co-operative zone $CZ_L$ can comprise a second portion of the cartridge length. The high co-operative zone $CZ_H$ can comprise the first half of the cartridge length and the low co-operative zone $CZ_L$ can comprise the second half of the cartridge length. The high co-operative zone $CZ_H$ can comprise the first third of the cartridge length and the low co-operative zone $CZ_L$ can comprise the remaining two-thirds of the cartridge length. The high co-operative zone $CZ_H$ can comprise the first two-thirds of the cartridge length and the low co-operative zone $CZ_L$ can comprise the remaining third of the cartridge length.

The end effector is then utilized to grasp tissue within the jaws of the end effector. In particular, referring to graph 10310, from $t_0$ to $t_1$, the closure driver is advanced distally from a proximal position $x_0$ to a first intermediate position $x_1$ by a closure motor, such as closure motor 10058, to apply a closure force to a second jaw, such as second jaw 10006, to transition the second jaw toward the closed position. The first intermediate position $x_1$ can be a position intermediate the proximal position $x_0$ and the distal position of the closure driver when the second jaw has reached the closed position. The closure driver can halt advancement toward the distal position once a threshold amount of force has been applied to the tissue by the second jaw, thus preventing the tissue from being damaged. As such, the second jaw may be in a position intermediate the open position and the closed position (i.e., a partially closed or partially open position) when the closure driver halts advancement at the first intermediate position $x_1$.

Once the closure driver stops advancing at $t_1$, an amount of time is allowed to elapse ($t_1$ to $t_2$) before the firing system is initiated. The amount of time can be a predefined amount of time stored in the memory and retrievable by the control system. The amount of time can be variable and a function of the length of the staple cartridge. The amount of time can be a function of the closure force applied to the tissue by the second jaw. For instance, the amount of time can correspond to the amount of time take for the closure force applied by the second jaw to drop a predefined amount, indicative of tissue thinning. The amount of time can be a function of how long it took the closure driver to reach the first intermediate position $x_1$. Other amounts of precompression time are described in more detail in U.S. patent application Ser. No. 17/957,946, which is hereby incorporated by reference in its entirety herein.

At $t_2$, referring to graph 10300 the firing system is actuated to advance the firing driver toward its distal position. In particular, the firing driver is advanced from its proximal positon $d_0$ through the high co-operative zone $CZ_H$. The control system can comprise a positon sensor that senses a position of the firing driver to determine if the firing driver is within the high co-operative zone $CZ_H$ or the low co-operative zone $CZ_L$. From $t_2$ to $t_3$, the firing driver is advanced at a first speed from its proximal position $d_0$ to a lockout position $d_1$, which causes the firing force to rise (see graph 10320). The control system can include a force sensor that measures the firing force on the firing driver. The control system can include a current sensor that senses a current through the firing motor to determine the firing force. Various other force sensors are described elsewhere herein. At the lockout position, a lockout can be situated in the end effector that prevents advancement of the firing driver if a staple cartridge is not positioned therein. An exemplary lockout is provided in U.S. Patent Application Publication No. 2019/0298350, which is hereby incorporated by reference in its entirety herein. From the lockout position $d_1$, the firing driver is then advanced at a second speed greater than the first speed toward the distal position. In accordance with the present disclosure, the firing driver can be advanced at a unitary speed.

At $t_4$, referring to graph 10320, the control system detects that the firing force has reached the firing force threshold $FTF_{MAX}$ at point $d_2$ of the firing stroke. Accordingly, the control system pauses advancement of the firing driver for an amount of time ($t_4$ to $t_5$). The amount of time can be predefined and stored in the memory. The amount of time can be a function of the rate at which the firing force approached the firing force threshold $FTF_{MAX}$. The amount of time can be a function of the number of pauses that have occurred in the firing stroke up to the pause. The length of the pause can be user defined.

As shown in graph 10320, despite the pause in the firing stroke, the firing force does not drop below the firing force threshold $FTF_{MAX}$, and therefore, the firing driver cannot continue to advance through the firing stroke. However, seen in graph 10300, the control system determines that the firing driver is still within the high co-operative zone $CZ_H$, and therefore, the control system leverages the closure system to reduce the firing force.

As seen in graph 10300, at $t_5$, the firing driver is retracted proximally by the firing motor from $d_2$ to $d_3$, causing the firing force to drop to 0, as seen in graph 10320. The length of the retraction stroke from $d_2$ to $d_3$ can be predefined. The length of the retraction stroke can be defined as the displacement of the firing driver required to drop the firing force to 0. At $t_6$, prior to re-advancing the firing driver, the closure driver is advanced distally from the first intermediate position $x_1$ to a second intermediate position $x_2$ to apply additional closure force to the tissue via the second jaw. The second intermediate position $x_2$ can be proximal to the distal-most position of the closure driver. The second intermediate position $x_2$ can be the distal-most position of the closure driver. The length of the stroke from $x_1$ to $x_2$ can be stored in the memory and retrieved by the control system. The length of the stroke from $x_1$ to $x_2$ can be user defined.

At $t_7$, the control system actuates the firing motor to resume advancement of the firing driver toward its distal position d. As the firing driver advances toward the distal position, the firing force does not exceed the firing force threshold $FTF_{MAX}$, so the control system takes no additional actions.

Figure 12:
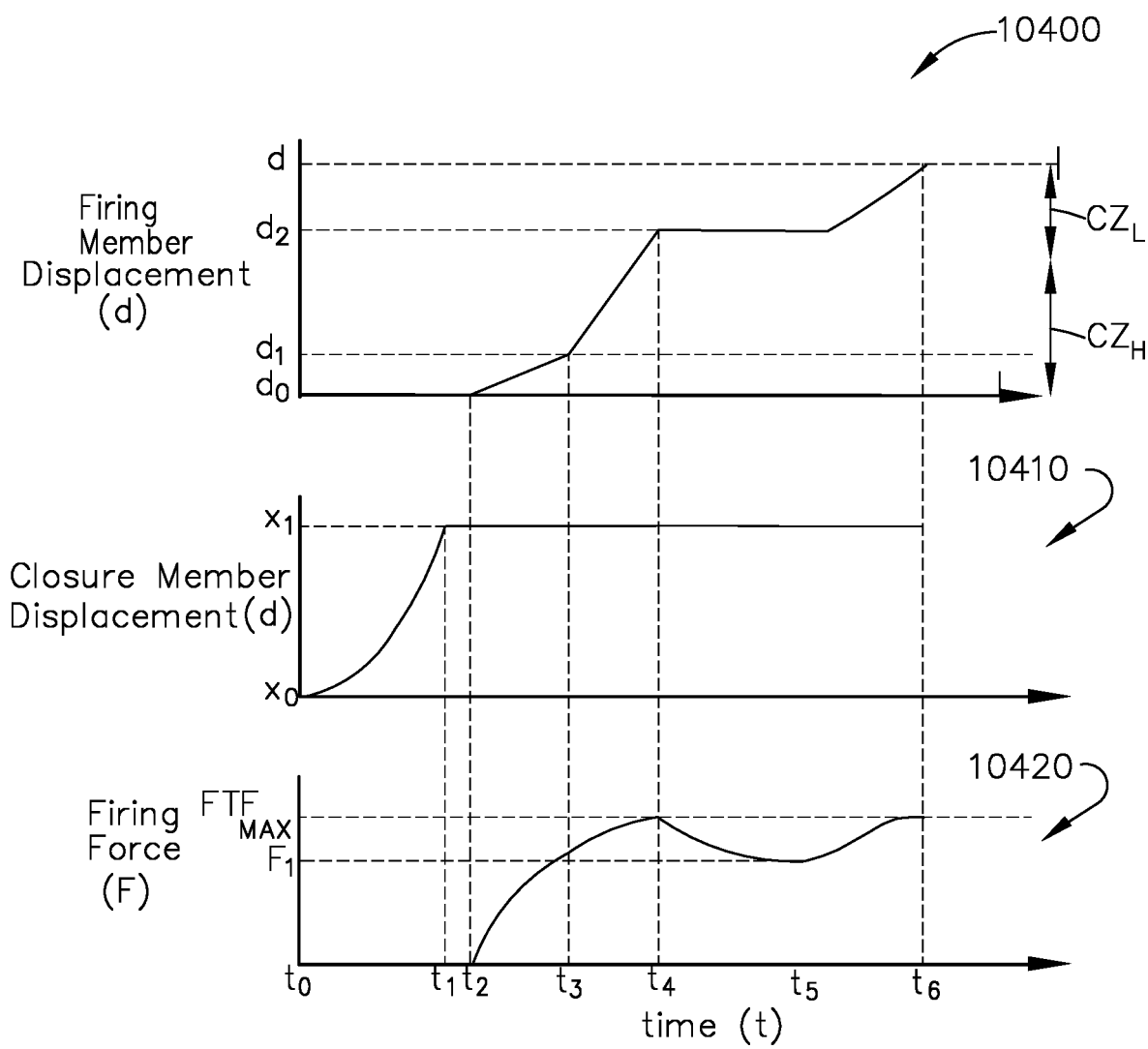
FIG. 12 is graphs for another exemplary firing stroke of a firing driver though a staple cartridge.

Referring now to FIG. 12, graphs 10400, 10410, 10420 for another exemplary firing stroke of a firing driver though a staple cartridge with a length d are provided. Graph 10400 illustrates the displacement of a firing driver, such as firing driver 10024, over time. Graph 10410 illustrates the displacement of a closure driver, such as closure tube 10013 (e.g., closure driver), over time. Graph 10420 illustrates the firing force on the firing driver over time.

The staple cartridge is inserted into the first jaw of the end effector. Based on the insertion, a firing force threshold $FTF_{MAX}$ is set, as shown in graph 10420. The firing force threshold $FTF_{MAX}$ can be defined as the threshold that would result in a firing motor that drives the firing driver, such as firing motor 10056, stalling. The firing force threshold $FTF_{MAX}$ can be stored in a memory, such as memory 10035 or memory 10053, and retrievable by the control system. The staple cartridge can include an RFID tag positioned thereon and the control system includes an RFID scanner that scans that RFID tag to determine a type of staple cartridge that has been inserted into the end effector. Based on the determination, the control system retrieves the firing force threshold $FTF_{MAX}$ stored in the memory. The firing force threshold $FTF_{MAX}$ can be set by a user.

In addition, based on the insertion of the staple cartridge, the control system defines a high co-operative zone $CZ_H$ and a low co-operative zone $CZ_L$ for the firing stroke of the firing driver. The high co-operative zone $CZ_H$ and the low co-operative zone $CZ_L$ can be predefined zones stored in the memory and retrieved by the control system. The high co-operative zone $CZ_H$ and the low co-operative zone $CZ_L$ can be a function of the staple cartridge length. The high co-operative zone $CZ_H$ and the low co-operative zone $CZ_L$ can be user defined. The high co-operative zone $CZ_H$ can comprise a first portion of the cartridge length and the low co-operative zone $CZ_L$ can comprise a second portion of the cartridge length. The high co-operative zone $CZ_H$ can comprise the first half of the cartridge length and the low co-operative zone $CZ_L$ can comprise the second half of the cartridge length. The high co-operative zone $CZ_H$ can comprise the first third of the cartridge length and the low co-operative zone $CZ_L$ can comprise the remaining two-thirds of the cartridge length. The high co-operative zone $CZ_H$ can comprise the first two-thirds of the cartridge length and the low co-operative zone $CZ_L$ can comprise the remaining third of the cartridge length.

The end effector is then utilized to grasp tissue within the jaws of the end effector. In particular, referring to graph 10410, from $t_0$ to $t_1$, the closure driver is advanced distally from a proximal position $x_0$ to a first intermediate position $x_1$ by a closure motor, such as closure motor 10058, to apply a closure force to a second jaw, such as second jaw 10006, to transition the second jaw toward the closed position. The first intermediate position $x_1$ can be a position intermediate the proximal position $x_0$ and the distal position of the closure driver when the second jaw has reached the closed position. The closure driver can halt advancement toward the distal position once a threshold amount of force has been applied to the tissue by the second jaw, thus preventing the tissue from being damaged. As such, the second jaw may be in a position intermediate the open position and the closed position (i.e., a partially closed or partially open position) when the closure driver halts advancement at the first intermediate position $x_1$.

Once the closure driver stops advancing at $t_1$, an amount of time is allowed to elapse (from $t_1$ to $t_2$) before the firing system is initiated. The amount of time can be a predefined amount of time stored in the memory and retrievable by the control system. The amount of time can be variable and a function of the length of the staple cartridge. The amount of time can be a function of the closure force applied to the tissue by the second jaw. For instance, the amount of time can correspond to the amount of time take for the closure force applied by the second jaw to drop a predefined amount, indicative of tissue thinning. The amount of time can be a function of how long it took the closure driver to reach the first intermediate position $x_1$. Other amounts of precompression time are described in more detail in U.S. patent application Ser. No. 17/957,946, which is hereby incorporated by reference in its entirety herein.

At $t_2$, referring to graph 10400, the firing system is actuated to advance the firing driver toward its distal position. In particular, the firing driver is advanced from its proximal positon do through the high co-operative zone $CZ_H$. The control system can comprise a positon sensor that senses a position of the firing driver to determine if the firing driver is within the high co-operative zone $CZ_H$ or the low co-operative zone $CZ_L$. From $t_2$ to $t_3$, the firing driver is advanced at a first speed from its proximal position $d_0$ to a lockout position $d_1$, which causes the firing force to rise (see graph 10420). The control system can include a force sensor that measures the firing force on the firing driver. The control system can include a current sensor that senses a current through the firing motor to determine the firing force. At the lockout position $d_1$, a lockout can be situated in the end effector that prevents advancement of the firing driver if a staple cartridge is not positioned therein, as discussed herein above. From the lockout position $d_1$, the firing driver is then advanced at a second speed greater than the first speed toward the distal position. In accordance with the present disclosure, the firing driver can be advanced at a unitary speed.

At $t_4$, referring to graph 10420, the control system detects that the firing force has reached the firing force threshold $FTF_{MAX}$ at point $d_2$ of the firing stroke. Accordingly, the control system pauses advancement of the firing driver, which causes the firing force to drop below the firing force threshold $FTF_{MAX}$.

As shown in graph 10400, unlike the example shown in graph 10300, the control system determines that the firing driver is no longer within the high co-operative zone $CZ_H$, but rather, has moved into the low co-operative zone $CZ_L$. Therefore, the control system does not leverage the closure system to reduce the firing force. Rather, in the low co-operative zone $CZ_L$, the control system controls the firing load on the firing driver by making adjustments to the firing algorithm. The control system can adjust the firing algorithm to pause advancement of the firing driver for an amount of time. The amount of time can be predefined, stored in the memory, and retrieved by the control system. The amount of time can be a function of the rate at which the firing force approached the firing force threshold $FTF_{MAX}$. The amount of time can be a function of the number of pauses that have occurred in the firing stroke. The length of the pause can be user defined. The amount of time can be an amount of time taken for the firing force to drop a threshold amount below the firing force threshold $FTF_{MAX}$. The control system can adjust the firing algorithm by reducing the speed of the firing driver. The control system can adjust the firing algorithm by reducing the speed of the firing driver after pausing the firing driver. The control system can adjust the firing algorithm by reducing the speed of the firing driver to a minimum speed. The control system can adjust the firing algorithm by reducing the speed of the firing driver to a speed intermediate a current speed and the minimum speed.

As seen in graphs 10400 and 10420, at to, the firing driver resumes advancement toward the distal position after the firing force drops to a force $F_1$. As the firing driver advances toward the distal position, the firing force does not exceed the firing force threshold $FTF_{MAX}$, so the control system takes no additional actions. However, as discussed above, had the firing force threshold reached or exceeded the firing force threshold $FTF_{MAX}$, the control system would only make adjustments to the firing algorithm.

Accordingly, the foregoing provides predefined zones that signal to the control system which system (the closure system or the firing system) the control system should leverage should the firing force reach or exceed the firing force threshold. When the firing driver is in the high co-operative zone $CZ_H$, the control system can exclusively leverage the closure system. When the firing driver is in the low co-operative zone $CZ_L$, the control system can exclusively leverags the firing system. When the firing driver is in the high co-operative zone $CZ_H$, the control system can leverage a combination of the firing system and the closure system, as described elsewhere herein. A middle co-operative zone can be defined intermediate the high co-operative zone $CZ_H$ and the low co-operative zone $CZ_L$. As such, the control system leverages the closure system in the high co-operative zone $CZ_H$, the firing system in the low co-operative zone $CZ_L$, and a combination of both the closure system and the firing system in the middle co-operative zone.

Figure 12A:
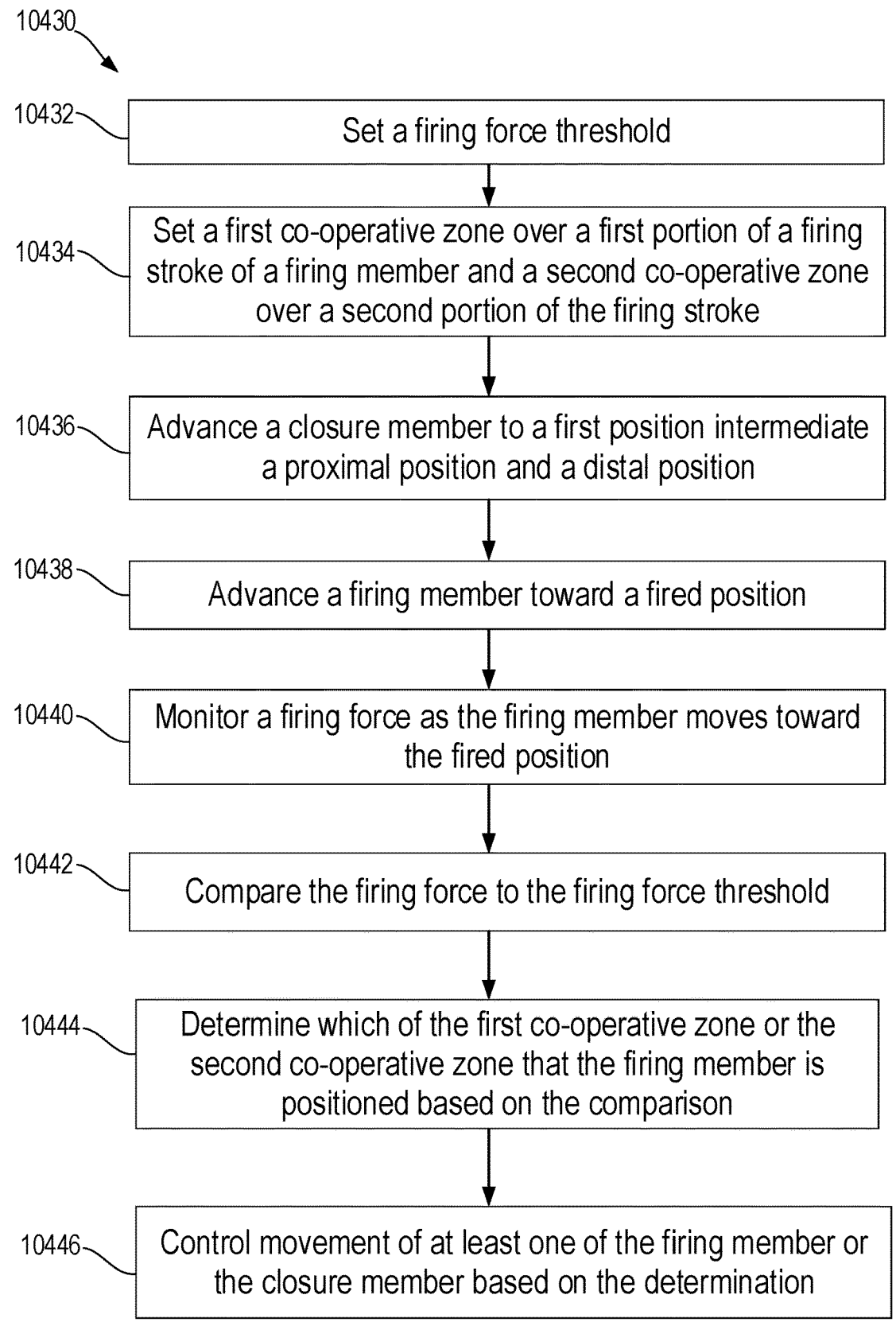
FIG. 12A is a method for controlling a surgical stapling instrument, in accordance with the present disclose.

Referring now to FIG. 12A, a method 10430 for controlling a surgical stapling system is provided, in accordance with the present disclosure. The method 10430 comprises setting 10432 a firing force threshold. A control system, such as controller 10033 or controller 10051, can set a firing force threshold that is a threshold that would result in a firing motor, such as firing motor 10056, stalling. The control system can set a firing force threshold that is less than a maximum firing force threshold that would result in the firing motor stalling. How the control system sets a firing force threshold in accordance with the present disclosure are described elsewhere herein.

The method 10430 further comprises setting 10434 a first co-operative zone over a first portion of a firing stroke of a firing driver and a second co-operative zone over a second portion of the firing stroke. The first co-operative zone can comprise a high co-operative zone $CZ_H$ and the second co-operative zone can comprise a low co-operative zone $CZ_L$. How the control system sets the co-operative zones and the length of the firing zones in accordance with the present disclosure are described elsewhere herein.

The method 10430 further comprises advancing 10436 a closure driver to a first position intermediate a proximal position and a distal position. The control system can actuate a closure motor, such as closure motor 10058, to advance a closure driver, such as closure tube 10013, distally.

The method 10430 further comprises advancing 10438 a firing driver toward a fired position. The control system can actuate a firing motor, such as firing motor 10056, which applies a firing force to a firing driver, such as firing driver 10024, to advance the firing driver distally.

The method 10430 further comprises monitoring 10440 the firing force as the firing driver moves toward the fired position. The surgical stapling system can include a force sensor, such sensor 10039 or sensor 10054, that senses the firing force that the firing motor applies to the firing driver.

The method 10430 further comprises comparing 10442 the firing force to the firing force threshold. The control system can be in operation communication with the force sensor and receives the monitored firing force from the force sensor. The control system compares the firing force to the firing force threshold to determine if the firing force is below the firing force threshold or if the firing force has reached or exceeded the firing force threshold.

The method 10430 further comprises determining 10444 which of the first co-operative zone or the second co-operative zone that the firing driver is positioned based on the comparison. The surgical stapling system can include a position sensor that is in operable communication with the control system and that senses a position of the firing driver as the firing driver moves through the firing stroke. Based on the firing force reaching or exceeding the firing force threshold, the control system interrogates the position sensor to determine which of the first co-operative zone or the second co-operative zone that the firing driver is position.

The method 10430 further comprises controlling 10446 movement of at least one of the closure driver or the firing driver based on the determination. Based on the control system determining that the firing driver is in the first co-operative zone, the control system can control both the closure driver and the firing driver. Controlling movement of the firing driver and the closure driver can comprise pausing advancement of firing driver for an amount of time, retracting the firing driver toward a proximal position based on the amount of time elapsing, distally advancing the closure driver from the first position to a second position, and resuming advancement of the firing driver toward the distal position based on the closure driver reaching the second position.

Based on the control system determining that the firing driver is in the second co-operative zone, the control system can control the firing driver, but does not control movement of the closure driver. Controlling movement of the firing driver can comprise pausing advancement of firing driver for an amount of time and resuming advancement of the firing driver toward the fired position based on the amount of time elapsing.

As described elsewhere herein, the control system can leverage the closure system and the firing system, alone or in combination with each other, in order to reduce the force to fire the firing driver. The control system can make adjustments to the closure algorithm based on the amount of force that the cam surfaces of the firing driver experience during the firing stroke.

Figure 13:
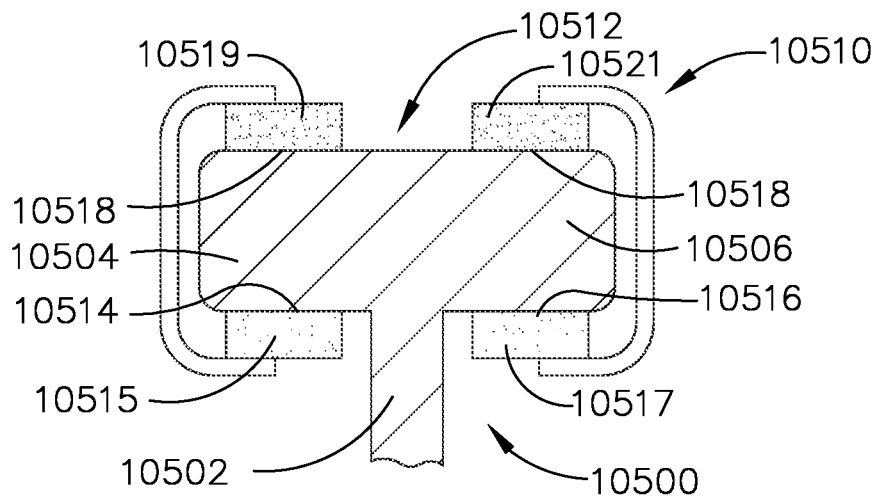
FIG. 13 illustrates a firing driver and an anvil, in accordance with the present disclosure.

Referring now to FIG. 13, a firing driver 10500 and an anvil 10510 are provided, in accordance with the present disclosure. The firing driver 10500 may be similar to firing driver 10024. The anvil 10510 may be similar to anvil 10006. The firing driver 10500 comprises a body 10502, a first flange 10504 extending from a first lateral side of the body 10502, and a second flange 10506 extending from a second lateral side of the body 10502. The body 10502 is sized to be received through a longitudinal slot defined in a staple cartridge, such as longitudinal slot 10020 of staple cartridge 10008, during a firing stroke of the firing driver 10500. The body 10502 can comprise a knife, similar to knife 10027, that is configured to cut tissue during the firing stroke of the firing driver 10500.

The anvil 10510 defines a channel 10512 that include a first lower wall 10514, a second lower wall 10516, a first upper wall 10518, and a second upper wall 10520. In use, the first flange 10504 and the second flange 10506 traverse through the channel 10512 during the firing stroke and engage the first lower wall 10514 and the second lower wall 10516, respectively, to maintain a spacing between the anvil 10510 and the staple cartridge during the firing stroke. The first flange 10504 and the second flange 10506 can engage the first upper wall 10518 and the second upper wall 10520, respectively, when tissue is over-compressed by a closure driver, such as closure tube 10013.

The anvil 10510 further comprises a first force sensor 10515 positioned at the first lower wall 10514, a second force sensor 10517 positioned at the second lower wall 10516, a third force sensor 10519 positioned at the first upper wall 10518, and a fourth force sensor 10521 positioned at the second upper wall 10520. The force sensors 10515, 10517, 10519, 10521 measure forces experienced at their respect walls 10514, 10516, 10518, 10520 by the flanges 10504, 10506 during the firing stroke of the firing driver 10500.

In operation, a control system, such as controller 10033 or controller 10051, receives force measurements from each of the force sensors 10515, 10517, 10519, 10521 in order to determine a clamping state of the anvil 10510. The clamping state can comprise an underclamped state where the first flange 10504 and the second flange 10506 ride along the lower walls 10514, 10516 of the channel 10512, which increases the firing force on the firing driver 10500. The clamping state can comprise an overclamped where the first flange 10504 and the second flange 10506 ride along the upper walls 10518, 10520 of the channel 10512, which increases the firing force on the firing driver 10500. Based on the determination of an underclamping state or an overclamping state, the closure system adjusts the closure algorithm accordingly, as discussed in more detail below.

Figure 14:
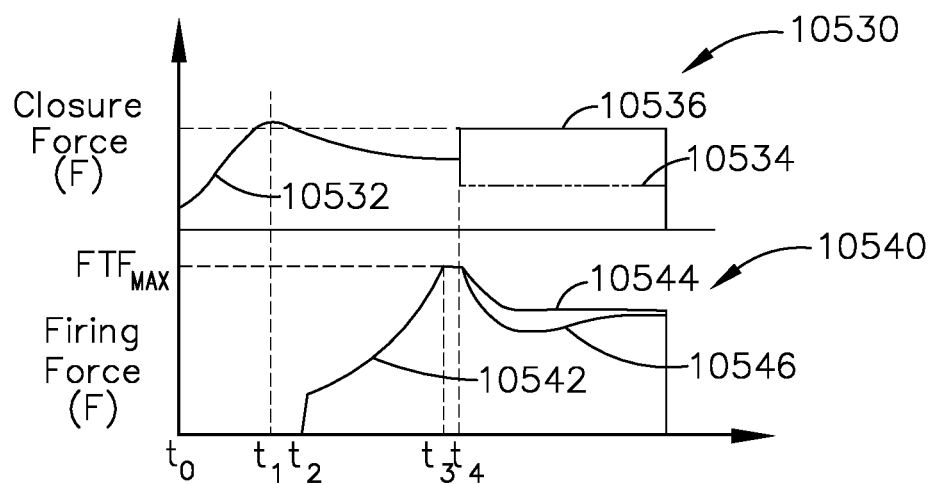
FIG. 14 is graphs for an exemplary firing stroke of the firing driver of FIG. 13 though the anvil of FIG. 13.

Referring now to FIG. 14, graphs 10530, 10540 are provided that illustrate an exemplary cutting and stapling operation with the firing driver 10500. Graph 10530 illustrates closure force applied by a closure driver, such as closure tube 10013, to a jaw of an end effector, such as anvil 10510, over time. Graph 10540 illustrates the firing force to drive the firing driver 10500 through a firing stroke over time.

At $t_0$, the closure driver is advanced distally to apply a closure force 10532 to the anvil 10510 to transition the anvil 10510 toward a closed position. The closure driver can be at a first position intermediate the proximal position and the distal position when the anvil 10510 has reached the closed position. The closure driver can halt advancement toward the distal position once a threshold amount of force has been applied to the tissue by the second jaw, thus preventing the tissue from being damaged. As such, the second jaw may be in a position intermediate the open position and the closed position (i.e., a partially closed or partially open position) when the closure driver halts advancement.

Once the closure driver stops advancing at $t_1$, an amount of time is allowed to elapse ($t_1$ to $t_2$) before the firing system is initiated. The amount of time can be a predefined amount of time stored in a memory and retrievable by the control system. The amount of time can be variable and a function of the length of the staple cartridge positioned in the end effector. The amount of time can be a function of the closure force applied to the tissue by the anvil 10510. For instance, the amount of time can correspond to the amount of time take for the closure force applied by the second jaw to drop a predefined amount, indicative of tissue thinning. The amount of time can be a function of how long it took the closure driver to place the anvil 10510 in the closed position. Other amounts of precompression time are described in more detail in U.S. patent application Ser. No. 17/957,946, which is hereby incorporated by reference in its entirety herein.

Once the amount of time has elapsed, at $t_2$, the control system actuates the firing system to advance the firing driver 10500 through its firing stroke. During the firing stroke, the first flange 10504 and the second flange 10506 traverse through the channel 10512 in the anvil 10510.

As the firing driver 10500 traverses through the firing stroke, the control system monitors the firing force 10542 of the firing driver 10500. The firing force can be measured using a force sensor on the firing driver 10500. The firing force can be measured using a current sensor that measures current through the firing motor that drives the firing driver 10500. Various other sensors for measuring the firing load on the firing driver and firing system are described elsewhere herein.

At $t_3$, the firing force 10542 reaches a firing force threshold $FTF_{MAX}$. The firing force threshold $FTF_{MAX}$ can be defined as the threshold that would result in a firing motor that drives the firing driver, such as firing motor 10056, stalling. The firing force threshold $FTF_{MAX}$ can be stored in a memory and retrievable by the control system. The firing force threshold $FTF_{MAX}$ can be based on the type of staple cartridge positioned in the end effector. The firing force threshold $FTF_{MAX}$ can be set by a user. Based on the firing force 10542 reaches a firing force threshold $FTF_{MAX}$, the control system determines a clamping state of the anvil 10510.

The control system can determine a clamping state of the anvil 10510 by evaluating the forces sensed by the upper force sensors 10519, 10521 and the lower force sensors 10515, 10517. The control system can compare the forces sensed by the upper force sensors 10519, 10521 to the forces sensed by the lower force sensors 10515, 10517. The control system can determine that the anvil 10510 is in an underclamped state based on the lower force sensors 10515, 10517 sensing forces that are a threshold amount greater than the to the forces sensed by the upper force sensors 10519, 10521. The control system can determine that the anvil 10510 is in an overclamped state based on the upper force sensors 10519, 10521 sensing forces that are a threshold amount greater than the to the forces sensed by the lower force sensors 10515, 10517. The threshold values for the comparisons can be stored in a memory and retrievable by the control system. The threshold values can be user defined. The control system can determine that the anvil 10510 is in an underclamped state based on the lower force sensors 10515, 10517 sensing forces that exceed a threshold value. The control system can determine that the anvil 10510 is in an overclamped state based on the upper force sensors 10519, 10521 sensing forces that exceed a threshold value.

Based on the determined clamping state of the anvil 10510, the control system adjusts the closure algorithm to change a position of the closure driver. Upon the determination of an overclamped state, the closure driver can be retracted proximally, which decreases the closure force 10532 to a first adjusted closure force 10534. Based on the adjustment, the firing force 10542 decreases to a first adjusted firing force 10544. Upon the determination of an underclamped state, the closure driver can be advanced distally, which increases the closure force 10532 to a second adjusted closure force 10536. Based on the adjustment, the firing force 10542 decreases to a second adjusted firing force 10546.

Figure 14A:
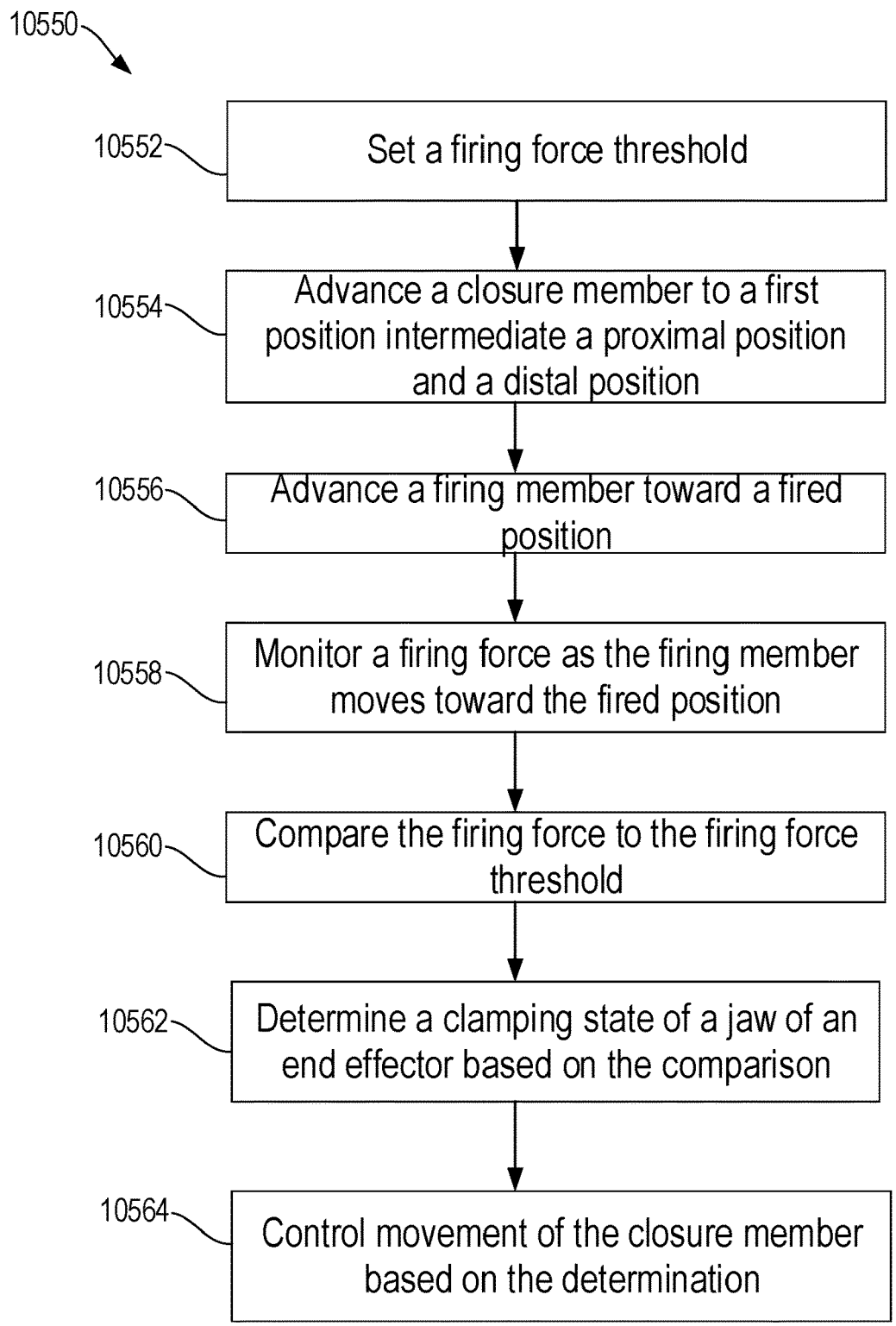
FIG. 14A is a method for controlling a surgical stapling instrument, in accordance with the present disclose.

Referring now to FIG. 14A, a method 10550 for controlling a surgical stapling system is provided, in accordance with the present disclosure. With reference now to FIG. 14A together with FIGS. 3 and 4, in accordance with the method 10550a control system, such as controller 10033 or controller 10051, sets 10552 a firing force threshold that is a threshold that would result in a firing motor, such as firing motor 10056, stalling. The control system can set a firing force threshold that is less than a maximum firing force threshold that would result in the firing motor stalling. How the control system sets a firing force threshold in accordance with the present disclosure are described elsewhere herein.

In accordance with the method 10550, the control system can advance 10552 a closure driver to a first position intermediate a proximal position and a distal position. The control system can actuate a closure motor, such as closure motor 10058, to advance a closure driver, such as closure tube 10013, distally.

In accordance with the method 10550, the control system can advance 10554 a firing driver toward a fired position. The control system can actuate a firing motor, such as firing motor 10056, which applies a firing force to a firing driver, such as firing driver 10024, to advance the firing driver distally.

In accordance with the method 10550, the control system can monitor 10558 the firing force as the firing driver moves toward the fired position. The surgical stapling system can include a force sensor, such sensor 10039 or sensor 10054, that senses the firing force that the firing motor applies to the firing driver.

In accordance with the method 10550, the control system can compare 10560 the firing force to the firing force threshold. The control system can be in operation communication with the force sensor and can receive the monitored firing force from the force sensor. The control system compares the firing force to the firing force threshold to determine if the firing force is below the firing force threshold or if the firing force has reached or exceeded the firing force threshold.

In accordance with the method 10550, the control system can determine 10562 a clamping state of a jaw of an end effector based on the comparison. As described elsewhere herein, the control system can determine a clamping state of a jaw, such as anvil 10510, by evaluating the forces sensed by upper force sensors 10519, 10521 and lower force sensors 10515, 10517 in a channel, such as channel 10512, of the jaw.

In accordance with the method 10550, the control system can control 10564 movement of the closure driver based on the determination. Based on the control system determining the clamping state of the jaw, the control system can adjust the closure algorithm to change a position of the closure driver. Upon the determination of an underclamped state, the closure driver can be distally advanced. Upon the determination of an overclamped state, the closure driver can be proximally retracted.

During parameterization of a surgical cutting and stapling device, the unloaded closure load and the unloaded firing load can be determined. The unloaded closure load can be the amount of force required to transition a jaw of an end effector, such as the second jaw 10006, from an open positon to a closed position. The unloaded firing load can be the amount of force required to move a firing driver, such as firing driver 10024, through a firing stroke. These values constitute a baseline for the surgical system to use. These baseline values can be stored in a memory, such as memory 10035 or memory 10053.

Additional functions could be included during the parameterization process. A "fake" staple cartridge can be inserted into an end effector, such as end effector 10002, and the end effector is actuated to grasp onto simulated tissue materials. One material of the simulated tissue materials is used to simulate an overstressed firing/closure condition and a second material of the simulated tissue materials is used to simulate an understressed firing/closure condition. The results of these three baseline simulations (unloaded, overstressed, and understressed) are used to influence final parameters of closure force thresholds, firing force thresholds and device specific frictional losses.

Furthermore, during parameterization, the surgical system may indicate that the maximum closure force is a threshold amount higher than nominal. As such, the surgical system is adjusted by shifting the maximum closure threshold according. Due to this closure threshold adjustment, the surgical system also adjusts the firing force thresholds to cooperate with the increased closure force. The adjustment to firing force threshold can be a proportional increase to the adjustment in the closure force threshold. The adjustment to firing force threshold can be a 1-to-1 adjustment to the adjustment in the closure force threshold. Based on the shifting maximum closure force threshold, the control system can also adjust the time in which a stall warning signal is provided. Based on the shifting maximum closure force threshold, the control system can also adjust parameters associated with the motor control algorithms. The parameters may include a maximum pulse width modulation signal to the motor controller, such as motor driver 10067, the acceleration of the firing driver by the firing system, or the pausing/pausing sequence in the firing algorithm, or combinations thereof. Other parameters associate with the motor control algorithms are discussed elsewhere herein.

Figures 15, 16:
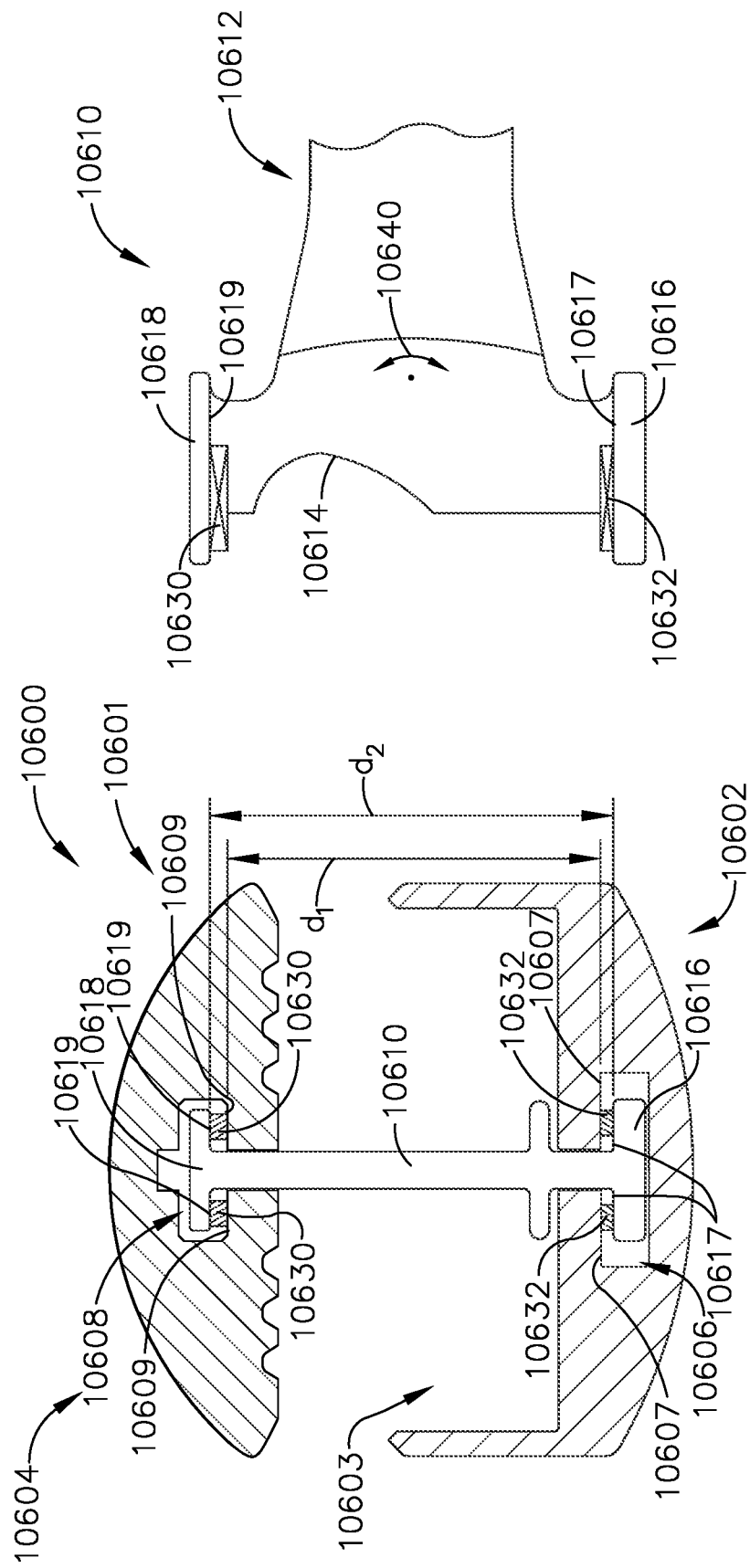
FIG. 15 illustrates a surgical stapling system, in accordance with the present disclosure.
FIG. 16 illustrates a side view of a firing driver and firing bar from FIG. 15, in accordance with the present disclosure.

Referring to FIGS. 15 and 16, a surgical stapling system 10600 including an end effector 10601 is provided, in accordance with the present disclosure. The end effector 10601 can be similar to end effector 10002. The end effector 10601 comprises a first jaw 10602 and a second jaw 10604. The first jaw 10602 comprises an elongate channel 10603 that is sized to receive a staple cartridge, such as staple cartridge 10008, therein. The second jaw 10604 comprises an anvil configured to deform staples ejected from the staple cartridge. The second jaw 10604 is pivotable relative to the first jaw 10602 between an open position and a closed position. The first jaw 10602 defines a first jaw channel 10606 that comprises first surfaces 10607 and the second jaw 10604 defines a second jaw channel 10608 that comprises second surfaces 10609. A first distance $d_1$ is defined between the first surfaces 10607 and the second surfaces 10609.

The surgical stapling system 10600 further comprises a firing driver 10610 and a firing bar 10612. The firing driver 10610 may be similar to firing driver 10024 and the firing bar 10612 may be similar to firing bar 10028. In use, the firing bar 10612 is driven by a firing system, such as firing motor 10056 and firing motor drive assembly 10057, to drive the firing driver 10610 through a firing stroke to deploy staples removably stored in the staple cartridge and to cut tissue captured by the end effector 10601 with a knife 10614, as discussed elsewhere herein. The firing bar 10612 can comprise a plurality of laminated strips.

The firing driver 10610 further includes a first cam 10616 and a second cam 10618. During the firing stroke, the first cam 10616 traverses the first jaw channel 10606 and the second cam traverses the second jaw channel 10608. The first cam 10616 and the second cam 10618 co-operatively maintain the end effector 10601 in the closed state by applying closure forces to the first surfaces 10607 and the second surfaces 10609, respectively. A second distance $d_2$ is defined between top surfaces 10617 of the first cam 10616 and bottom surfaces 10619 of the second cam 10618.

During the firing stroke, the firing driver 10610 may experience frictional resistance 10630 from the bottom surfaces 10619 of the second cam 10618 engaging and riding along the second surfaces 10609 of the second jaw channel 10608. Similarly, the firing driver 10610 may experience frictional resistance 10632 from the top surfaces 10617 of the first cam 10616 engaging and riding along the first surfaces 10617 of the first jaw channel 10606. As a result of these frictional forces 10630, 10632, the firing driver 10610 may rotate 10640, which will lead to an increase in the amount of force to fire the firing driver 10610.

During the parameterization process, the control system is calibrated with information regarding the end effector 10601 so as to know when the closure system and/or the firing system should be adjusted to regulate the firing force on the firing driver. The control system, such as controller 10033 or controller 10051, can be provided with distance $d_1$ and distance $d_2$. As shown in FIG. 15, $d_2$ is greater than $d_1$. Accordingly, the control system determines that there is a clearance between the surfaces 10617, 10619 and the surfaces 10607, 10609, which may lead to rotation of the firing driver 10610 during the firing stroke. This assembly level measurement of the end effector 10601 is integrated into the control system such that the control system has a better understanding of when the closure system algorithm and/or the firing system algorithm should be adjusted during the firing stroke of the firing driver. These assembly level measurements can be utilized to adjust firing zones of the firing driver. These assembly level measurements can be utilized to adjust the variable firing zones that are established based on the co-operation between the closure system and the firing system, as discussed elsewhere herein. These assembly level measurements can be utilized to adjust the predefined firing zones, such as the high co-operation zone $CZ_H$ and the low co-operation zone $CZ_L$, as discussed elsewhere herein. Any number of assembly level measurements can be incorporated into the control system to make adjustments to the co-operative zones of the firing driver. The assembly level measurements can comprise the height of the knife, the height of the firing driver, the height of the first jaw channel, or the height of the second jaw channel, or combinations thereof.

As described elsewhere herein, the control system can leverage the closure system and the firing system, alone or in combination with each other, in order to reduce the force to fire the firing driver. The control system can leverage the energy relief that the closure system provides in combination with pauses and pulsing in the firing algorithm to further reduce the force to fire the firing driver.

Figure 17:
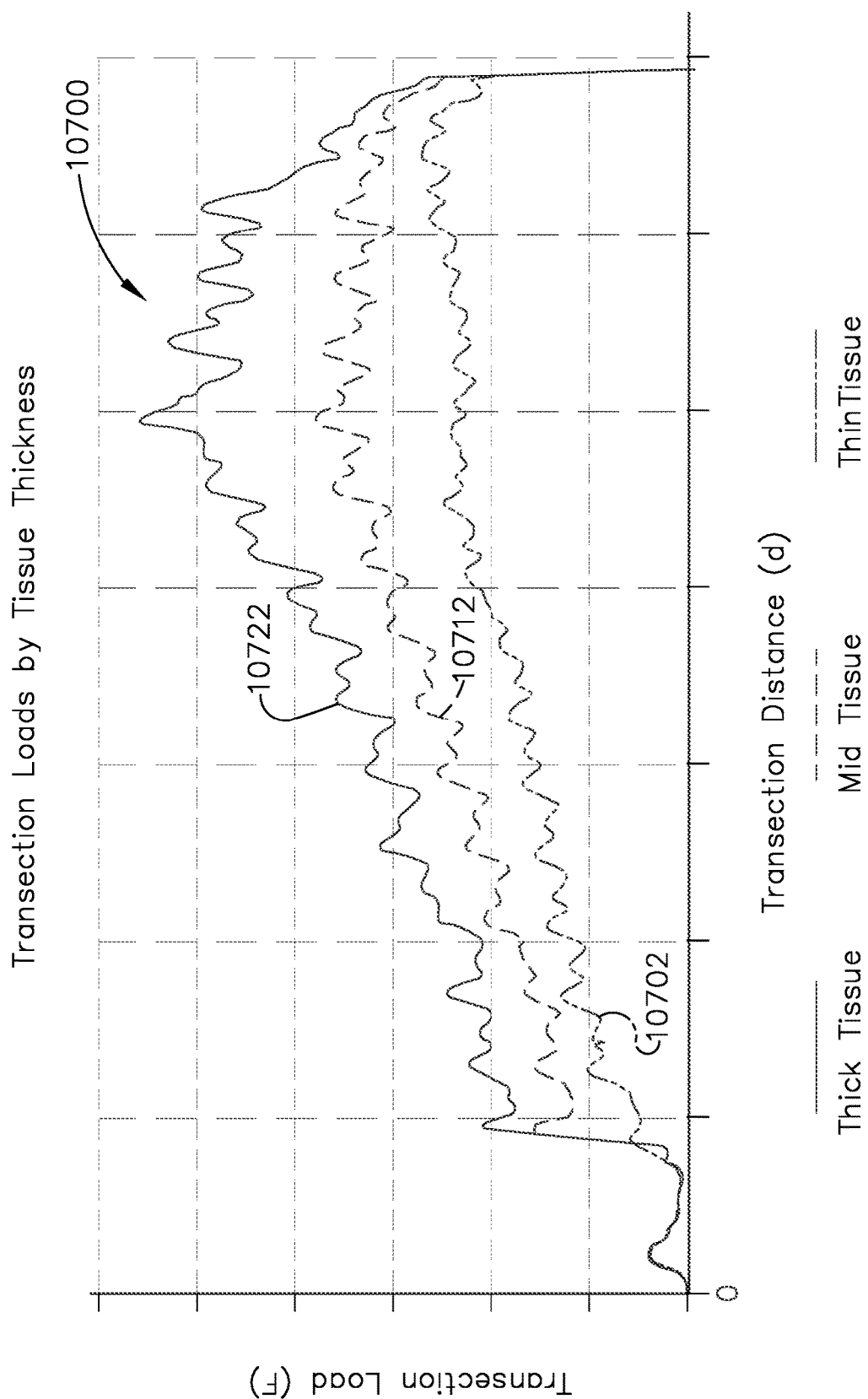
FIG. 17 is a graph that illustrates the relationship between firing force over time for various firing strokes of firing drivers for varying tissue thicknesses.

Referring now to FIG. 17, a graph 10700 is provided that illustrates the relationship between firing force over time for various firing strokes of firing drivers for varying tissue thicknesses. As shown in graph 10700, during a first firing stroke with a firing driver, such as firing driver 10024, through thin tissue, the firing force has a first firing force profile 10702. In the first firing force profile 10702, the force to fire the firing driver reaches a first firing force peak 10704. After the first firing force peak 10704, the force to fire the firing driver increases at a first rate.

During a second firing stroke with the firing driver, the firing force has a second firing force profile 10712 where the forces experienced are greater than in the first firing force profile 10702. In the second firing force profile 10712, the force to fire the firing driver reaches a second firing force peak 10714 that is greater than the first firing force peak 10704. After the second firing force peak 10714, the force to fire the firing driver increases at a second rate.

During a third firing stroke with the firing driver, the firing force has a third firing force profile 10722 where the forces experienced are greater than in the first firing force profile 10702 and the second firing force profile 10712. In the third firing force profile 10722, the force to fire the firing driver reaches a third firing force peak 10724 that is greater than the first firing force peak 10704 and the second firing force peak 10714. After the third firing force peak 10724, the force to fire the firing driver increases at a third rate.

The control system can predict the firing force profiles, such as the firing force profiles 10702, 10712, 10722, based on the initial firing force readings, such as the initial firing force peaks 10704, 10714, 10724, the rate at which the firing force changes from the initial firing force peaks, or the number of hills and valleys detected in the firing force profile after an amount of time has elapsed from the initial firing force peaks 10704, 10714, 10724, or a combination thereof. Based on the prediction, the control system adjusts the closure algorithm and/or firing algorithm, as discussed elsewhere herein, to reduce the firing force profile later in the transection cycle.

A staple cartridge can be inserted into a first jaw, such as first jaw 10004, of an end effector, such as end effector 10002. The end effector is then utilized to grasp tissue within the jaws of the end effector. In particular, a closure driver, such as closure tube 10013, is advanced distally to apply a closure force to a second jaw, such as second jaw 10006, to transition the second jaw toward the closed position. A firing system, such as firing motor 10056 and firing motor drive assembly 10057, then advances a firing driver, such as firing driver 10024, through its firing stroke to deploy staples from the staple cartridge and cut the tissue captured by the end effector.

As the firing driver is advanced through its firing stroke, the control system monitors the firing force of the firing driver. The firing force can be measured using a force sensor on the firing driver. The firing force can be measured using a current sensor that measures current through the firing motor that drives the firing driver. Various other sensors for measuring the firing load on the firing driver and firing system are described elsewhere herein.

At a point in the firing stroke of the firing driver, the control system detects an initial firing force peak. The initial firing force peak can be indicative of the firing driver beginning to transect the tissue captured by the end effector. The initial firing force peak can be indicative of the firing driver beginning to deploy staples from the staple cartridge.

Based on the detection, the control system compares the initial firing force peak value to threshold values stored in a memory, such as a memory 10053. The threshold values can correspond to the force values that are expected of different tissue thicknesses. Should the initial firing force peak value exceed a first threshold value but remain below a second threshold force value greater than the first threshold value, the control system can determine that thin tissue is positioned within the jaws of the end effector. Should the initial firing force peak value exceed the second threshold value but remain below a third threshold force value greater than the second threshold value, the control system can determine that medium tissue is positioned within the jaws of the end effector. Should the initial firing force peak value exceed the third threshold value, the control system can determine that thick tissue is positioned within the jaws of the end effector. Based on the comparison, the control system predicts future firing forces that are expected to be experienced by the firing driver during the firing stroke.

After the detection of the initial firing force peak, the control system can detect the rate at which the firing force increases from the initial firing force peak. Based on the initial firing force peak and the rate at which the firing force increases from the initial firing force peak, the control system predicts future forces to fire in the firing stroke. The control system can detect the number of peak and valleys in the firing force over a portion of the firing stroke after the initial firing force peak. Based on the initial firing force peak and the number of peaks and valleys detected, the control system predicts future forces to fire in the firing stroke.

Based on the prediction, the control system can adjust the closure algorithm to displace the closure driver. Upon the determination of thin tissue being positioned in the jaws of the end effector, the control system can advance the closure driver a first amount. Upon the determination of medium tissue being positioned in the jaws of the end effector, the control system can advance the closure driver a second amount different than the first amount. The second amount can be greater than the first amount. Upon the determination of thick tissue being positioned in the jaws of the end effector, the control system can advance the closure driver a third amount which is different than the second amount. The third amount can be greater than the second amount.

Based on the prediction, the control system can set zones for the firing stroke, where the zones comprise lengths of the firing stroke where the closure algorithm is exclusively adjusted, the firing algorithm is exclusively adjusted, or a combination of both the closure algorithm and the firing algorithm are adjusted, as discussed elsewhere herein.

Based on the prediction, the control system can adjust predefined zones, such as the high co-operative zone $CZ_H$ and the low co-operative zone $CZ_L$ for the firing stroke. Based on the prediction, the control system can adjust the closure algorithm and/or the firing algorithm for different portions of the firing stroke. Based on the prediction, the control system can adjust the length and the number of occurrences of pauses of the firing driver during the firing stroke.

Accordingly, based on a prediction from an early portion of the, the control system is able to make adjustments that will result in lower forces to fire later in the firing stroke.

Many of the surgical instrument systems described herein are motivated by an electric motor; however, the surgical instrument systems described herein can be motivated in any suitable manner. The surgical instrument systems described herein can be motivated by a manually-operated trigger, for example. The motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

Various aspects of the subject matter described herein are set out in the following numbered examples:

Example 1—A surgical stapling system (10000) comprising an end effector (10002), a closure driver (10013) movable to rotate the second jaw relative to the first jaw, a closure motor (10058) to drive the closure driver, a firing driver (10024) movable from an unfired position toward a fired position during a firing stroke, a firing motor (10056) to apply a firing force to the firing driver, a force sensor (10039, 10054) to sense the firing force applied by the firing motor, and a control circuit (10032, 10051) coupleable with the closure motor, the firing motor, and the force sensor. The end effector comprises a first jaw (10004) and a second jaw (10006) rotatable relative to the first jaw. The control circuit is to set a firing force threshold, advance the closure driver to a first position, advance the firing driver, monitor the firing force as the firing driver is advanced, compare the firing force to the firing force threshold, and control movement of at least one of the closure driver or the firing driver based on results of the compare and a zone in which the firing driver is positioned.

Example 2—The surgical stapling system of Example 1, wherein the control circuit is to monitor a relationship between the closure driver and the firing driver as the firing driver is advanced. To set the firing force threshold, the control circuit is to set an initial firing force threshold and adjust the initial firing force threshold to a first adjusted firing force threshold based on the monitored relationship between the closure driver and the firing driver.

Example 3—The surgical stapling system of Example 2, wherein to monitor the relationship between the closure driver and the firing driver, the control circuit is to monitor an amount of co-operation that exists between the closure driver and the firing driver to maintain the second jaw in a closed position.

Example 4—The surgical stapling system of Example 3, wherein the closure driver is to apply a first closure force to the second jaw and the firing driver is to apply a second closure force to the second jaw. The surgical stapling system further comprises a first closure force sensor (10039, 10054) to sense the first closure force and a second closure force sensor (10039, 10054) to sense the second closure force. The control circuit is to receive the first closure force from the first closure force sensor, receive the second closure force from the second closure force sensor, and monitor the amount of co-operation that exists between the closure driver and the firing driver based on a ratio of the first closure force to the second closure force.

Example 5—The surgical stapling system of Example 4, wherein the control circuit is to determine a zone from a plurality of zones that the firing driver is located. The zones comprise a first firing zone and a second firing zone. The firing driver is determined to be in the first firing zone based on the first closure force being greater than or equal to the second closure force. The firing driver is determined to be in the second firing zone based on the second closure force being greater than the first closure force.

Example 6—The surgical stapling system of Example 5, wherein the control circuit is to set a threshold co-operation value, wherein the zones comprise a third firing zone, and wherein the firing driver is determined to be in the third firing zone based on the ratio of the first closure force to the second closure force reaching or dropping below the threshold co-operation value.

Example 7—The surgical stapling system of Example 6, wherein the control circuit is to adjust the initial firing force threshold to the first adjusted firing force threshold based on the second closure force being greater than the first closure force. The control circuit is to control movement of the closure driver and not control movement of the firing driver based on the monitored firing force reaching the initial firing force threshold and the firing driver being positioned in the first firing zone. The control circuit is to control movement of the closure driver and the firing driver based on the monitored firing force reaching the first adjusted firing force threshold and the firing driver being positioned in the second firing zone.

Example 8—The surgical stapling system of Example 7, wherein to set the firing force threshold, the control circuit is to adjust the first adjusted firing force threshold to a second adjusted firing force threshold based on the monitored relationship between the closure driver and the firing driver, and wherein the control circuit is to control movement of the firing driver and not control movement of the closure driver based on the firing force reaching the second adjusted firing force threshold and the firing driver being positioned in the third firing zone.

Example 9—The surgical stapling system of Example 1, wherein the control circuit is to set a first co-operative zone ($CZ_H$) defined over a first portion of the firing stroke and a second co-operative zone ($CZ_L$) defined over a second portion of the firing stroke distal to the first portion of the firing stroke.

Example 10—The surgical stapling system of Example 9, further comprising a position sensor (10039, 10054) coupleable with the control circuit. The position sensor is to sense a position of the firing driver. The control circuit is to determine if the firing driver is in the first co-operative zone or the second co-operative zone and control movement of both the closure driver and the firing driver based on the firing force reaching the firing force threshold and the firing driver being in the first co-operative zone.

Example 11—The surgical stapling system of Example 10, wherein to control movement of the firing driver, the control circuit is to pause advancement of firing driver for an amount of time and retract the firing driver toward a proximal position based on the amount of time elapsing.

Example 12—The surgical stapling system of Example 11, wherein to control movement of the closure driver, the control circuit is to distally advancing the closure driver from the first position to a second position.

Example 13—The surgical stapling system of Example 12, wherein to control movement of the firing driver, the control circuit is to resume advancement of the firing driver toward the distal position based on the closure driver reaching the second position.

Example 14—The surgical stapling system of Example 12, wherein the control circuit is to control movement of the firing driver and not control movement of the closure driver based on the firing force reaching the firing force threshold and the firing driver being in the second co-operative zone.

Example 15—The surgical stapling system of Example 16, wherein to control movement of the firing driver, the control circuit is to pause advancement of firing driver for an amount of time and resume advancement of the firing driver toward the fired position based on the amount of time elapsing.

Example 16—A surgical stapling system (10000) comprising an end effector (10002), a closure driver (10013) movable to rotate the second jaw relative to the first jaw, a closure motor (10058) to drive the closure driver, a firing driver (10024, 10500) movable from an unfired position toward a fired position during a firing stroke, a firing motor (10056) to apply a firing force to the firing driver, a third force sensor (10039, 10054) to sense the firing force applied by the firing motor, and a control circuit (10032, 10051). The end effector comprises a first jaw (10004) and a second jaw (10006, 10510) rotatable relative to the first jaw. The second jaw defines a channel (10512). The channel comprises an upper wall (10518) comprising a first force sensor (10519) and a lower wall (10514) comprising a second force sensor (10515). The firing driver comprises a flange (10504) to traverse the channel during the firing stroke. The first force sensor is to sense a first force the flange applies to the upper wall. The second force sensor is to sense a second force the flange applies to the lower wall. The control circuit is coupleable with the closure motor, the firing motor, the first force sensor, the second force sensor, and the third force sensor. The control circuit is to set a firing force threshold, advance the closure driver to a first position, advance the firing driver toward the fired position, monitor the firing force as the firing driver is advanced, compare the firing force to the firing force threshold, determine a clamping state of the second jaw based on results of the compare, and control movement of the closure driver based on results of the determine.

Example 17—The surgical stapling system of Example 16, wherein to determine the clamping state of the second jaw, the control circuit is to evaluate the first force that the flange applies to the upper wall and the second force that the flange applies to the lower wall.

Example 18—The surgical stapling system of Example 16, wherein to control movement of the closure driver, the control circuit is to advance the closure driver based on a determined underclamped state.

Example 19—The surgical stapling system of Example 16, wherein to control movement of the closure driver, the control circuit is to retract the closure driver based on a determined overclamped state.

Example 20—A surgical stapling system comprising an end effector, a closure driver movable to rotate the second jaw relative to the first jaw, a closure motor to drive the closure driver, a firing driver movable from an unfired position toward a fired position during a firing stroke, a firing motor to apply a firing force to the firing driver, a force sensor to sense the firing force applied by the firing motor, and a control circuit coupleable with the closure motor, the firing motor, and the force sensor. The end effector comprises a first jaw and a second jaw rotatable relative to the first jaw. The control circuit is to set a firing force threshold, advance the closure driver to a first position, advance the firing driver, monitor the firing force as the firing driver is advanced, compare the firing force to the firing force threshold, and control movement of at least one of the closure driver or the firing driver based on results of the compare and a zone in which the firing driver is positioned.

Example 21—The surgical stapling system of Example 20, wherein the control circuit is to monitor a relationship between the closure driver and the firing driver as the firing driver is advanced. To set the firing force threshold, the control circuit is to set an initial firing force threshold and adjust the initial firing force threshold to a first adjusted firing force threshold based on the monitored relationship between the closure driver and the firing driver.

Example 22—The surgical stapling system of Example 21, wherein to monitor the relationship between the closure driver and the firing driver, the control circuit is to monitor an amount of co-operation that exists between the closure driver and the firing driver to maintain the second jaw in a closed position.

Example 23—The surgical stapling system of Example 22, wherein the closure driver is to apply a first closure force to the second jaw and the firing driver is to apply a second closure force to the second jaw. The surgical stapling system further comprises a first closure force sensor to sense the first closure force and a second closure force sensor to sense the second closure force. The control circuit is to receive the first closure force from the first closure force sensor, receive the second closure force from the second closure force sensor, and monitor the amount of co-operation that exists between the closure driver and the firing driver based on a ratio of the first closure force to the second closure force.

Example 24—The surgical stapling system of Example 23, wherein the control circuit is to determine a zone from a plurality of zones that the firing driver is located. The zones comprise a first firing zone and a second firing zone. The firing driver is determined to be in the first firing zone based on the first closure force being greater than or equal to the second closure force. The firing driver is determined to be in the second firing zone based on the second closure force being greater than the first closure force.

Example 25—The surgical stapling system of Example 24, wherein the control circuit is to set a threshold co-operation value. The zones comprise a third firing zone. The firing driver is determined to be in the third firing zone based on the ratio of the first closure force to the second closure force reaching or dropping below the threshold co-operation value.

Example 26—The surgical stapling system of Example 25, wherein the control circuit is to adjust the initial firing force threshold to the first adjusted firing force threshold based on the second closure force being greater than the first closure force. The control circuit is to control movement of the closure driver and not control movement of the firing driver based on the monitored firing force reaching the initial firing force threshold and the firing driver being positioned in the first firing zone. The control circuit is to control movement of the closure driver and the firing driver based on the monitored firing force reaching the first adjusted firing force threshold and the firing driver being positioned in the second firing zone.

Example 27—The surgical stapling system of Example 26, wherein the control circuit is to adjust the initial firing force threshold to the first adjusted firing force threshold based on the firing driver entering the second firing zone.

Example 28—The surgical stapling system of Example 26, wherein to set the firing force threshold, the control circuit is to adjust the first adjusted firing force threshold to a second adjusted firing force threshold based on the monitored relationship between the closure driver and the firing driver. The control circuit is to control movement of the firing driver and not control movement of the closure driver based on the firing force reaching the second adjusted firing force threshold and the firing driver being positioned in the third firing zone.

Example 29—The surgical stapling system of Example 28, wherein the control circuit is to adjust the first adjusted firing force threshold to the second adjusted firing force threshold based on the firing driver entering the third firing zone.

Example 30—The surgical stapling system of Example 20, wherein the control circuit is to set a first co-operative zone defined over a first portion of the firing stroke and a second co-operative zone defined over a second portion of the firing stroke distal to the first portion of the firing stroke.

Example 31—The surgical stapling system of Example 30, further comprising a position sensor coupleable with the control circuit. The position sensor is to sense a position of the firing driver. The control circuit is to determine if the firing driver is in the first co-operative zone or the second co-operative zone and control movement of both the closure driver and the firing driver based on the firing force reaching the firing force threshold and the firing driver being in the first co-operative zone.

Example 32—The surgical stapling system of Example 31, wherein to control movement of the firing driver, the control circuit is to pause advancement of firing driver for an amount of time and retract the firing driver toward a proximal position based on the amount of time elapsing.

Example 33—The surgical stapling system of Example 32, wherein to control movement of the closure driver, the control circuit is to distally advancing the closure driver from the first position to a second position.

Example 34—The surgical stapling system of Example 33, wherein to control movement of the firing driver, the control circuit is to resume advancement of the firing driver toward the distal position based on the closure driver reaching the second position.

Example 35—The surgical stapling system of Example 31, wherein the control circuit is to control movement of the firing driver and not control movement of the closure driver based on the firing force reaching the firing force threshold and the firing driver being in the second co-operative zone.

Example 36—The surgical stapling system of Example 35, wherein to control movement of the firing driver, the control circuit is to pause advancement of firing driver for an amount of time and resume advancement of the firing driver toward the fired position based on the amount of time elapsing.

Example 37—A surgical stapling system comprising an end effector, a closure driver movable to rotate the second jaw relative to the first jaw, a closure motor to drive the closure driver, a firing driver movable from an unfired position toward a fired position during a firing stroke, a firing motor to apply a firing force to the firing driver, a third force sensor to sense the firing force applied by the firing motor, and a control circuit coupleable with the closure motor, the firing motor, the first force sensor, the second force sensor, and the third force sensor. The end effector comprises a first jaw and a second jaw rotatable relative to the first jaw. The second jaw defines a channel. The channel comprises an upper wall comprising a first force sensor and a lower wall comprising a second force sensor. The firing driver comprises a flange to traverse the channel during the firing stroke. The first force sensor is to sense a first force the flange applies to the upper wall. The second force sensor is to sense a second force the flange applies to the lower wall. The control circuit is to set a firing force threshold, advance the closure driver to a first position, advance the firing driver toward the fired position, monitor the firing force as the firing driver is advanced, compare the firing force to the firing force threshold, determine a clamping state of the second jaw based on results of the compare, and control movement of the closure driver based on results of the determine.

Example 38—The surgical stapling system of Example 37, wherein to determine the clamping state of the second jaw, the control circuit is to evaluate the first force that the flange applies to the upper wall and the second force that the flange applies to the lower wall.

Example 39—The surgical stapling system of Example 38, wherein to control movement of the closure driver, the control circuit is to advance the closure driver based on a determined underclamped state and retract the closure driver based on a determined overclamped state.

The entire disclosures of U.S. Pat. No. 11,589,865, entitled METHODS FOR CONTROLLING A POWERED SURGICAL STAPLER THAT HAS SEPARATE ROTARY CLOSURE AND FIRING SYSTEMS, which issued on Feb. 28, 2023, U.S. Pat. No. 6,978,921, entitled SURGICAL STAPLING INSTRUMENT INCORPORATING AN E-BEAM FIRING MECHANISM, which issued on Dec. 27, 2005, U.S. Pat. No. 10,213,203, entitled STAPLE CARTRIDGE ASSEMBLY WITHOUT A BOTTOM COVER, which issued on Feb. 26, 2019, U.S. Pat. No. 10,945,727, entitled STAPLE CARTRIDGE WITH DEFORMABLE DRIVER RETENTION FEATURES, which issued on Mar. 16, 2021, U.S. Pat. No. 11,234,698, entitled STAPLING SYSTEM COMPRISING A CLAMP LOCKOUT AND A FIRING LOCKOUT, which issued on Feb. 1, 2022, U.S. Pat. No. 11,540,826, entitled SURGICAL STAPLER END EFFECTOR SLED HAVING CARTRIDGE WALL SUPPORT FEATURE, which issued on Jan. 3, 2023, U.S. Pat. No. 10,299,792, entitled FASTENER CARTRIDGE COMPRISING NON-UNIFORM FASTENERS, which issued on May 28, 2019, U.S. Pat. No. 8,540,133, entitled STAPLE CARTRIDGE, which issued on Sep. 24, 2013, U.S. Pat. No. 9,788,835, entitled DEVICES AND METHODS FOR FACILITATING EJECTION OF SURGICAL FASTENERS FROM CARTRIDGES, which issued on Oct. 17, 2017, U.S. Pat. No. 10,105,142, entitled SURGICAL STAPLER WITH PLURALITY OF CUTTING ELEMENTS, which issued on Oct. 23, 2018, U.S. Pat. No. 10,537,324, entitled STEPPED STAPLE CARTRIDGE WITH ASYMMETRICAL STAPLES, which issued on Jan. 21, 2020, U.S. Pat. No. 7,669,746, entitled STAPLE CARTRIDGES FOR FORMING STAPLES HAVING DIFFERING FORMED STAPLE HEIGHTS, which issued on Mar. 2, 2010, U.S. Pat. No. 8,123,100, entitled SURGICAL STAPLING INSTRUMENTS INCLUDING A CARTRIDGE HAVING MULTIPLE STAPLE SIZES, which issued on Feb. 28, 2012, U.S. Pat. No. 7,407,075, entitled STAPLE CARTRIDGE HAVING MULTIPLE STAPLE SIZES FOR A SURGICAL STAPLING INSTRUMENT, which issued on Aug. 5, 2008, U.S. Pat. No. 10,085,749, entitled SURGICAL APPARATUS WITH CONDUCTOR STRAIN RELIEF, which issued on Oct. 2, 2018, U.S. Pat. No. 10,765,427, entitled METHOD FOR ARTICULATING A SURGICAL INSTRUMENT, which issued on Sep. 8, 2020, U.S. Pat. No. 11,291,445, entitled SURGICAL STAPLE CARTRIDGES WITH INTEGRAL AUTHENTICATION KEYS, which issued on Apr. 5, 2022, U.S. Pat. No. 8,864,007, entitled IMPLANTABLE FASTENER CARTRIDGE HAVING A NON-UNIFORM ARRANGEMENT, which issued on Oct. 21, 2014, U.S. Pat. No. 11,490,890, entitled COMPRESSIBLE NON-FIBROUS ADJUNCTS, which issued on Nov. 8, 2022, U.S. Pat. No. 10,952,724, entitled THREE DIMENSIONAL ADJUNCTS, which issued on Mar. 23, 2021, U.S. Pat. No. 9,770,245, entitled LAYER ARRANGEMENTS FOR SURGICAL STAPLE CARTRIDGES, which issued on Sep. 26, 2017, U.S. Pat. No. 10,123,798, entitled TISSUE THICKNESS COMPENSATOR COMPRISING CONTROLLED RELEASE AND EXPANSION, which issued on Nov. 13, 2018, U.S. Pat. No. 10,166,023, entitled METHOD OF APPLYING A BUTTRESS TO A SURGICAL STAPLER END EFFECTOR, which issued on Jan. 1, 2019, U.S. Pat. No. 11,207,065, entitled METHOD FOR FABRICATING SURGICAL STAPLER ANVILS, which issued on Dec. 28, 2021, U.S. Pat. No. 8,141,762, entitled SURGICAL STAPLER COMPRISING A STAPLE POCKET, which issued on Mar. 27, 2012, U.S. Pat. No. 8,876,857, entitled END EFFECTOR WITH REDUNDANT CLOSING MECHANISMS, which issued on Nov. 4, 2014, U.S. Pat. No. 9,629,631, entitled COMPOSITE DRIVE BEAM FOR SURGICAL STAPLING, which issued on Apr. 25, 2017, U.S. Patent Application Publication No. 2022/0346858, entitled METHOD FOR OPERATING A SURGICAL INSTRUMENT INCLUDING SEGMENTED ELECTRODES, which published on Nov. 3, 2022, U.S. Patent Application Publication No. 2022/0304680, entitled DRIVERS FOR FASTENER CARTRIDGE ASSEMBLIES HAVING ROTARY DRIVE SCREWS, which published on Sep. 29, 2022, U.S. Patent Application Publication No. 2022/

0304679, entitled METHOD OF USING A POWERED STAPLING DEVICE, which published on Sep. 29, 2022, U.S. Patent Publication No. 2019/0298350, entitled METHODS FOR CONTROLLING A POWERED SURGICAL STAPLER THAT HAS SEPARATE ROTARY CLOSURE AND FIRING SYSTEMS, which published on Oct. 3, 2019, U.S. Patent Application Publication No. 2017/0367695, entitled STAPLE CARTRIDGE COMPRISING WIRE STAPLES AND STAMPED STAPLES, which published on Dec. 28, 2017, U.S. Patent Application Publication No. 2015/0134077, entitled SEALING MATERIALS FOR USE IN SURGICAL STAPLING, which published on May 14, 2015, U.S. Patent Application Publication No. 2018/0168615, entitled METHOD OF DEFORMING STAPLES FROM TWO DIFFERENT TYPES OF STAPLE CARTRIDGES WITH THE SAME SURGICAL STAPLING INSTRUMENT, which published on Jun. 21, 2018, U.S. Patent Application Publication No. 2018/0132849, entitled STAPLE FORMING POCKET CONFIGURATIONS FOR CIRCULAR SURGICAL STAPLER ANVIL, which published on May 17, 2018, U.S. Patent Application Publication No. 2018/0168613, entitled SURGICAL INSTRUMENTS WITH JAWS THAT ARE PIVOTABLE ABOUT A FIXED AXIS AND INCLUDE SEPARATE AND DISTINCT CLOSURE AND FIRING SYSTEMS, which published on Jun. 21, 2018, U.S. Patent Application Publication No. 2017/0319205, entitled POWERED END EFFECTOR ASSEMBLY WITH PIVOTABLE CHANNEL, which published on Nov. 9, 2017, U.S. Patent Application Publication No. 2014/0001231, entitled FIRING SYSTEM LOCKOUT ARRANGEMENTS FOR SURGICAL INSTRUMENTS, which published on Jan. 2, 2014, U.S. Patent Application Publication No. 2016/0095596, entitled APPARATUS FOR ENDOSCOPIC PROCEDURES, which published on Apr. 7, 2016, U.S. Patent Application Publication No. 2015/0297199, entitled ADAPTER ASSEMBLY WITH GIMBAL FOR INTERCONNECTING ELECTROMECHANICAL SURGICAL DEVICES AND SURGICAL LOADING UNITS, AND SURGICAL SYSTEMS THEREOF, which published on Oct. 22, 2015, U.S. Patent Application Publication No. 2022/0031351, entitled SURGICAL INSTRUMENTS WITH DIFFERENT ARTICULATION JOINT ARRANGEMENTS FOR ACCOMMODATING FLEXIBLE ACTUATORS, which published on Feb. 3, 2022, U.S. Patent Application Publication No. 2022/0031320, entitled SURGICAL INSTRUMENTS WITH FLEXIBLE FIRING MEMBER ACTUATOR CONSTRAINT ARRANGEMENTS, which published on Feb. 3, 2022, U.S. Patent Application Publication No. 2023/0119119, entitled CABLE-DRIVEN ACTUATION SYSTEM FOR ROBOTIC SURGICAL TOOL ATTACHMENT, which published on Apr. 20, 2023, International Patent Publication No. WO2018/071497, entitled STAPLER CARTRIDGE WITH AN INTEGRAL KNIFE, which published on Apr. 18, 2018, International Patent Publication No. WO2018/049211, entitled WRIST ARCHITECTURE, which published on Mar. 15, 2018, U.S. Pat. No. 11,298,129, entitled METHOD FOR PROVIDING AN AUTHENTICATION LOCKOUT IN A SURGICAL STAPLER WITH A REPLACEABLE CARTRIDGE, which issued on Apr. 12, 2022, U.S. Pat. No. 10,898,183, entitled ROBOTIC SURGICAL INSTRUMENT WITH CLOSED LOOP FEEDBACK TECHNIQUES FOR ADVANCEMENT OF CLOSURE MEMBER DURING FIRING, which issued on Jan. 26, 2021, U.S. Pat. No. 5,485,947, entitled LINEAR STAPLING MECHANISM WITH CUTTING MEANS, which issued on Jan. 23, 1996, International Patent Publication No. WO2018/049206, entitled STAPLER RELOAD DETECTION AND IDENTIFICATION, which published on Mar. 15, 2018, U.S. Patent Application Publication No. 2016/0249920, entitled Surgical fastener applying apparatus, which published on Sep. 1, 2016, U.S. Design Pat. No. D974,560, entitled STAPLE CARTRIDGE, which issued on Jan. 3, 2023, U.S. Design Pat. No. D967,421, entitled STAPLE CARTRIDGE, which issued on Oct. 18, 2022, U.S. Design Pat. No. D933,220, entitled BUTTRESS ASSEMBLY FOR A SURGICAL STAPLER, which issued on Oct. 12, 2021, U.S. Pat. No. 9,839,420, entitled TISSUE THICKNESS COMPENSATOR COMPRISING AT LEAST ONE MEDICAMENT, which issued on Dec. 12, 2017, U.S. Pat. No. 10,588,623, entitled ADHESIVE FILM LAMINATE, which issued on Mar. 17, 2020, U.S. Pat. No. 8,499,992, entitled DEVICE AND METHOD FOR CONTROLLING COMPRESSION OF TISSUE, which issued on Aug. 6, 2013, U.S. Patent Application Publication No. 2022/0378427, entitled STAPLING INSTRUMENT COMPRISING JAW MOUNTS, which published on Dec. 1, 2022, U.S. Pat. No. 10,349,939, entitled METHOD OF APPLYING A BUTTRESS TO A SURGICAL STAPLER, which issued on Jul. 16, 2019, U.S. Pat. No. 9,386,988, entitled RETAINER ASSEMBLY INCLUDING A TISSUE THICKNESS COMPENSATOR, which issued on Jul. 12, 2016, U.S. Pat. No. 9,072,535, entitled SURGICAL STAPLING INSTRUMENTS WITH ROTATABLE STAPLE DEPLOYMENT ARRANGEMENTS, which issued on Jul. 7, 2015, and U.S. Pat. No. 9,844,369, entitled, SURGICAL END EFFECTORS WITH FIRING ELEMENT MONITORING ARRANGEMENTS, which issued on Dec. 19, 2017 are incorporated by reference herein.

The entire disclosures of:
U.S. Pat. No. 5,403,312, entitled ELECTROSURGICAL HEMOSTATIC DEVICE, which issued on Apr. 4, 1995;
U.S. Pat. No. 7,000,818, entitled SURGICAL STAPLING INSTRUMENT HAVING SEPARATE DISTINCT CLOSING AND FIRING SYSTEMS, which issued on Feb. 21, 2006;
U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;
U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;
U.S. Pat. No. 7,670,334, entitled SURGICAL INSTRUMENT HAVING AN ARTICULATING END EFFECTOR, which issued on Mar. 2, 2010;
U.S. Pat. No. 7,753,245, entitled SURGICAL STAPLING INSTRUMENTS, which issued on Jul. 13, 2010;
U.S. Pat. No. 8,393,514, entitled SELECTIVELY ORIENTABLE IMPLANTABLE FASTENER CARTRIDGE, which issued on Mar. 12, 2013;
U.S. patent application Ser. No. 11/343,803, entitled SURGICAL INSTRUMENT HAVING RECORDING CAPABILITIES, now U.S. Pat. No. 7,845,537;
U.S. patent application Ser. No. 12/031,573, entitled SURGICAL CUTTING AND FASTENING INSTRUMENT HAVING RF ELECTRODES, filed Feb. 14, 2008;
U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

While several configurations have been described, additional modifications are within the scope of the present disclosure, which is intended to cover any variations, uses, or adaptations of the disclosed configurations using its general principles.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" or "control system" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

It is worthy to note that any reference numbers included in the appended claims are used to reference exemplary embodiments/elements described in the present disclosure. Accordingly, any such reference numbers are not meant to limit the scope of the subject matter recited in the appended claims.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical stapling system, comprising:
   an end effector, comprising:
      a first jaw; and
      a second jaw rotatable relative to the first jaw;
   a closure driver movable to rotate the second jaw relative to the first jaw;
   a closure motor to drive the closure driver;
   a firing driver movable from an unfired position toward a fired position during a firing stroke;
   a firing motor to apply a firing force to the firing driver;
   a force sensor to sense the firing force applied by the firing motor; and
   a control circuit coupleable with the closure motor, the firing motor, and the force sensor, wherein the control circuit is to:
      set a firing force threshold;
      advance the closure driver to a first position;
      advance the firing driver;
      monitor the firing force as the firing driver is advanced;
      compare the firing force to the firing force threshold; and
      control movement of at least one of the closure driver or the firing driver based on:
         results of the compare; and
         a zone in which the firing driver is positioned.

2. The surgical stapling system of claim 1, wherein the control circuit is to monitor a relationship between the closure driver and the firing driver as the firing driver is advanced, and wherein to set the firing force threshold, the control circuit is to:
   set an initial firing force threshold; and
   adjust the initial firing force threshold to a first adjusted firing force threshold based on the monitored relationship between the closure driver and the firing driver.

3. The surgical stapling system of claim 2, wherein to monitor the relationship between the closure driver and the firing driver, the control circuit is to monitor an amount of co-operation that exists between the closure driver and the firing driver to maintain the second jaw in a closed position.

4. The surgical stapling system of claim 3, wherein:
   the closure driver is to apply a first closure force to the second jaw;
   the firing driver is to apply a second closure force to the second jaw;
   the surgical stapling system further comprises:
      a first closure force sensor to sense the first closure force; and
      a second closure force sensor to sense the second closure force; and
   the control circuit is to:
      receive the first closure force from the first closure force sensor;
      receive the second closure force from the second closure force sensor; and
      monitor the amount of co-operation that exists between the closure driver and the firing driver based on a ratio of the first closure force to the second closure force.

5. The surgical stapling system of claim 4, wherein the control circuit is to determine a zone from a plurality of zones that the firing driver is located, and wherein the zones comprise:
   a first firing zone, wherein the firing driver is determined to be in the first firing zone based on the first closure force being greater than or equal to the second closure force; and
   a second firing zone, wherein the firing driver is determined to be in the second firing zone based on the second closure force being greater than the first closure force.

6. The surgical stapling system of claim 5, wherein the control circuit is to set a threshold co-operation value, wherein the zones comprise a third firing zone, and wherein the firing driver is determined to be in the third firing zone based on the ratio of the first closure force to the second closure force reaching or dropping below the threshold co-operation value.

7. The surgical stapling system of claim 6, wherein the control circuit is to adjust the initial firing force threshold to the first adjusted firing force threshold based on the second closure force being greater than the first closure force, and wherein:
   the control circuit is to control movement of the closure driver and not control movement of the firing driver based on the monitored firing force reaching the initial firing force threshold and the firing driver being positioned in the first firing zone; and
   the control circuit is to control movement of the closure driver and the firing driver based on the monitored firing force reaching the first adjusted firing force threshold and the firing driver being positioned in the second firing zone.

8. The surgical stapling system of claim 7, wherein the control circuit is to adjust the initial firing force threshold to the first adjusted firing force threshold based on the firing driver entering the second firing zone.

9. The surgical stapling system of claim 7, wherein to set the firing force threshold, the control circuit is to adjust the first adjusted firing force threshold to a second adjusted firing force threshold based on the monitored relationship between the closure driver and the firing driver, and wherein the control circuit is to control movement of the firing driver and not control movement of the closure driver based on the firing force reaching the second adjusted firing force threshold and the firing driver being positioned in the third firing zone.

10. The surgical stapling system of claim 9, wherein the control circuit is to adjust the first adjusted firing force threshold to the second adjusted firing force threshold based on the firing driver entering the third firing zone.

11. The surgical stapling system of claim 1, wherein the control circuit is to set:
a first co-operative zone defined over a first portion of the firing stroke; and
a second co-operative zone defined over a second portion of the firing stroke distal to the first portion of the firing stroke.

12. The surgical stapling system of claim 11, further comprising a position sensor coupleable with the control circuit, wherein the position sensor is to sense a position of the firing driver, and wherein the control circuit is to:
determine if the firing driver is in the first co-operative zone or the second co-operative zone; and
control movement of both the closure driver and the firing driver based on:
the firing force reaching the firing force threshold; and
the firing driver being in the first co-operative zone.

13. The surgical stapling system of claim 12, wherein to control movement of the firing driver, the control circuit is to:
pause advancement of firing driver for an amount of time; and
retract the firing driver toward a proximal position based on the amount of time elapsing.

14. The surgical stapling system of claim 13, wherein to control movement of the closure driver, the control circuit is to distally advancing the closure driver from the first position to a second position.

15. The surgical stapling system of claim 14, wherein to control movement of the firing driver, the control circuit is to resume advancement of the firing driver toward the distal position based on the closure driver reaching the second position.

16. The surgical stapling system of claim 12, wherein the control circuit is to control movement of the firing driver and not control movement of the closure driver based on:
the firing force reaching the firing force threshold; and
the firing driver being in the second co-operative zone.

17. The surgical stapling system of claim 16, wherein to control movement of the firing driver, the control circuit is to:
pause advancement of firing driver for an amount of time; and
resume advancement of the firing driver toward the fired position based on the amount of time elapsing.

18. A surgical stapling system, comprising:
an end effector, comprising:
a first jaw; and
a second jaw rotatable relative to the first jaw, wherein the second jaw defines a channel, and wherein the channel comprises:
an upper wall comprising a first force sensor; and
a lower wall comprising a second force sensor;
a closure driver movable to rotate the second jaw relative to the first jaw;
a closure motor to drive the closure driver;
a firing driver movable from an unfired position toward a fired position during a firing stroke, wherein the firing driver comprises a flange to traverse the channel during the firing stroke, wherein the first force sensor is to sense a first force the flange applies to the upper wall, and wherein the second force sensor is to sense a second force the flange applies to the lower wall;
a firing motor to apply a firing force to the firing driver;
a third force sensor to sense the firing force applied by the firing motor; and
a control circuit coupleable with the closure motor, the firing motor, the first force sensor, the second force sensor, and the third force sensor, wherein the control circuit is to:
set a firing force threshold;
advance the closure driver to a first position;
advance the firing driver toward the fired position;
monitor the firing force as the firing driver is advanced;
compare the firing force to the firing force threshold;
determine a clamping state of the second jaw based on results of the compare; and
control movement of the closure driver based on results of the determine.

19. The surgical stapling system of claim 18, wherein to determine the clamping state of the second jaw, the control circuit is to evaluate the first force that the flange applies to the upper wall and the second force that the flange applies to the lower wall.

20. The surgical stapling system of claim 19, wherein to control movement of the closure driver, the control circuit is to:
advance the closure driver based on a determined under-clamped state; and
retract the closure driver based on a determined over-clamped state.

* * * * *